US012571665B2

(12) United States Patent　　　　　　　　(10) Patent No.:　　US 12,571,665 B2

Ruchti et al.　　　　　　　　　　　　　　　(45) Date of Patent:　　　*Mar. 10, 2026

(54) AIR DETECTION SYSTEM AND METHOD FOR DETECTING AIR IN A PUMP OF AN INFUSION SYSTEM

(71) Applicant: ICU Medical, Inc., San Clemente, CA (US)

(72) Inventors: Timothy L. Ruchti, Gurnee, IL (US); Brian G. Markey, Park Forest, IL (US); Anatoly S. Belkin, Glenview, IL (US); Paul T. Kotnik, Commerce Township, MI (US); Mohammad M. Khair, Streamwood, IL (US)

(73) Assignee: ICU Medical, Inc., San Clemente, CA (US)

( * ) Notice: Subject to any disclaimer, the term of this patent is extended or adjusted under 35 U.S.C. 154(b) by 11 days.

This patent is subject to a terminal disclaimer.

(21) Appl. No.: 18/439,582

(22) Filed: Feb. 12, 2024

(65) Prior Publication Data

US 2024/0263981 A1　　Aug. 8, 2024

Related U.S. Application Data

(63) Continuation of application No. 17/810,541, filed on Jul. 1, 2022, now Pat. No. 11,933,650, which is a (Continued)

(51) Int. Cl.
　　*G01F 1/74*　　　　　　(2006.01)
　　*A61M 5/168*　　　　　(2006.01)
　　　　(Continued)

(52) U.S. Cl.
　　CPC ........... *G01F 1/74* (2013.01); *A61M 5/16831* (2013.01); *A61M 5/365* (2013.01); (Continued)

(58) Field of Classification Search
　　None
　　See application file for complete search history.

(56) References Cited

U.S. PATENT DOCUMENTS

| | | | |
|---|---|---|---|
| 3,401,337 | A | 9/1968 | Beusman et al. |
| 3,484,681 | A | 12/1969 | Grady, Jr. et al. |

(Continued)

FOREIGN PATENT DOCUMENTS

| | | |
|---|---|---|
| AU | 2013216679 | 9/2013 |
| BR | PI0704229-9 | 11/2009 |

(Continued)

OTHER PUBLICATIONS

Junda, Lin, "Global development trends of green bonds", Jul. 10, 2018, pp. 9.

(Continued)

*Primary Examiner* — Lina Cordero

(74) *Attorney, Agent, or Firm* — Knobbe, Martens, Olson & Bear, LLP

(57)　　　　　　ABSTRACT

Various systems and methods for detecting air in a chamber of an infusion system are disclosed. In one embodiment, a determination is made that air is contained in the chamber on the basis of a change in the average force exerted against the plunger utilizing a derivative spike for event detection and a systematic reduction in the average force to confirm the nature of the change. In another embodiment, a determination is made that the chamber contains air when a difference between the current force profile and a baseline force profile crosses a threshold. In an additional embodiment, a force profile is classified as being an air force profile or a liquid force profile based on extracted features of the force profile.

22 Claims, 19 Drawing Sheets

Related U.S. Application Data continuation of application No. 16/806,967, filed on Mar. 2, 2020, now Pat. No. 11,378,430, which is a continuation of application No. 16/001,680, filed on Jun. 6, 2018, now Pat. No. 10,578,474, which is a continuation of application No. 13/851,207, filed on Mar. 27, 2013, now Pat. No. 9,995,611.

(60) Provisional application No. 61/618,129, filed on Mar. 30, 2012.

(51) Int. Cl.
| | | |
|---|---|---|
| *A61M 5/36* | (2006.01) | |
| *F04B 43/00* | (2006.01) | |
| *F04B 51/00* | (2006.01) | |

(52) U.S. Cl.
CPC .......... *F04B 43/0081* (2013.01); *F04B 51/00* (2013.01); *A61M 2205/331* (2013.01)

(56) References Cited

U.S. PATENT DOCUMENTS

| | | | |
|---|---|---|---|
| 3,699,320 A | 10/1972 | Zimmerman et al. | |
| 3,727,074 A | 4/1973 | Keller et al. | |
| 3,731,679 A | 5/1973 | Wilhelmson et al. | |
| 3,768,084 A | 10/1973 | Haynes | |
| 3,770,354 A | 11/1973 | Tsuruta et al. | |
| 3,778,702 A | 12/1973 | Finger | |
| 3,806,821 A | 4/1974 | Niemeyer et al. | |
| 3,838,565 A | 10/1974 | Carlyle | |
| 3,847,138 A | 11/1974 | Gollub | |
| 3,854,038 A | 12/1974 | McKinley | |
| 3,886,459 A | 5/1975 | Hufford et al. | |
| 3,890,554 A | 6/1975 | Yoshitake et al. | |
| 3,894,431 A | 7/1975 | Muston et al. | |
| 3,898,637 A | 8/1975 | Wolstenholme | |
| 3,901,231 A | 8/1975 | Olson | |
| 3,909,693 A | 9/1975 | Yoshitake et al. | |
| 3,910,701 A | 10/1975 | Henderson | |
| 3,911,343 A | 10/1975 | Oster | |
| 3,919,608 A | 11/1975 | Usami et al. | |
| 3,921,622 A | 11/1975 | Cole | |
| 3,930,404 A | 1/1976 | Ryden, Jr. | |
| 3,933,431 A | 1/1976 | Trujillo et al. | |
| 3,935,876 A | 2/1976 | Massie et al. | |
| 3,944,963 A | 3/1976 | Hively | |
| 3,966,358 A | 6/1976 | Heimes et al. | |
| 3,971,980 A | 7/1976 | Jungfer et al. | |
| 3,974,681 A | 8/1976 | Namery | |
| 3,974,683 A | 8/1976 | Martin | |
| 3,985,467 A | 10/1976 | Lefferson | |
| 3,990,444 A | 11/1976 | Vial | |
| 3,997,888 A | 12/1976 | Kremer | |
| 4,005,724 A | 2/1977 | Courtot | |
| 4,014,206 A | 3/1977 | Taylor | |
| 4,038,982 A | 8/1977 | Burke | |
| 4,039,269 A | 8/1977 | Pickering | |
| 4,048,474 A | 9/1977 | Olesen | |
| 4,049,954 A | 9/1977 | Da Costa Vieira et al. | |
| 4,055,175 A | 10/1977 | Clemens et al. | |
| 4,057,228 A | 11/1977 | Völker et al. | |
| 4,068,521 A | 1/1978 | Cosentino et al. | |
| 4,078,562 A | 3/1978 | Friedman | |
| 4,089,227 A | 5/1978 | Falgari et al. | |
| 4,094,318 A | 6/1978 | Burke | |
| 4,105,028 A | 8/1978 | Sadlier et al. | |
| 4,114,144 A | 9/1978 | Hyman | |
| 4,151,845 A | 5/1979 | Clemens | |
| 4,155,362 A | 5/1979 | Jess | |
| 4,164,986 A | 8/1979 | Eloy | |
| 4,173,224 A | 11/1979 | Marx | |
| 4,181,610 A | 1/1980 | Shintani et al. | |
| 4,183,244 A | 1/1980 | Kohno et al. | |
| 4,195,515 A | 4/1980 | Smoll | |
| 4,210,138 A | 7/1980 | Jess et al. | |
| 4,213,454 A | 7/1980 | Shim | |
| 4,217,993 A | 8/1980 | Jess et al. | |
| 4,240,294 A | 12/1980 | Grande | |
| 4,240,438 A | 12/1980 | Updike et al. | |
| 4,244,365 A | 1/1981 | McGill | |
| 4,256,437 A | 3/1981 | Brown | |
| 4,261,356 A | 4/1981 | Turner et al. | |
| 4,264,861 A | 4/1981 | Radu et al. | |
| 4,265,240 A | 5/1981 | Jenkins | |
| 4,270,532 A | 6/1981 | Franetzki et al. | |
| 4,277,226 A | 7/1981 | Archibald et al. | |
| 4,278,085 A | 7/1981 | Shim | |
| 4,280,495 A | 7/1981 | Lampert | |
| 4,282,872 A | 8/1981 | Franetzki et al. | |
| 4,286,202 A | 8/1981 | Clancy et al. | |
| 4,290,346 A | 9/1981 | Bujan | |
| 4,291,692 A | 9/1981 | Bowman et al. | |
| 4,292,405 A | 9/1981 | Mascoli | |
| 4,298,357 A | 11/1981 | Permic | |
| 4,308,866 A | 1/1982 | Jeliffe | |
| 4,312,341 A | 1/1982 | Zissimopoulos | |
| 4,319,568 A | 3/1982 | Tregoning | |
| 4,322,201 A | 3/1982 | Archibald | |
| 4,323,849 A | 4/1982 | Smith | |
| 4,324,662 A | 4/1982 | Schnell | |
| 4,328,800 A | 5/1982 | Marx | |
| 4,328,801 A | 5/1982 | Marx | |
| 4,333,045 A | 6/1982 | Oltendorf | |
| 4,343,316 A | 8/1982 | Jespersen | |
| 4,344,429 A | 8/1982 | Gupton et al. | |
| 4,346,707 A | 8/1982 | Whitney et al. | |
| 4,360,019 A | 11/1982 | Portner et al. | |
| 4,366,384 A | 12/1982 | Jensen | |
| 4,367,736 A | 1/1983 | Gupton | |
| 4,370,983 A | 2/1983 | Lichtenstein et al. | |
| 4,373,527 A | 2/1983 | Fischell | |
| 4,379,452 A | 4/1983 | DeVries | |
| 4,381,005 A | 4/1983 | Bujan | |
| 4,384,578 A | 5/1983 | Winkler | |
| 4,385,247 A | 5/1983 | Satomi | |
| 4,391,598 A | 7/1983 | Thompson | |
| 4,392,849 A | 7/1983 | Petre et al. | |
| 4,394,862 A | 7/1983 | Shim | |
| 4,395,259 A | 7/1983 | Prestele et al. | |
| 4,397,194 A | 8/1983 | Soltz | |
| 4,399,362 A | 8/1983 | Cormier et al. | |
| 4,407,659 A | 10/1983 | Adam | |
| 4,411,651 A | 10/1983 | Schulman | |
| 4,418,565 A | 12/1983 | St. John | |
| 4,432,699 A | 2/1984 | Beckman et al. | |
| 4,432,761 A | 2/1984 | Dawe | |
| 4,432,762 A | 2/1984 | Dawe | |
| 4,443,218 A | 4/1984 | Decant, Jr. et al. | |
| 4,444,546 A | 4/1984 | Pazemenas | |
| 4,447,191 A | 5/1984 | Bilstad et al. | |
| 4,447,224 A | 5/1984 | Decant, Jr. et al. | |
| 4,453,931 A | 6/1984 | Pastrone | |
| 4,457,751 A | 7/1984 | Rodler | |
| 4,463,301 A | 7/1984 | Moriguchi et al. | |
| 4,464,170 A | 8/1984 | Clemens | |
| 4,467,654 A | 8/1984 | Murakami et al. | |
| 4,468,222 A | 8/1984 | Lundquist | |
| 4,468,601 A | 8/1984 | Chamran et al. | |
| 4,469,481 A | 9/1984 | Kobayashi | |
| 4,475,666 A | 10/1984 | Bilbrey et al. | |
| 4,475,901 A | 10/1984 | Kraegen et al. | |
| 4,477,756 A | 10/1984 | Moriguchi | |
| 4,479,760 A | 10/1984 | Bilstad et al. | |
| 4,480,218 A | 10/1984 | Hair | |
| 4,480,483 A | 11/1984 | McShane | |
| 4,483,202 A | 11/1984 | Ogua et al. | |
| 4,487,601 A | 12/1984 | Lindemann | |
| 4,492,909 A | 1/1985 | Hartwig | |
| 4,496,346 A | 1/1985 | Mosteller | |
| 4,498,843 A | 2/1985 | Schneider et al. | |
| 4,501,531 A | 2/1985 | Bilstad et al. | |
| 4,504,263 A | 3/1985 | Steuer | |
| 4,507,112 A | 3/1985 | Hillel | |

(56)  References Cited

U.S. PATENT DOCUMENTS

| 4,510,266 | A | 4/1985 | Eertink |
| 4,513,796 | A | 4/1985 | Miller et al. |
| 4,515,584 | A | 5/1985 | Abe et al. |
| 4,519,792 | A | 5/1985 | Dawe |
| 4,521,212 | A | 6/1985 | Ruschke |
| 4,525,163 | A | 6/1985 | Slavik et al. |
| 4,526,568 | A | 7/1985 | Clemens et al. |
| 4,526,574 | A | 7/1985 | Pekkarinen |
| 4,529,401 | A | 7/1985 | Leslie et al. |
| 4,533,350 | A | 8/1985 | Danby et al. |
| 4,543,955 | A | 10/1985 | Schroeppel |
| 4,551,134 | A | 11/1985 | Slavik et al. |
| 4,553,958 | A | 11/1985 | LeCocq |
| 4,559,036 | A | 12/1985 | Wunsch |
| 4,559,037 | A | 12/1985 | Franetzki et al. |
| 4,559,044 | A | 12/1985 | Robinson |
| 4,559,454 | A | 12/1985 | Kramer |
| 4,565,500 | A | 1/1986 | Jeensalute et al. |
| 4,583,981 | A | 4/1986 | Urquhart et al. |
| 4,587,473 | A | 5/1986 | Turvey |
| 4,607,520 | A | 8/1986 | Dam |
| 4,617,014 | A | 10/1986 | Cannon et al. |
| 4,624,661 | A | 11/1986 | Arimond |
| 4,627,835 | A | 12/1986 | Fenton, Jr. |
| 4,633,878 | A | 1/1987 | Bombardieri |
| 4,634,426 | A | 1/1987 | Kamen |
| 4,634,427 | A | 1/1987 | Hannula et al. |
| 4,636,144 | A | 1/1987 | Abe et al. |
| 4,637,813 | A | 1/1987 | DeVries |
| 4,645,489 | A | 2/1987 | Krumme |
| 4,648,869 | A | 3/1987 | Bobo, Jr. |
| 4,652,260 | A | 3/1987 | Fenton, Jr. et al. |
| 4,658,244 | A | 4/1987 | Meijer |
| 4,668,216 | A | 5/1987 | Martin |
| 4,668,945 | A | 5/1987 | Aldrovandi et al. |
| 4,673,334 | A | 6/1987 | Allington et al. |
| 4,673,389 | A | 6/1987 | Archibald et al. |
| 4,676,776 | A | 6/1987 | Howson et al. |
| 4,677,359 | A | 6/1987 | Enami et al. |
| 4,678,979 | A | 7/1987 | Hori |
| 4,678,998 | A | 7/1987 | Muramatsu |
| 4,679,562 | A | 7/1987 | Luksha |
| 4,683,428 | A | 7/1987 | Gete |
| 4,685,903 | A | 8/1987 | Cable et al. |
| 4,690,673 | A | 9/1987 | Blomquist |
| 4,691,153 | A | 9/1987 | Nishimura |
| 4,692,145 | A | 9/1987 | Weyant |
| 4,696,671 | A | 9/1987 | Epstein et al. |
| 4,697,129 | A | 9/1987 | Enami et al. |
| 4,702,675 | A | 10/1987 | Aldrovandi et al. |
| 4,705,506 | A | 11/1987 | Archibald et al. |
| 4,710,106 | A | 12/1987 | Iwata et al. |
| 4,714,462 | A | 12/1987 | DiDomenico |
| 4,714,463 | A | 12/1987 | Archibald et al. |
| 4,718,576 | A | 1/1988 | Tamura et al. |
| 4,720,636 | A | 1/1988 | Benner |
| 4,722,224 | A | 2/1988 | Scheller et al. |
| 4,722,734 | A | 2/1988 | Kolin |
| 4,731,051 | A | 3/1988 | Fischell |
| 4,731,057 | A | 3/1988 | Tanaka et al. |
| 4,737,711 | A | 4/1988 | O'Hare |
| 4,739,346 | A | 4/1988 | Buckley |
| 4,741,732 | A | 5/1988 | Crankshaw et al. |
| 4,741,736 | A | 5/1988 | Brown |
| 4,748,857 | A | 6/1988 | Nakagawa |
| 4,751,445 | A | 6/1988 | Sakai |
| 4,756,706 | A | 7/1988 | Kerns et al. |
| 4,758,228 | A | 7/1988 | Williams |
| 4,763,525 | A | 8/1988 | Cobb |
| 4,764,166 | A | 8/1988 | Spani et al. |
| 4,764,697 | A | 8/1988 | Christiaens |
| 4,769,001 | A | 9/1988 | Prince |
| 4,776,842 | A | 10/1988 | Franetzki et al. |
| 4,781,687 | A | 11/1988 | Wall |
| 4,784,576 | A | 11/1988 | Bloom et al. |
| 4,785,184 | A | 11/1988 | Bien et al. |
| 4,785,799 | A | 11/1988 | Schoon et al. |
| 4,785,969 | A | 11/1988 | McLaughlin |
| 4,786,800 | A | 11/1988 | Kamen |
| 4,789,014 | A | 12/1988 | DiGianfilippo |
| 4,797,655 | A | 1/1989 | Orndal et al. |
| 4,803,389 | A | 2/1989 | Ogawa et al. |
| 4,803,625 | A | 2/1989 | Fu et al. |
| 4,818,186 | A | 4/1989 | Pastrone et al. |
| 4,820,281 | A | 4/1989 | Lawler |
| 4,821,558 | A | 4/1989 | Pastrone et al. |
| 4,828,545 | A | 5/1989 | Epstein et al. |
| 4,828,693 | A | 5/1989 | Lindsay |
| 4,829,448 | A | 5/1989 | Balding et al. |
| 4,838,856 | A | 6/1989 | Mulreany et al. |
| 4,838,857 | A | 6/1989 | Strowe et al. |
| 4,840,542 | A | 6/1989 | Abbott |
| 4,842,584 | A | 6/1989 | Pastrone et al. |
| 4,845,487 | A | 7/1989 | Frantz et al. |
| 4,846,792 | A | 7/1989 | Bobo et al. |
| 4,850,805 | A | 7/1989 | Madsen et al. |
| 4,851,755 | A | 7/1989 | Fincher |
| 4,854,324 | A | 8/1989 | Hirschman et al. |
| 4,856,339 | A | 8/1989 | Williams |
| 4,857,048 | A | 8/1989 | Simons et al. |
| 4,857,050 | A | 8/1989 | Lentz et al. |
| 4,858,154 | A | 8/1989 | Anderson et al. |
| 4,863,425 | A | 9/1989 | Slate et al. |
| 4,865,584 | A | 9/1989 | Epstein et al. |
| 4,869,722 | A | 9/1989 | Heyman |
| 4,874,359 | A | 10/1989 | White et al. |
| 4,881,413 | A | 11/1989 | Georgi et al. |
| 4,882,575 | A | 11/1989 | Kawahara |
| 4,884,013 | A | 11/1989 | Jackson et al. |
| 4,884,065 | A | 11/1989 | Crouse et al. |
| 4,886,422 | A | 12/1989 | Takeuchi et al. |
| 4,898,576 | A | 2/1990 | Philip |
| 4,898,578 | A | 2/1990 | Rubalcaba, Jr. |
| 4,906,103 | A | 3/1990 | Kao |
| 4,908,017 | A | 3/1990 | Howson et al. |
| 4,908,019 | A | 3/1990 | Urquhart et al. |
| 4,910,475 | A | 3/1990 | Lin |
| 4,919,595 | A | 4/1990 | Likuski et al. |
| 4,919,596 | A | 4/1990 | Slate et al. |
| 4,925,444 | A | 5/1990 | Orkin et al. |
| 4,927,411 | A | 5/1990 | Pastrone et al. |
| 4,930,358 | A | 6/1990 | Motegi et al. |
| 4,936,820 | A | 6/1990 | Dennehey |
| 4,936,828 | A | 6/1990 | Chiang |
| 4,938,079 | A | 7/1990 | Goldberg |
| 4,943,279 | A | 7/1990 | Samiotes et al. |
| 4,946,439 | A | 8/1990 | Eggers |
| 4,947,856 | A | 8/1990 | Beard |
| 4,950,235 | A | 8/1990 | Slate et al. |
| 4,950,244 | A | 8/1990 | Fellingham |
| 4,959,050 | A | 9/1990 | Bobo, Jr. |
| 4,966,579 | A | 10/1990 | Polaschegg |
| 4,968,941 | A | 11/1990 | Rogers |
| 4,972,842 | A | 11/1990 | Korten et al. |
| 4,976,687 | A | 12/1990 | Martin |
| 4,978,335 | A | 12/1990 | Arthur, III |
| 4,979,940 | A | 12/1990 | Lapp et al. |
| 4,981,467 | A | 1/1991 | Bobo et al. |
| 5,000,663 | A | 3/1991 | Gorton |
| 5,000,739 | A | 3/1991 | Kulisz et al. |
| 5,006,050 | A | 4/1991 | Cooke et al. |
| 5,010,473 | A | 4/1991 | Jacobs |
| 5,014,714 | A | 5/1991 | Millay et al. |
| 5,014,798 | A | 5/1991 | Glynn |
| 5,018,945 | A | 5/1991 | D'Silva |
| 5,026,348 | A | 6/1991 | Venegas |
| 5,028,857 | A | 7/1991 | Taghezout |
| 5,032,112 | A | 7/1991 | Fairchild et al. |
| 5,034,004 | A | 7/1991 | Crankshaw |
| 5,035,143 | A | 7/1991 | Latimer et al. |
| 5,040,699 | A | 8/1991 | Gangemi |
| 5,041,086 | A | 8/1991 | Koenig et al. |
| 5,043,706 | A | 8/1991 | Oliver |
| 5,045,069 | A | 9/1991 | Imparato |

(56)                References Cited

U.S. PATENT DOCUMENTS 5,049,047  A      9/1991   Polaschegg et al.
5,052,230  A     10/1991   Lang
5,053,747  A     10/1991   Slate et al.
5,055,761  A     10/1991   Mills
5,056,992  A     10/1991   Simons
5,058,161  A     10/1991   Weiss
5,059,171  A     10/1991   Bridge
5,063,603  A     11/1991   Burt
5,064,412  A     11/1991   Henke et al.
5,078,683  A      1/1992   Sancoff et al.
5,084,663  A      1/1992   Olsson
5,084,828  A      1/1992   Kaufman et al.
5,088,981  A      2/1992   Howson et al.
5,096,385  A      3/1992   Georgi et al.
5,097,505  A      3/1992   Weiss
5,100,380  A      3/1992   Epstein et al.
5,102,392  A      4/1992   Sakai et al.
5,103,211  A      4/1992   Daoud et al.
5,104,374  A      4/1992   Bishko et al.
5,108,367  A      4/1992   Epstein et al.
5,109,850  A      5/1992   Blanco et al.
5,116,203  A      5/1992   Nartwick et al.
5,116,312  A      5/1992   Blakenship et al.
5,116,316  A      5/1992   Sertic
5,123,275  A      6/1992   Daoud et al.
5,124,627  A      6/1992   Okada
5,125,499  A      6/1992   Saathoff et al.
5,131,816  A      7/1992   Brown
5,132,603  A      7/1992   Yoshimoto
5,153,827  A     10/1992   Coutre et al.
5,158,441  A     10/1992   Aid
5,161,222  A     11/1992   Montejo et al.
5,174,472  A     12/1992   Raque et al.
5,176,631  A      1/1993   Koenig
5,176,646  A      1/1993   Kuroda
5,179,340  A      1/1993   Rogers
5,180,287  A      1/1993   Natwick et al.
5,181,910  A      1/1993   Scanlon
5,186,057  A      2/1993   Everhart
5,188,603  A      2/1993   Vaillancourt
5,190,522  A      3/1993   Wocicki et al.
5,191,795  A      3/1993   Fellingham et al.
5,192,340  A      3/1993   Grant et al.
5,194,796  A      3/1993   Domeki et al.
5,198,776  A      3/1993   Carr
5,200,090  A      4/1993   Ford
5,205,819  A      4/1993   Ross et al.
5,206,522  A      4/1993   Danby et al.
5,207,642  A      5/1993   Orkin et al.
5,211,626  A      5/1993   Frank et al.
5,213,573  A      5/1993   Sorich et al.
5,215,450  A      6/1993   Tamari
5,216,597  A      6/1993   Beckers
5,219,099  A      6/1993   Spence et al.
5,219,327  A      6/1993   Okada
5,221,268  A      6/1993   Barton et al.
5,229,713  A      7/1993   Bullock et al.
5,232,476  A      8/1993   Grant
5,233,571  A      8/1993   Wirtschafter
5,237,309  A      8/1993   Frantz et al.
5,242,406  A      9/1993   Gross et al.
5,242,408  A      9/1993   Jhuboo et al.
5,243,982  A      9/1993   Möstl et al.
5,244,463  A      9/1993   Cordner, Jr. et al.
5,244,568  A      9/1993   Lindsay et al.
5,254,096  A     10/1993   Rondelet et al.
5,256,155  A     10/1993   Yerlikaya et al.
5,256,156  A     10/1993   Kern et al.
5,256,157  A     10/1993   Samiotes et al.
5,257,206  A     10/1993   Hanson
5,260,665  A     11/1993   Goldberg
5,262,944  A     11/1993   Weisner et al.
5,267,980  A     12/1993   Dirr et al.
5,274,316  A     12/1993   Evans et al.
5,276,610  A      1/1994   Maeda et al.

5,280,728  A      1/1994   Sato et al.
5,283,510  A      2/1994   Tamaki et al.
5,287,851  A      2/1994   Beran et al.
5,292,306  A      3/1994   Wynkoop et al.
5,295,967  A      3/1994   Rondelet et al.
5,298,021  A      3/1994   Sherer
5,303,585  A      4/1994   Lichte
5,304,126  A      4/1994   Epstein et al.
5,304,216  A      4/1994   Wallace
5,308,333  A      5/1994   Skakoon
5,317,506  A      5/1994   Coutre et al.
5,319,363  A      6/1994   Welch et al.
5,319,979  A      6/1994   Abrahamson
5,321,392  A      6/1994   Skakoon et al.
5,325,170  A      6/1994   Bornhop
5,325,728  A      7/1994   Zimmerman et al.
5,328,460  A      7/1994   Lord et al.
5,330,634  A      7/1994   Wong et al.
5,333,497  A      8/1994   Braend et al.
5,336,051  A      8/1994   Tamari
5,338,157  A      8/1994   Blomquist
5,342,298  A      8/1994   Michaels
5,343,734  A      9/1994   Maeda et al.
5,343,885  A      9/1994   Grant
5,346,466  A      9/1994   Yerlikaya et al.
5,356,378  A     10/1994   Doan et al.
5,359,271  A     10/1994   Husher
D352,778   S     11/1994   Irvin et al.
5,364,346  A     11/1994   Schrezenmeir
5,366,346  A     11/1994   Danby
5,368,562  A     11/1994   Blomquist et al.
5,374,865  A     12/1994   Yoshimura et al.
5,376,070  A     12/1994   Purvis et al.
5,378,231  A      1/1995   Johnson et al.
5,382,232  A      1/1995   Hague et al.
5,383,369  A      1/1995   Khuri-Yakub et al.
5,389,071  A      2/1995   Kawahara et al.
5,389,078  A      2/1995   Zalesky et al.
5,392,638  A      2/1995   Kawahara
5,394,732  A      3/1995   Johnson et al.
5,395,320  A      3/1995   Padda et al.
5,399,171  A      3/1995   Bowman et al.
5,406,954  A      4/1995   Tomita
5,408,326  A      4/1995   Priestley
5,415,528  A      5/1995   Ogden et al.
5,417,119  A      5/1995   Smoll
5,417,222  A      5/1995   Dempsey et al.
5,417,395  A      5/1995   Fowler et al.
5,418,443  A      5/1995   Kikuchi
5,421,208  A      6/1995   Packard et al.
5,423,748  A      6/1995   Uhala
5,423,749  A      6/1995   Merte et al.
5,423,759  A      6/1995   Campbell
5,428,284  A      6/1995   Kaneda et al.
5,429,485  A      7/1995   Dodge
5,429,601  A      7/1995   Conley
5,429,602  A      7/1995   Hauser
5,431,627  A      7/1995   Pastrone et al.
5,434,508  A      7/1995   Ishida
5,437,624  A      8/1995   Langley et al.
5,444,316  A      8/1995   Ohya et al.
5,444,378  A      8/1995   Rogers
5,445,621  A      8/1995   Poli et al.
5,450,758  A      9/1995   Smoll
5,451,881  A      9/1995   Finger
5,455,423  A     10/1995   Mount et al.
5,455,851  A     10/1995   Chaco et al.
5,463,906  A     11/1995   Spani et al.
5,464,392  A     11/1995   Epstein et al.
5,465,082  A     11/1995   Chaco
5,469,851  A     11/1995   Lipschutz
5,473,948  A     12/1995   Moss et al.
5,480,294  A      1/1996   Di Perna et al.
5,482,438  A      1/1996   Anderson et al.
5,485,408  A      1/1996   Blomquist
5,486,286  A      1/1996   Peterson et al.
5,489,265  A      2/1996   Montalvo et al.
5,495,566  A      2/1996   Kwatinetz
5,496,273  A      3/1996   Pastrone et al.

(56) References Cited

U.S. PATENT DOCUMENTS

| | | |
|---|---|---|
| 5,505,696 A | 4/1996 | Miki |
| 5,505,828 A | 4/1996 | Wong et al. |
| 5,507,288 A | 4/1996 | Bocker et al. |
| 5,507,412 A | 4/1996 | Ebert et al. |
| 5,520,637 A | 5/1996 | Pager et al. |
| 5,522,798 A | 6/1996 | Johnson et al. |
| 5,522,799 A | 6/1996 | Furukawa |
| 5,527,344 A | 6/1996 | Arzbaecher et al. |
| 5,527,630 A | 6/1996 | Nagata |
| 5,533,389 A | 7/1996 | Kamen et al. |
| 5,537,853 A | 7/1996 | Finburgh et al. |
| 5,542,040 A | 7/1996 | Chang et al. |
| 5,545,140 A | 8/1996 | Conero et al. |
| 5,547,470 A | 8/1996 | Johnson et al. |
| 5,551,850 A | 9/1996 | Williamson et al. |
| 5,554,013 A | 9/1996 | Owens et al. |
| 5,554,115 A | 9/1996 | Thomas et al. |
| 5,558,638 A | 9/1996 | Evers et al. |
| 5,562,615 A | 10/1996 | Nassif |
| 5,563,486 A | 10/1996 | Yamamoto et al. |
| 5,572,105 A | 11/1996 | Nojima et al. |
| 5,573,502 A | 11/1996 | LeCocq et al. |
| 5,583,280 A | 12/1996 | Mo et al. |
| 5,584,667 A | 12/1996 | Davis |
| 5,584,806 A | 12/1996 | Amano |
| 5,586,868 A | 12/1996 | Lawless et al. |
| 5,590,653 A | 1/1997 | Aida et al. |
| 5,594,786 A | 1/1997 | Chaco et al. |
| 5,600,073 A | 2/1997 | Hill |
| 5,601,420 A | 2/1997 | Warner et al. |
| 5,609,575 A | 3/1997 | Larson et al. |
| 5,609,576 A | 3/1997 | Voss |
| 5,611,784 A | 3/1997 | Barresi et al. |
| 5,616,124 A | 4/1997 | Hague et al. |
| 5,620,312 A | 4/1997 | Hyman et al. |
| 5,620,608 A | 4/1997 | Rosa et al. |
| 5,626,140 A | 5/1997 | Feldman et al. |
| 5,626,151 A | 5/1997 | Linden |
| 5,626,563 A | 5/1997 | Dodge et al. |
| 5,627,443 A | 5/1997 | Kimura et al. |
| 5,628,309 A | 5/1997 | Brown |
| 5,628,731 A | 5/1997 | Dodge et al. |
| 5,630,710 A | 5/1997 | Tune et al. |
| 5,634,896 A | 6/1997 | Bryant et al. |
| 5,637,095 A | 6/1997 | Nason et al. |
| 5,640,075 A | 6/1997 | Brasseur et al. |
| 5,640,150 A | 6/1997 | Atwater |
| 5,643,212 A | 7/1997 | Coutre et al. |
| 5,648,710 A | 7/1997 | Ikeda |
| 5,649,536 A | 7/1997 | Ogura et al. |
| 5,651,775 A | 7/1997 | Walker et al. |
| 5,657,000 A | 8/1997 | Ellingboe |
| 5,658,133 A | 8/1997 | Anderson et al. |
| 5,658,250 A | 8/1997 | Blomquist et al. |
| 5,659,234 A | 8/1997 | Cresens |
| 5,661,245 A | 8/1997 | Svoboda et al. |
| D384,052 S | 9/1997 | Kodosky |
| 5,662,612 A | 9/1997 | Niehoff |
| 5,665,065 A | 9/1997 | Colman et al. |
| 5,669,877 A | 9/1997 | Blomquist |
| 5,672,154 A | 9/1997 | Sillén et al. |
| 5,672,832 A | 9/1997 | Cucci et al. |
| 5,681,285 A | 10/1997 | Ford et al. |
| 5,681,286 A | 10/1997 | Niehoff |
| 5,685,844 A | 11/1997 | Marttila |
| 5,685,866 A | 11/1997 | Lopez |
| 5,687,717 A | 11/1997 | Halpern et al. |
| 5,689,229 A | 11/1997 | Chaco et al. |
| 5,691,613 A | 11/1997 | Gutwillinger |
| 5,695,464 A | 12/1997 | Viallet |
| 5,695,473 A | 12/1997 | Olsen |
| 5,697,899 A | 12/1997 | Hillman et al. |
| 5,697,916 A | 12/1997 | Schraga |
| 5,712,795 A | 1/1998 | Layman et al. |
| 5,713,856 A | 2/1998 | Eggers et al. |
| 5,714,691 A | 2/1998 | Hill |
| 5,718,562 A | 2/1998 | Lawless et al. |
| 5,718,569 A | 2/1998 | Holst |
| 5,720,721 A | 2/1998 | Dumas et al. |
| 5,722,417 A | 3/1998 | Rudolph |
| 5,728,074 A | 3/1998 | Castellano et al. |
| 5,728,948 A | 3/1998 | Bignell et al. |
| 5,733,257 A | 3/1998 | Stemby |
| 5,733,259 A | 3/1998 | Valcke et al. |
| 5,734,464 A | 3/1998 | Gibbs |
| 5,738,659 A | 4/1998 | Neer et al. |
| 5,743,856 A | 4/1998 | Oka et al. |
| 5,744,027 A | 4/1998 | Connell et al. |
| 5,744,929 A | 4/1998 | Miyazaki |
| 5,745,378 A | 4/1998 | Barker et al. |
| 5,752,813 A | 5/1998 | Tyner et al. |
| 5,752,918 A | 5/1998 | Fowler et al. |
| 5,752,919 A | 5/1998 | Schrimpf |
| 5,755,691 A | 5/1998 | Hilborne |
| 5,758,643 A | 6/1998 | Wong et al. |
| 5,761,072 A | 6/1998 | Bardsley, Jr. et al. |
| 5,764,034 A | 6/1998 | Bowman et al. |
| 5,766,155 A | 6/1998 | Hyman et al. |
| 5,772,635 A | 6/1998 | Dastur et al. |
| 5,778,256 A | 7/1998 | Darbee |
| 5,781,442 A | 7/1998 | Engleson et al. |
| 5,782,805 A | 7/1998 | Meinzer et al. |
| 5,788,669 A | 8/1998 | Peterson |
| 5,788,674 A | 8/1998 | McWilliams |
| 5,789,923 A | 8/1998 | Shimoyama et al. |
| 5,792,069 A | 8/1998 | Greenwald et al. |
| 5,793,211 A | 8/1998 | Shimoyama et al. |
| 5,795,327 A | 8/1998 | Wilson et al. |
| 5,798,934 A | 8/1998 | Saigo et al. |
| 5,800,387 A | 9/1998 | Duffy et al. |
| 5,803,712 A | 9/1998 | Davis et al. |
| 5,803,917 A | 9/1998 | Butterfield |
| 5,805,455 A | 9/1998 | Lipps |
| 5,807,322 A | 9/1998 | Lindsey et al. |
| 5,810,770 A | 9/1998 | Chin et al. |
| 5,813,972 A | 9/1998 | Nazarian et al. |
| 5,814,004 A | 9/1998 | Tamari |
| 5,814,015 A | 9/1998 | Gargano et al. |
| 5,816,779 A | 10/1998 | Lawless et al. |
| 5,822,715 A | 10/1998 | Worthington et al. |
| 5,827,179 A | 10/1998 | Lichter et al. |
| 5,827,223 A | 10/1998 | Butterfield |
| 5,832,448 A | 11/1998 | Brown |
| 5,836,910 A | 11/1998 | Duffy et al. |
| 5,841,261 A | 11/1998 | Nojima et al. |
| 5,841,284 A | 11/1998 | Takahashi |
| 5,843,035 A | 12/1998 | Bowman |
| 5,848,971 A | 12/1998 | Fowler et al. |
| 5,850,344 A | 12/1998 | Conkright |
| 5,857,843 A | 1/1999 | Leason et al. |
| 5,864,330 A | 1/1999 | Haynes |
| 5,865,805 A | 2/1999 | Ziemba |
| 5,867,821 A | 2/1999 | Ballantyne et al. |
| 5,871,465 A | 2/1999 | Vasko |
| 5,872,453 A | 2/1999 | Shimoyama et al. |
| 5,875,195 A | 2/1999 | Dixon |
| 5,882,300 A | 3/1999 | Malinouskas et al. |
| 5,882,339 A | 3/1999 | Beiser et al. |
| 5,885,245 A | 3/1999 | Lynch et al. |
| 5,889,379 A | 3/1999 | Yanagi et al. |
| 5,891,051 A | 4/1999 | Han et al. |
| 5,894,209 A | 4/1999 | Takagi et al. |
| 5,897,493 A | 4/1999 | Brown |
| 5,897,498 A | 4/1999 | Canfield, II et al. |
| 5,898,292 A | 4/1999 | Takemoto et al. |
| 5,899,665 A | 5/1999 | Makino et al. |
| 5,901,150 A | 5/1999 | Jhuboo et al. |
| 5,904,666 A | 5/1999 | DeDecker et al. |
| 5,904,668 A | 5/1999 | Hyman et al. |
| 5,905,207 A | 5/1999 | Schalk |
| 5,906,598 A | 5/1999 | Giesier |
| 5,910,252 A | 6/1999 | Truitt et al. |
| 5,915,240 A | 6/1999 | Karpf |
| 5,920,263 A | 7/1999 | Huttenhoff et al. |

(56) References Cited

U.S. PATENT DOCUMENTS

| | | | |
|---|---|---|---|
| 5,923,159 A | 7/1999 | Ezell |
| 5,924,074 A | 7/1999 | Evans |
| 5,927,349 A | 7/1999 | Martucci |
| 5,932,119 A | 8/1999 | Kaplan et al. |
| 5,932,987 A | 8/1999 | McLoughlin |
| 5,935,066 A | 8/1999 | Harris |
| 5,935,099 A | 8/1999 | Peterson et al. |
| 5,935,106 A | 8/1999 | Olsen |
| 5,938,634 A | 8/1999 | Packard |
| 5,938,636 A | 8/1999 | Kramer et al. |
| 5,941,846 A | 8/1999 | Duffy et al. |
| 5,944,660 A | 8/1999 | Kimball et al. |
| 5,947,911 A | 9/1999 | Wong et al. |
| 5,954,527 A | 9/1999 | Jhuboo et al. |
| 5,954,696 A | 9/1999 | Ryan et al. |
| 5,956,023 A | 9/1999 | Lyle et al. |
| 5,956,501 A | 9/1999 | Brown |
| 5,957,885 A | 9/1999 | Bollish et al. |
| 5,957,890 A | 9/1999 | Mann et al. |
| 5,971,594 A | 10/1999 | Sahai et al. |
| 5,973,497 A | 10/1999 | Bergk et al. |
| 5,975,081 A | 11/1999 | Hood et al. |
| 5,989,222 A | 11/1999 | Cole et al. |
| 5,990,838 A | 11/1999 | Burns et al. |
| 5,991,525 A | 11/1999 | Shah et al. |
| 5,993,393 A | 11/1999 | Ryan et al. |
| 5,994,876 A | 11/1999 | Canny et al. |
| 5,997,476 A | 12/1999 | Brown |
| 6,000,828 A | 12/1999 | Leet |
| 6,003,006 A | 12/1999 | Colella et al. |
| 6,003,388 A | 12/1999 | Oeftering |
| 6,012,034 A | 1/2000 | Hamparian et al. |
| 6,017,318 A | 1/2000 | Gauthier et al. |
| 6,017,493 A | 1/2000 | Cambron |
| 6,021,392 A | 2/2000 | Lester et al. |
| 6,023,977 A | 2/2000 | Langdon et al. |
| 6,024,539 A | 2/2000 | Blomquist |
| 6,027,441 A | 2/2000 | Cantu |
| 6,028,412 A | 2/2000 | Shine et al. |
| 6,032,676 A | 3/2000 | Moore |
| 6,033,561 A | 3/2000 | Schoendorfer |
| 6,036,017 A | 3/2000 | Bayliss, IV |
| 6,068,612 A | 5/2000 | Bowman |
| 6,068,615 A | 5/2000 | Brown et al. |
| 6,073,106 A | 6/2000 | Rozen et al. |
| 6,077,246 A | 6/2000 | Kullas et al. |
| 6,083,206 A | 7/2000 | Molko |
| 6,089,104 A | 7/2000 | Chang |
| 6,104,295 A | 8/2000 | Gaisser et al. |
| 6,110,152 A | 8/2000 | Kovelman |
| 6,110,153 A | 8/2000 | Davis |
| RE36,871 E | 9/2000 | Epstein et al. |
| 6,120,459 A | 9/2000 | Nitzan et al. |
| 6,122,536 A | 9/2000 | Sun et al. |
| 6,142,008 A | 11/2000 | Cole et al. |
| 6,150,942 A | 11/2000 | O'Brien |
| 6,157,914 A | 12/2000 | Seto et al. |
| 6,158,288 A | 12/2000 | Smith |
| 6,158,965 A | 12/2000 | Butterfield et al. |
| 6,159,147 A | 12/2000 | Lichter et al. |
| 6,159,186 A | 12/2000 | Wickham et al. |
| 6,164,921 A | 12/2000 | Moubayed et al. |
| 6,168,561 B1 | 1/2001 | Cantu |
| 6,178,827 B1 | 1/2001 | Feller |
| 6,182,667 B1 | 2/2001 | Hanks et al. |
| 6,186,141 B1 | 2/2001 | Pike et al. |
| 6,189,105 B1 | 2/2001 | Lopes |
| 6,192,752 B1 | 2/2001 | Blaine |
| 6,195,589 B1 | 2/2001 | Ketcham |
| 6,202,711 B1 | 3/2001 | Martucci |
| 6,203,528 B1 | 3/2001 | Deckert |
| 6,208,107 B1 | 3/2001 | Maske et al. |
| 6,212,936 B1 | 4/2001 | Meisberger |
| 6,213,972 B1 | 4/2001 | Butterfield |
| 6,231,320 B1 | 5/2001 | Lawless et al. |
| 6,234,176 B1 | 5/2001 | Domae et al. |
| 6,236,326 B1 | 5/2001 | Murphy et al. |
| 6,237,398 B1 | 5/2001 | Porat et al. |
| 6,241,704 B1 | 6/2001 | Peterson et al. |
| 6,248,067 B1 | 6/2001 | Causey, III et al. |
| 6,250,132 B1 | 6/2001 | Drzewiecki |
| 6,259,355 B1 | 7/2001 | Chaco et al. |
| 6,259,587 B1 | 7/2001 | Sheldon et al. |
| 6,261,065 B1 | 7/2001 | Nayak |
| 6,262,946 B1 | 7/2001 | Khuri-Yakub et al. |
| 6,267,559 B1 | 7/2001 | Mossman et al. |
| 6,267,725 B1 | 7/2001 | Dubberstein et al. |
| 6,269,340 B1 | 7/2001 | Ford et al. |
| 6,270,455 B1 | 8/2001 | Brown |
| 6,271,813 B1 | 8/2001 | Palalau |
| 6,277,072 B1 | 8/2001 | Bardy |
| 6,277,099 B1 | 8/2001 | Strowe et al. |
| 6,280,380 B1 | 8/2001 | Bardy |
| 6,280,391 B1 | 8/2001 | Olson et al. |
| 6,280,408 B1 | 8/2001 | Sipin |
| 6,283,761 B1 | 9/2001 | Joao |
| 6,285,155 B1 | 9/2001 | Maske et al. |
| 6,312,378 B1 | 11/2001 | Bardy |
| 6,322,516 B1 | 11/2001 | Masuda et al. |
| 6,330,351 B1 | 12/2001 | Yasunaga |
| 6,336,053 B1 | 1/2002 | Beatty |
| 6,337,675 B1 | 1/2002 | Toffolo et al. |
| 6,345,539 B1 | 2/2002 | Rawes et al. |
| 6,347,553 B1 | 2/2002 | Morris et al. |
| 6,349,740 B1 | 2/2002 | Cho et al. |
| 6,358,225 B1 | 3/2002 | Butterfield |
| 6,358,387 B1 | 3/2002 | Kopf-Sill et al. |
| 6,362,591 B1 | 3/2002 | Moberg |
| 6,385,505 B1 | 5/2002 | Lipps |
| 6,386,050 B1 | 5/2002 | Yin et al. |
| 6,394,958 B1 | 5/2002 | Bratteli et al. |
| 6,396,583 B1 | 5/2002 | Clare |
| D459,362 S | 6/2002 | Platz |
| 6,398,760 B1 | 6/2002 | Danby |
| 6,405,076 B1 | 6/2002 | Taylor et al. |
| 6,408,679 B1 | 6/2002 | Kline-Schoder et al. |
| 6,409,699 B1 | 6/2002 | Ash |
| 6,413,238 B1 | 7/2002 | Maget |
| 6,416,291 B1 | 7/2002 | Butterfield et al. |
| 6,418,334 B1 | 7/2002 | Unger et al. |
| 6,418,535 B1 | 7/2002 | Kulakowski et al. |
| 6,445,053 B1 | 9/2002 | Cho |
| 6,456,245 B1 | 9/2002 | Crawford |
| 6,457,346 B1 | 10/2002 | Kline-Schoder et al. |
| 6,463,785 B1 | 10/2002 | Kline-Schoder et al. |
| 6,467,331 B1 | 10/2002 | Kline-Schoder et al. |
| 6,468,242 B1 | 10/2002 | Wilson et al. |
| 6,475,178 B1 | 11/2002 | Krajewski |
| 6,481,980 B1 | 11/2002 | Vandlik |
| 6,482,158 B2 | 11/2002 | Mault |
| 6,482,185 B1 | 11/2002 | Hartmann |
| 6,485,263 B1 | 11/2002 | Bryant et al. |
| 6,485,418 B2 | 11/2002 | Yasushi et al. |
| 6,485,465 B2 | 11/2002 | Moberg et al. |
| 6,487,916 B1 | 12/2002 | Gomm et al. |
| 6,489,896 B1 | 12/2002 | Platt |
| 6,494,694 B2 | 12/2002 | Lawless et al. |
| 6,494,831 B1 | 12/2002 | Koritzinsky |
| 6,497,680 B1 | 12/2002 | Holst et al. |
| 6,503,221 B1 | 1/2003 | Briggs |
| 6,512,944 B1 | 1/2003 | Kovtun et al. |
| 6,516,667 B1 | 2/2003 | Broad et al. |
| 6,517,482 B1 | 2/2003 | Eiden et al. |
| 6,519,569 B1 | 2/2003 | White et al. |
| 6,529,751 B1 | 3/2003 | Van Driel et al. |
| 6,531,708 B1 | 3/2003 | Malmstrom |
| 6,539,315 B1 | 3/2003 | Adams et al. |
| D473,238 S | 4/2003 | Cockerill |
| 6,540,672 B1 | 4/2003 | Simonsen et al. |
| 6,544,212 B2 | 4/2003 | Galley et al. |
| 6,544,228 B1 | 4/2003 | Heitmeier |
| 6,558,125 B1 | 5/2003 | Futterknecht |
| 6,558,351 B1 | 5/2003 | Steil et al. |
| 6,562,012 B1 | 5/2003 | Brown et al. |

(56)                References Cited

U.S. PATENT DOCUMENTS

| | | |
|---|---|---|
| 6,564,825 B2 | 5/2003 | Lowery et al. |
| 6,565,509 B1 | 5/2003 | Say et al. |
| 6,568,416 B2 | 5/2003 | Tucker et al. |
| 6,572,542 B1 | 6/2003 | Houben et al. |
| 6,572,545 B2 | 6/2003 | Knobbe et al. |
| 6,572,576 B2 | 6/2003 | Brugger et al. |
| 6,578,422 B2 | 6/2003 | Lam et al. |
| 6,578,435 B2 | 6/2003 | Gould et al. |
| 6,581,117 B1 | 6/2003 | Klein et al. |
| RE38,189 E | 7/2003 | Walker et al. |
| 6,585,675 B1 | 7/2003 | O'Mahony et al. |
| 6,589,229 B1 | 7/2003 | Connelly et al. |
| 6,589,792 B1 | 7/2003 | Malachowski |
| 6,599,281 B1 | 7/2003 | Struys et al. |
| 6,599,282 B2 | 7/2003 | Burko |
| 6,602,191 B2 | 8/2003 | Quy |
| 6,605,072 B2 | 8/2003 | Struys et al. |
| 6,606,047 B1 | 8/2003 | Börjesson et al. |
| 6,609,047 B1 | 8/2003 | Lipps |
| 6,615,674 B2 | 9/2003 | Ohnishi |
| 6,616,633 B1 | 9/2003 | Butterfield et al. |
| 6,617,564 B2 | 9/2003 | Ockerse et al. |
| 6,618,916 B1 | 9/2003 | Eberle et al. |
| 6,622,542 B2 | 9/2003 | Derek |
| 6,622,561 B2 | 9/2003 | Lam et al. |
| D481,121 S | 10/2003 | Evans |
| 6,629,449 B1 | 10/2003 | Kline-Schoder et al. |
| 6,634,233 B2 | 10/2003 | He |
| 6,640,246 B1 | 10/2003 | Gardy, Jr. et al. |
| 6,641,533 B2 | 11/2003 | Causey, III et al. |
| 6,641,541 B1 | 11/2003 | Lovett et al. |
| 6,648,861 B2 | 11/2003 | Platt et al. |
| 6,652,455 B1 | 11/2003 | Kocher |
| 6,653,937 B2 | 11/2003 | Nelson et al. |
| 6,659,980 B2 | 12/2003 | Moberg et al. |
| D485,356 S | 1/2004 | Evans |
| 6,685,668 B1 | 2/2004 | Cho et al. |
| 6,685,678 B2 | 2/2004 | Evans et al. |
| 6,689,069 B2 | 2/2004 | Bratteli et al. |
| 6,689,091 B2 | 2/2004 | Bui et al. |
| 6,692,241 B2 | 2/2004 | Watanabe et al. |
| D487,574 S | 3/2004 | Glaser |
| 6,716,004 B2 | 4/2004 | Vandlik |
| 6,719,535 B2 | 4/2004 | Rakestraw et al. |
| 6,721,582 B2 | 4/2004 | Trepagnier et al. |
| 6,722,211 B1 | 4/2004 | Ciobanu et al. |
| 6,725,200 B1 | 4/2004 | Rost |
| 6,725,721 B2 | 4/2004 | Venczel |
| 6,731,989 B2 | 5/2004 | Engleson et al. |
| 6,732,595 B2 | 5/2004 | Lynnworth |
| 6,738,052 B1 | 5/2004 | Manke et al. |
| 6,740,072 B2 | 5/2004 | Starkweather et al. |
| 6,741,212 B2 | 5/2004 | Kralovec et al. |
| 6,748,808 B2 | 6/2004 | Lam et al. |
| 6,749,403 B2 | 6/2004 | Bryant et al. |
| 6,752,787 B1 | 6/2004 | Causey, III et al. |
| 6,753,842 B1 | 6/2004 | Williams et al. |
| 6,759,007 B1 | 7/2004 | Westberg |
| 6,760,643 B2 | 7/2004 | Lipps |
| 6,768,920 B2 | 7/2004 | Lange |
| 6,773,412 B2 | 8/2004 | O'Mahony |
| 6,780,156 B2 | 8/2004 | Haueter et al. |
| 6,783,328 B2 | 8/2004 | Lucke et al. |
| 6,785,573 B2 | 8/2004 | Kovtun et al. |
| 6,786,885 B2 | 9/2004 | Hochman et al. |
| 6,789,426 B2 | 9/2004 | Yaralioglu et al. |
| 6,790,198 B1 | 9/2004 | White et al. |
| 6,793,625 B2 | 9/2004 | Cavallaro et al. |
| 6,801,227 B2 | 10/2004 | Bocionek et al. |
| 6,805,671 B2 | 10/2004 | Stergiopoulos et al. |
| 6,807,965 B1 | 10/2004 | Hickle |
| 6,809,653 B1 | 10/2004 | Mann et al. |
| 6,813,964 B1 | 11/2004 | Clark et al. |
| 6,814,547 B2 | 11/2004 | Childers |
| 6,824,528 B1 | 11/2004 | Faries |
| 6,830,558 B2 | 12/2004 | Flaherty et al. |
| 6,840,113 B2 | 1/2005 | Fukumura et al. |
| 6,846,161 B2 | 1/2005 | Kline |
| 6,852,094 B2 | 2/2005 | Beck |
| 6,852,104 B2 | 2/2005 | Blomquist |
| 6,854,338 B2 | 2/2005 | Khuri-Yakub et al. |
| 6,857,318 B1 | 2/2005 | Silber et al. |
| 6,869,425 B2 | 3/2005 | Briggs et al. |
| 6,873,268 B2 | 3/2005 | Lebel et al. |
| 6,883,376 B2 | 4/2005 | He |
| 6,885,881 B2 | 4/2005 | Leonhardt |
| 6,887,216 B2 | 5/2005 | Hochman et al. |
| 6,898,301 B2 | 5/2005 | Iwanaga |
| 6,907,361 B2 | 6/2005 | Molenaar |
| 6,907,792 B2 | 6/2005 | Ohnishi |
| 6,915,170 B2 | 7/2005 | Engleson et al. |
| 6,920,795 B2 | 7/2005 | Bischoff et al. |
| 6,923,763 B1 | 8/2005 | Kovatchev et al. |
| 6,928,338 B1 | 8/2005 | Buchser et al. |
| 6,929,619 B2 | 8/2005 | Fago et al. |
| 6,929,751 B2 | 8/2005 | Bowman |
| 6,932,114 B2 | 8/2005 | Sparks |
| 6,932,796 B2 | 8/2005 | Sage et al. |
| 6,935,192 B2 | 8/2005 | Sobek et al. |
| 6,936,029 B2 | 8/2005 | Mann et al. |
| 6,941,005 B2 | 9/2005 | Lary et al. |
| 6,942,636 B2 | 9/2005 | Holst et al. |
| 6,945,954 B2 | 9/2005 | Hochman et al. |
| 6,958,705 B2 | 10/2005 | Lebel et al. |
| 6,964,204 B2 | 11/2005 | Clark et al. |
| 6,973,374 B2 | 12/2005 | Ader |
| 6,974,437 B2 | 12/2005 | Lebel et al. |
| 6,975,922 B2 | 12/2005 | Duncan et al. |
| 6,978,779 B2 | 12/2005 | Haveri et al. |
| 6,979,326 B2 | 12/2005 | Mann et al. |
| 6,981,960 B2 | 1/2006 | Cho et al. |
| 6,984,218 B2 | 1/2006 | Nayak et al. |
| 6,985,768 B2 | 1/2006 | Hemming et al. |
| 6,985,870 B2 | 1/2006 | Martucci et al. |
| 6,986,347 B2 | 1/2006 | Hickle |
| 6,986,753 B2 | 1/2006 | Bui |
| 6,997,905 B2 | 2/2006 | Gillespie, Jr. et al. |
| 6,997,920 B2 | 2/2006 | Mann et al. |
| 7,006,005 B2 | 2/2006 | Nazarian et al. |
| 7,017,623 B2 | 3/2006 | Tribble et al. |
| 7,021,148 B2 | 4/2006 | Kuhn |
| 7,025,743 B2 | 4/2006 | Mann et al. |
| 7,029,455 B2 | 4/2006 | Flaherty |
| 7,029,456 B2 | 4/2006 | Ware et al. |
| 7,031,857 B2 | 4/2006 | Tarassenko et al. |
| 7,059,184 B2 | 6/2006 | Kanouda et al. |
| 7,060,059 B2 | 6/2006 | Keith et al. |
| 7,069,793 B2 | 7/2006 | Ishikawa et al. |
| 7,072,725 B2 | 7/2006 | Bristol et al. |
| 7,074,209 B2 | 7/2006 | Evans et al. |
| 7,080,557 B2 | 7/2006 | Adnan |
| 7,082,843 B2 | 8/2006 | Clark et al. |
| 7,087,444 B2 | 8/2006 | Wong et al. |
| 7,092,796 B2 | 8/2006 | Vanderveen |
| 7,092,797 B2 | 8/2006 | Gaines et al. |
| 7,093,502 B2 | 8/2006 | Kupnik et al. |
| 7,096,729 B2 | 8/2006 | Repko et al. |
| 7,103,419 B2 | 9/2006 | Engleson et al. |
| 7,104,763 B2 | 9/2006 | Bouton et al. |
| 7,104,769 B2 | 9/2006 | Davis |
| 7,108,680 B2 | 9/2006 | Rohr et al. |
| 7,109,878 B2 | 9/2006 | Mann et al. |
| 7,115,113 B2 | 10/2006 | Evans et al. |
| 7,117,041 B2 | 10/2006 | Engleson et al. |
| 7,137,964 B2 | 11/2006 | Flaherty |
| 7,141,037 B2 | 11/2006 | Butterfield et al. |
| 7,152,490 B1 | 12/2006 | Freund, Jr. et al. |
| 7,154,397 B2 | 12/2006 | Zerhusen et al. |
| 7,161,488 B2 | 1/2007 | Frasch |
| 7,162,290 B1 | 1/2007 | Levin |
| 7,162,927 B1 | 1/2007 | Selvan et al. |
| 7,171,277 B2 | 1/2007 | Engleson et al. |
| 7,171,992 B2 | 2/2007 | DiGianfilippo et al. |
| 7,174,789 B2 | 2/2007 | Orr et al. |

(56)    References Cited

U.S. PATENT DOCUMENTS

| | | | |
|---|---|---|---|
| 7,185,288 B2 | 2/2007 | McKeever | |
| 7,197,943 B2 | 4/2007 | Lee et al. | |
| 7,201,734 B2 | 4/2007 | Hickle | |
| 7,204,823 B2 | 4/2007 | Estes et al. | |
| 7,206,715 B2 | 4/2007 | Vanderveen et al. | |
| 7,213,009 B2 | 5/2007 | Pestotnik | |
| 7,220,240 B2 | 5/2007 | Struys et al. | |
| 7,229,430 B2 | 6/2007 | Hickle et al. | |
| 7,230,529 B2 | 6/2007 | Ketcherside | |
| 7,232,430 B2 | 6/2007 | Carlisle | |
| 7,238,164 B2 | 7/2007 | Childers et al. | |
| 7,247,154 B2 | 7/2007 | Hickle | |
| 7,253,779 B2 | 8/2007 | Greer et al. | |
| 7,254,425 B2 | 8/2007 | Lowery et al. | |
| 7,258,534 B2 | 8/2007 | Fathallah et al. | |
| 7,267,664 B2 | 9/2007 | Rizzo | |
| 7,267,665 B2 | 9/2007 | Steil et al. | |
| 7,272,529 B2 | 9/2007 | Hogan et al. | |
| 7,278,983 B2 | 10/2007 | Ireland et al. | |
| 7,291,123 B2 | 11/2007 | Baraldi et al. | |
| 7,293,461 B1 | 11/2007 | Girndt | |
| 7,294,109 B2 | 11/2007 | Lovett et al. | |
| 7,296,482 B2 | 11/2007 | Schaffer et al. | |
| 7,300,418 B2 | 11/2007 | Zaleski | |
| 7,305,883 B2 | 12/2007 | Khuri-Yakub et al. | |
| 7,327,273 B2 | 2/2008 | Hung et al. | |
| D563,986 S | 3/2008 | Lettau | |
| 7,338,470 B2 | 3/2008 | Katz | |
| 7,343,224 B2 | 3/2008 | DiGianfilippo et al. | |
| 7,347,836 B2 | 3/2008 | Peterson et al. | |
| 7,347,854 B2 | 3/2008 | Shelton et al. | |
| 7,354,420 B2 | 4/2008 | Steil et al. | |
| 7,356,382 B2 | 4/2008 | Vanderveen | |
| 7,360,999 B2 | 4/2008 | Nelson et al. | |
| 7,364,562 B2 | 4/2008 | Braig et al. | |
| 7,367,942 B2 | 5/2008 | Grage et al. | |
| 7,369,948 B1 | 5/2008 | Ferenczi et al. | |
| 7,384,410 B2 | 6/2008 | Eggers et al. | |
| 7,397,166 B1 | 7/2008 | Morgan et al. | |
| 7,398,183 B2 | 7/2008 | Holland et al. | |
| 7,399,277 B2 | 7/2008 | Saidara et al. | |
| 7,402,153 B2 | 7/2008 | Steil et al. | |
| 7,402,154 B2 | 7/2008 | Mendez | |
| 7,407,489 B2 | 8/2008 | Mendez | |
| 7,414,534 B1 | 8/2008 | Kroll et al. | |
| 7,415,895 B2 | 8/2008 | Kurisaki et al. | |
| 7,426,443 B2 | 9/2008 | Simon | |
| 7,430,675 B2 | 9/2008 | Lee et al. | |
| 7,447,566 B2 | 11/2008 | Knauper et al. | |
| 7,447,643 B1 | 11/2008 | Olson | |
| 7,452,190 B2 | 11/2008 | Bouton et al. | |
| 7,454,314 B2 | 11/2008 | Holland et al. | |
| 7,471,994 B2 | 12/2008 | Ford et al. | |
| 7,477,997 B2 | 1/2009 | Kaplit | |
| 7,482,818 B2 | 1/2009 | Greenwald et al. | |
| 7,483,756 B2 | 1/2009 | Engleson et al. | |
| 7,490,021 B2 | 2/2009 | Holland et al. | |
| 7,491,187 B2 | 2/2009 | Van Den Berghe et al. | |
| 7,503,903 B2 | 3/2009 | Carlisle et al. | |
| 7,517,332 B2 | 4/2009 | Tonelli et al. | |
| 7,523,401 B1 | 4/2009 | Aldridge | |
| D593,125 S | 5/2009 | Danton | |
| 7,545,075 B2 | 6/2009 | Huang et al. | |
| D596,195 S | 7/2009 | Wall | |
| 7,556,616 B2 | 7/2009 | Fathallah et al. | |
| 7,561,986 B2 | 7/2009 | Vanderveen et al. | |
| 7,571,024 B2 | 8/2009 | Duncan et al. | |
| 7,605,730 B2 | 10/2009 | Tomioka et al. | |
| 7,614,310 B2 | 11/2009 | Konzelmann | |
| 7,645,258 B2 | 1/2010 | White et al. | |
| 7,654,127 B2 | 2/2010 | Krulevitch et al. | |
| 7,657,443 B2 | 2/2010 | Crass | |
| 7,668,731 B2 | 2/2010 | Martucci et al. | |
| 7,678,048 B1 | 3/2010 | Urbano et al. | |
| 7,693,697 B2 | 4/2010 | Westenskow et al. | |
| 7,699,806 B2 | 4/2010 | Ware et al. | |
| 7,705,727 B2 | 4/2010 | Pestotnik | |
| D617,807 S | 6/2010 | Christie | |
| 7,726,179 B2 * | 6/2010 | Muller | F04B 13/00 |
| | | | 73/37 |
| D621,845 S | 8/2010 | Anzures | |
| 7,766,873 B2 | 8/2010 | Moberg et al. | |
| 7,775,126 B2 | 8/2010 | Eckhardt | |
| 7,775,127 B2 | 8/2010 | Wade | |
| 7,785,284 B2 | 8/2010 | Baralsi et al. | |
| 7,785,313 B2 | 8/2010 | Mastrototaro | |
| 7,786,909 B2 | 8/2010 | Udupa et al. | |
| 7,806,886 B2 | 10/2010 | Kanderian, Jr. et al. | |
| 7,826,981 B2 | 11/2010 | Goode, Jr. et al. | |
| 7,847,276 B2 | 12/2010 | Carlisle | |
| 7,860,583 B2 | 12/2010 | Condurso et al. | |
| 7,871,394 B2 | 1/2011 | Halbert et al. | |
| 7,876,443 B2 | 1/2011 | Bernacki | |
| 7,895,053 B2 | 2/2011 | Holland et al. | |
| 7,895,882 B2 | 3/2011 | Carlisle | |
| 7,896,834 B2 | 3/2011 | Smisson, III | |
| 7,896,842 B2 | 3/2011 | Palmroos et al. | |
| 7,905,710 B2 | 3/2011 | Wang et al. | |
| 7,933,780 B2 | 4/2011 | de la Huerga | |
| 7,938,817 B2 | 5/2011 | Gelfand et al. | |
| 7,945,452 B2 | 5/2011 | Fathallah et al. | |
| D642,195 S | 7/2011 | Marks | |
| 7,976,508 B2 | 7/2011 | Hoag | |
| 7,981,073 B2 | 7/2011 | Mollstam | |
| 7,981,082 B2 | 7/2011 | Wang et al. | |
| 7,998,134 B2 | 8/2011 | Fangrow | |
| 8,002,736 B2 | 8/2011 | Patrick et al. | |
| 8,034,020 B2 | 10/2011 | Dewey | |
| 8,038,593 B2 | 10/2011 | Friedman et al. | |
| 8,065,161 B2 | 11/2011 | Howard et al. | |
| 8,067,760 B2 | 11/2011 | Carlisle | |
| 8,075,514 B2 | 12/2011 | Butterfield et al. | |
| 8,075,546 B2 | 12/2011 | Carlisle et al. | |
| 8,078,983 B2 | 12/2011 | Davis et al. | |
| 8,121,857 B2 | 2/2012 | Galasso et al. | |
| 8,149,131 B2 | 4/2012 | Blomquist | |
| D659,709 S | 5/2012 | Eby | |
| 8,175,668 B1 | 5/2012 | Nabutovsky et al. | |
| 8,177,739 B2 | 5/2012 | Cartledge et al. | |
| 8,180,440 B2 | 5/2012 | McCombie et al. | |
| 8,185,322 B2 | 5/2012 | Schroeder et al. | |
| 8,197,444 B1 | 6/2012 | Bazargan et al. | |
| 8,219,413 B2 | 7/2012 | Martinez et al. | |
| 8,221,395 B2 | 7/2012 | Shelton et al. | |
| 8,226,597 B2 | 7/2012 | Jacobson et al. | |
| 8,231,578 B2 | 7/2012 | Fathallah et al. | |
| 8,234,128 B2 | 7/2012 | Martucci et al. | |
| D667,452 S | 9/2012 | Wujcik | |
| D667,840 S | 9/2012 | Anzures | |
| 8,271,106 B2 | 9/2012 | Wehba et al. | |
| 8,287,514 B2 | 10/2012 | Miller et al. | |
| 8,291,337 B2 | 10/2012 | Gannin et al. | |
| 8,313,308 B2 | 11/2012 | Lawless et al. | |
| 8,317,698 B2 | 11/2012 | Lowery | |
| 8,317,750 B2 | 11/2012 | Ware et al. | |
| 8,317,752 B2 | 11/2012 | Cozmi et al. | |
| 8,318,094 B1 | 11/2012 | Bayandorian et al. | |
| 8,340,792 B2 | 12/2012 | Condurso et al. | |
| 8,347,731 B2 | 1/2013 | Genosar | |
| 8,359,338 B2 | 1/2013 | Butterfield et al. | |
| 8,361,021 B2 | 1/2013 | Wang et al. | |
| 8,378,837 B2 | 2/2013 | Wang et al. | |
| 8,388,598 B2 | 3/2013 | Steinkogler | |
| 8,398,616 B2 | 3/2013 | Budiman | |
| 8,403,908 B2 | 3/2013 | Jacobson et al. | |
| D679,727 S | 4/2013 | Abratowski | |
| 8,409,164 B2 | 4/2013 | Fangrow | |
| 8,449,524 B2 | 5/2013 | Braig et al. | |
| 8,469,942 B2 | 6/2013 | Kow et al. | |
| 8,477,307 B1 | 7/2013 | Yufa et al. | |
| 8,494,879 B2 | 7/2013 | Davis et al. | |
| 8,504,179 B2 | 8/2013 | Blomquist | |
| 8,506,552 B2 | 8/2013 | Rebours | |
| 8,517,990 B2 | 8/2013 | Teel et al. | |

(56)      References Cited

U.S. PATENT DOCUMENTS

| | | | |
|---|---|---|---|
| 8,518,021 B2 | 8/2013 | Stewart et al. |
| 8,522,832 B2 | 9/2013 | Lopez et al. |
| 8,523,797 B2 | 9/2013 | Lowery et al. |
| 8,539,812 B2 | 9/2013 | Stringham et al. |
| 8,543,416 B2 | 9/2013 | Palmroos et al. |
| 8,577,692 B2 | 11/2013 | Silkaitis et al. |
| 8,622,990 B2 | 1/2014 | Estes et al. |
| 8,630,722 B2 | 1/2014 | Condurso et al. |
| 8,665,214 B2 | 3/2014 | Forutanpour et al. |
| 8,666,769 B2 | 3/2014 | Butler et al. |
| 8,700,421 B2 | 4/2014 | Feng et al. |
| 8,706,233 B2 | 4/2014 | Su et al. |
| D705,260 S | 5/2014 | Gerssen |
| 8,721,584 B2 | 5/2014 | Braithwaite et al. |
| 8,728,020 B2 | 5/2014 | Caleffi et al. |
| D706,294 S | 6/2014 | Jewitt |
| 8,758,306 B2 | 6/2014 | Lopez et al. |
| 8,761,906 B2 | 6/2014 | Condurso et al. |
| D709,091 S | 7/2014 | Kwon |
| 8,768,719 B2 | 7/2014 | Wehba et al. |
| 8,771,251 B2 | 7/2014 | Ruchti et al. |
| 8,792,981 B2 | 7/2014 | Yudovsky et al. |
| D711,916 S | 8/2014 | Matas |
| D712,926 S | 9/2014 | Meegan |
| D713,417 S | 9/2014 | Daniel |
| D713,418 S | 9/2014 | Yang |
| D713,420 S | 9/2014 | Dallmeyer |
| 8,821,432 B2 | 9/2014 | Unverdorben |
| 8,823,382 B2 | 9/2014 | Rondoni et al. |
| 8,823,528 B2 | 9/2014 | Blomquist |
| 8,857,269 B2 | 10/2014 | Johnson et al. |
| 8,858,185 B2 | 10/2014 | Johnson et al. |
| 8,905,965 B2 | 12/2014 | Mandro et al. |
| D721,385 S | 1/2015 | Barling |
| 8,948,734 B2 | 2/2015 | Vaglio |
| 8,964,185 B1 | 2/2015 | Luo et al. |
| 9,005,150 B2 | 4/2015 | Ware et al. |
| 9,026,370 B2 | 5/2015 | Rubalcaba et al. |
| 9,084,855 B2 | 7/2015 | Ware et al. |
| 9,114,217 B2 | 8/2015 | Sur et al. |
| 9,134,735 B2 | 9/2015 | Lowery et al. |
| 9,134,736 B2 | 9/2015 | Lowery et al. |
| 9,138,526 B2 | 9/2015 | Ware et al. |
| D742,413 S | 11/2015 | Torres |
| D742,414 S | 11/2015 | Brunner |
| D742,415 S | 11/2015 | Cahill |
| D743,414 S | 11/2015 | Uno |
| 9,190,010 B2 | 11/2015 | Vik et al. |
| D747,339 S | 1/2016 | Cohen |
| 9,240,002 B2 | 1/2016 | Hume et al. |
| D750,099 S | 2/2016 | Kadosh |
| 9,272,089 B2 | 3/2016 | Jacobson et al. |
| 9,316,216 B1 | 4/2016 | Cook et al. |
| D757,099 S | 5/2016 | Seo |
| 9,333,291 B2 | 5/2016 | Jacobson et al. |
| D758,379 S | 6/2016 | Kadosh |
| D759,036 S | 6/2016 | Evanes |
| D760,238 S | 6/2016 | Suarez |
| D760,248 S | 6/2016 | Smith |
| D760,295 S | 6/2016 | Smith |
| D760,788 S | 7/2016 | Cho |
| D761,820 S | 7/2016 | Lee |
| D762,238 S | 7/2016 | Day |
| 9,381,296 B2 | 7/2016 | Arrizza et al. |
| 9,393,362 B2 | 7/2016 | Cozmi et al. |
| D764,538 S | 8/2016 | Lee |
| 9,468,718 B2 | 10/2016 | Hung et al. |
| 9,498,583 B2 | 11/2016 | Sur et al. |
| D773,519 S | 12/2016 | Hurley |
| D777,205 S | 1/2017 | Orr |
| 9,545,475 B2 | 1/2017 | Borges et al. |
| 9,545,476 B2 | 1/2017 | Qi et al. |
| D779,537 S | 2/2017 | Wingate-Whyte |
| D781,874 S | 3/2017 | Dunn |
| D782,535 S | 3/2017 | Menz |
| 9,707,341 B2 | 7/2017 | Dumas, III et al. |
| 9,764,087 B2 | 9/2017 | Peterfreund et al. |
| 9,773,330 B1 | 9/2017 | Douglas |
| D803,881 S | 11/2017 | Hurley |
| D806,109 S | 12/2017 | Day |
| 9,852,265 B1 | 12/2017 | Treacy et al. |
| D809,006 S | 1/2018 | Mehta |
| 9,883,987 B2 | 2/2018 | Lopez et al. |
| 9,943,269 B2 | 4/2018 | Muhsin et al. |
| 9,995,611 B2 | 6/2018 | Ruchti et al. |
| 10,002,496 B2 | 6/2018 | Humphrey |
| 10,022,498 B2 | 7/2018 | Ruchti et al. |
| 10,046,112 B2 | 8/2018 | Oruklu et al. |
| D827,665 S | 9/2018 | Segars |
| 10,089,055 B1 | 10/2018 | Fryman |
| 10,099,009 B1 | 10/2018 | Anderson et al. |
| 10,166,328 B2 | 1/2019 | Oruklu et al. |
| 10,241,626 B2 | 3/2019 | Miyazawa |
| 10,297,350 B2 | 5/2019 | Duke et al. |
| 10,342,917 B2 | 7/2019 | Shubinsky et al. |
| 10,430,761 B2 | 10/2019 | Hume et al. |
| D865,777 S | 11/2019 | Kovács |
| 10,463,788 B2 | 11/2019 | Day |
| 10,549,248 B2 | 2/2020 | Brown et al. |
| 10,578,474 B2 | 3/2020 | Ruchti et al. |
| 10,596,316 B2 | 3/2020 | Dumas, III et al. |
| 10,635,784 B2 | 4/2020 | Rubalcaba, Jr. et al. |
| 10,656,894 B2 | 5/2020 | Fryman |
| 10,682,102 B2 | 6/2020 | Declerck |
| 10,709,885 B2 | 7/2020 | Janders et al. |
| D898,055 S | 10/2020 | Connolly |
| 10,850,024 B2 | 12/2020 | Day et al. |
| 10,874,793 B2 | 12/2020 | Oruklu et al. |
| 11,004,035 B2 | 5/2021 | Hume et al. |
| 11,007,119 B2 | 5/2021 | Lopez et al. |
| D922,432 S | 6/2021 | Kataoka et al. |
| D923,050 S | 6/2021 | Kataoka et al. |
| 11,029,911 B2 | 6/2021 | Fryman |
| D926,201 S | 7/2021 | Bryant et al. |
| D926,224 S | 7/2021 | Hummel |
| D928,813 S | 8/2021 | Nurutdinov et al. |
| D928,840 S | 8/2021 | Amit et al. |
| 11,090,431 B2 | 8/2021 | Dumas, III et al. |
| D931,884 S | 9/2021 | Bryant et al. |
| D931,892 S | 9/2021 | Nurutdinov |
| D934,282 S | 10/2021 | Clymer |
| 11,135,360 B1 | 10/2021 | Jacobson et al. |
| 11,219,715 B2 | 1/2022 | Gray et al. |
| 11,246,985 B2 | 2/2022 | Gylland et al. |
| D946,608 S | 3/2022 | Higuchi |
| 11,278,671 B2 | 3/2022 | Cavendish, Jr. et al. |
| 11,298,456 B2 | 4/2022 | Shubinsky et al. |
| 11,324,888 B2 | 5/2022 | Shubinsky et al. |
| 11,344,668 B2 | 5/2022 | Sileika et al. |
| 11,344,673 B2 | 5/2022 | Lindo et al. |
| 11,376,361 B2 | 7/2022 | Ruchti et al. |
| 11,378,430 B2 | 7/2022 | Ruchti et al. |
| 11,395,875 B2 | 7/2022 | Rubalcaba, Jr. et al. |
| 11,433,177 B2 | 9/2022 | Oruklu et al. |
| 11,439,570 B2 | 9/2022 | Lopez et al. |
| 11,596,737 B2 | 3/2023 | Dumas, III et al. |
| 11,599,854 B2 | 3/2023 | Hume et al. |
| 11,623,042 B2 | 4/2023 | Day |
| 11,868,161 B2 | 1/2024 | Fryman |
| 11,883,361 B2 | 1/2024 | Janssen |
| D1,017,633 S | 3/2024 | Chung |
| D1,018,593 S | 3/2024 | Chiah |
| 11,933,650 B2 | 3/2024 | Ruchti et al. |
| D1,021,917 S | 4/2024 | Ceniceroz |
| D1,023,027 S | 4/2024 | Slettnes |
| D1,024,096 S | 4/2024 | Zhong |
| 11,972,395 B2 | 4/2024 | Hume et al. |
| D1,027,974 S | 5/2024 | Correy |
| 12,048,831 B2 | 7/2024 | Oruklu et al. |
| 12,059,551 B2 | 8/2024 | Dumas, III et al. |
| 12,076,531 B2 | 9/2024 | Shubinsky et al. |
| 12,083,310 B2 | 9/2024 | Shubinsky et al. |
| 12,115,337 B2 | 10/2024 | Day et al. |
| 12,201,811 B2 | 1/2025 | Gylland et al. |

(56) References Cited

U.S. PATENT DOCUMENTS

| | | | |
|---|---|---|---|
| 12,310,921 | B2 | 5/2025 | Janssen |
| 2001/0007636 | A1 | 7/2001 | Butterfield |
| 2001/0014769 | A1 | 8/2001 | Bufe et al. |
| 2001/0015099 | A1 | 8/2001 | Blaine |
| 2001/0016056 | A1 | 8/2001 | Westphal et al. |
| 2001/0032099 | A1 | 10/2001 | Joao |
| 2001/0037060 | A1 | 11/2001 | Thompson et al. |
| 2001/0041869 | A1 | 11/2001 | Causey et al. |
| 2001/0044731 | A1 | 11/2001 | Coffman et al. |
| 2002/0003892 | A1 | 1/2002 | Iwanaga |
| 2002/0007116 | A1 | 1/2002 | Zatezalo et al. |
| 2002/0013545 | A1 | 1/2002 | Soltanpour et al. |
| 2002/0013551 | A1 | 1/2002 | Zaitsu et al. |
| 2002/0015018 | A1 | 2/2002 | Shimazu et al. |
| 2002/0018720 | A1 | 2/2002 | Carlisle et al. |
| 2002/0029776 | A1 | 3/2002 | Blomquist |
| 2002/0031838 | A1 | 3/2002 | Meinhart et al. |
| 2002/0032583 | A1 | 3/2002 | Joao |
| 2002/0038392 | A1 | 3/2002 | De La Huerga |
| 2002/0040208 | A1 | 4/2002 | Flaherty et al. |
| 2002/0044059 | A1 | 4/2002 | Reeder et al. |
| 2002/0045806 | A1 | 4/2002 | Baker, Jr. et al. |
| 2002/0082728 | A1 | 6/2002 | Mueller et al. |
| 2002/0083771 | A1 | 7/2002 | Khuri-Yakub et al. |
| 2002/0085952 | A1 | 7/2002 | Ellingboe et al. |
| 2002/0087115 | A1 | 7/2002 | Hartlaub |
| 2002/0093641 | A1 | 7/2002 | Ortyn et al. |
| 2002/0095486 | A1 | 7/2002 | Bahl |
| 2002/0099282 | A1 | 7/2002 | Knobbe et al. |
| 2002/0099334 | A1 | 7/2002 | Hanson et al. |
| 2002/0143580 | A1 | 10/2002 | Bristol et al. |
| 2002/0147389 | A1 | 10/2002 | Cavallaro et al. |
| 2002/0152239 | A1 | 10/2002 | Bautista-Lloyd et al. |
| 2002/0158919 | A1 | 10/2002 | Nacey |
| 2002/0168278 | A1 | 11/2002 | Jeon et al. |
| 2002/0169636 | A1 | 11/2002 | Eggers et al. |
| 2002/0173703 | A1 | 11/2002 | Lebel et al. |
| 2002/0183693 | A1 | 12/2002 | Peterson et al. |
| 2003/0009244 | A1 | 1/2003 | Engleson |
| 2003/0013959 | A1 | 1/2003 | Grunwald et al. |
| 2003/0018289 | A1 | 1/2003 | Ng et al. |
| 2003/0018308 | A1 | 1/2003 | Tsai |
| 2003/0025602 | A1 | 2/2003 | Medema et al. |
| 2003/0028082 | A1 | 2/2003 | Thompson |
| 2003/0030001 | A1 | 2/2003 | Cooper et al. |
| 2003/0045840 | A1 | 3/2003 | Burko |
| 2003/0050621 | A1 | 3/2003 | Lebel et al. |
| 2003/0052787 | A1 | 3/2003 | Zerhusen et al. |
| 2003/0060688 | A1 | 3/2003 | Ciarniello et al. |
| 2003/0060765 | A1 | 3/2003 | Campbell et al. |
| 2003/0065537 | A1 | 4/2003 | Evans |
| 2003/0065589 | A1 | 4/2003 | Giacchetti |
| 2003/0073954 | A1 | 4/2003 | Moberg et al. |
| 2003/0079746 | A1 | 5/2003 | Hickle |
| 2003/0083583 | A1 | 5/2003 | Kovtun et al. |
| 2003/0091442 | A1 | 5/2003 | Bush et al. |
| 2003/0104982 | A1 | 6/2003 | Wittmann et al. |
| 2003/0106553 | A1 | 6/2003 | Vanderveen |
| 2003/0114836 | A1 | 6/2003 | Estes et al. |
| 2003/0117296 | A1 | 6/2003 | Seely |
| 2003/0125662 | A1 | 7/2003 | Bui |
| 2003/0130616 | A1 | 7/2003 | Steil |
| 2003/0135087 | A1 | 7/2003 | Hickle et al. |
| 2003/0135388 | A1 | 7/2003 | Martucci et al. |
| 2003/0136193 | A1 | 7/2003 | Fujimoto |
| 2003/0139701 | A1 | 7/2003 | White et al. |
| 2003/0140928 | A1 | 7/2003 | Bui et al. |
| 2003/0140929 | A1 | 7/2003 | Wilkes et al. |
| 2003/0141981 | A1 | 7/2003 | Bui et al. |
| 2003/0143746 | A1 | 7/2003 | Sage, Jr. |
| 2003/0144878 | A1 | 7/2003 | Wilkes et al. |
| 2003/0158508 | A1 | 8/2003 | DiGianfilippo |
| 2003/0159741 | A1 | 8/2003 | Sparks |
| 2003/0160683 | A1 | 8/2003 | Blomquist |
| 2003/0163789 | A1 | 8/2003 | Blomquist |
| 2003/0173408 | A1 | 9/2003 | Mosher, Jr. et al. |
| 2003/0186833 | A1 | 10/2003 | Huff et al. |
| 2003/0187338 | A1 | 10/2003 | Say et al. |
| 2003/0194328 | A1 | 10/2003 | Bryant et al. |
| 2003/0200116 | A1 | 10/2003 | Forrester |
| 2003/0204274 | A1 | 10/2003 | Ullestad et al. |
| 2003/0204416 | A1 | 10/2003 | Acharya |
| 2003/0212364 | A1 | 11/2003 | Mann et al. |
| 2003/0212379 | A1 | 11/2003 | Bylund et al. |
| 2003/0216682 | A1 | 11/2003 | Junker |
| 2003/0217962 | A1 | 11/2003 | Childers et al. |
| 2003/0233071 | A1 | 12/2003 | Gillespie, Jr. et al. |
| 2004/0030277 | A1 | 2/2004 | O'Mahony et al. |
| 2004/0047736 | A1 | 3/2004 | Nose et al. |
| 2004/0057226 | A1 | 3/2004 | Berthou et al. |
| 2004/0064342 | A1 | 4/2004 | Browne et al. |
| 2004/0073125 | A1 | 4/2004 | Lovett et al. |
| 2004/0073161 | A1 | 4/2004 | Tachibana |
| 2004/0077996 | A1 | 4/2004 | Jasperson et al. |
| 2004/0082908 | A1 | 4/2004 | Whitehurst |
| 2004/0082918 | A1 | 4/2004 | Evans et al. |
| 2004/0104271 | A1 | 6/2004 | Martucci et al. |
| 2004/0119753 | A1 | 6/2004 | Zencke |
| 2004/0120825 | A1 | 6/2004 | Bouton et al. |
| 2004/0128162 | A1 | 7/2004 | Schlotterbeck et al. |
| 2004/0128163 | A1 | 7/2004 | Goodman et al. |
| 2004/0130573 | A1 | 7/2004 | Konuma |
| 2004/0133166 | A1 | 7/2004 | Moberg et al. |
| 2004/0145114 | A1 | 7/2004 | Ippolito et al. |
| 2004/0147034 | A1 | 7/2004 | Gore et al. |
| 2004/0149823 | A1 | 8/2004 | Aptekar |
| 2004/0152970 | A1 | 8/2004 | Hunter et al. |
| 2004/0158193 | A1 | 8/2004 | Bui et al. |
| 2004/0167464 | A1 | 8/2004 | Ireland et al. |
| 2004/0167465 | A1 | 8/2004 | Kohler |
| 2004/0167804 | A1 | 8/2004 | Simpson |
| 2004/0172222 | A1 | 9/2004 | Simpson et al. |
| 2004/0172283 | A1 | 9/2004 | Vanderveen |
| 2004/0172289 | A1 | 9/2004 | Kozic et al. |
| 2004/0172301 | A1 | 9/2004 | Mihai et al. |
| 2004/0172302 | A1 | 9/2004 | Martucci et al. |
| 2004/0176984 | A1 | 9/2004 | White et al. |
| 2004/0181314 | A1 | 9/2004 | Zaleski |
| 2004/0193025 | A1 | 9/2004 | Steil et al. |
| 2004/0193325 | A1 | 9/2004 | Bonderud |
| 2004/0193328 | A1 | 9/2004 | Butterfield et al. |
| 2004/0204638 | A1 | 10/2004 | Diab et al. |
| 2004/0204673 | A1 | 10/2004 | Flaherty et al. |
| 2004/0220517 | A1 | 11/2004 | Starkweather et al. |
| 2004/0225252 | A1 | 11/2004 | Gillespie et al. |
| 2004/0225409 | A1 | 11/2004 | Duncan et al. |
| 2004/0232219 | A1 | 11/2004 | Fowler |
| 2004/0253123 | A1 | 12/2004 | Xie et al. |
| 2004/0254434 | A1 | 12/2004 | Goodnow et al. |
| 2004/0254513 | A1 | 12/2004 | Shang et al. |
| 2005/0021006 | A1 | 1/2005 | Tonnies |
| 2005/0021297 | A1 | 1/2005 | Hartlaub |
| 2005/0022274 | A1 | 1/2005 | Campbell et al. |
| 2005/0038680 | A1 | 2/2005 | McMahon |
| 2005/0055242 | A1 | 3/2005 | Bello et al. |
| 2005/0055244 | A1 | 3/2005 | Mullan et al. |
| 2005/0065465 | A1 | 3/2005 | Lebel et al. |
| 2005/0075544 | A1 | 4/2005 | Shapiro et al. |
| 2005/0096593 | A1 | 5/2005 | Pope et al. |
| 2005/0099624 | A1 | 5/2005 | Staehr |
| 2005/0107923 | A1 | 5/2005 | Vanderveen |
| 2005/0108057 | A1 | 5/2005 | Cohen et al. |
| 2005/0119597 | A1 | 6/2005 | O'Mahony et al. |
| 2005/0119914 | A1 | 6/2005 | Batch |
| 2005/0131739 | A1 | 6/2005 | Rabinowitz et al. |
| 2005/0137522 | A1 | 6/2005 | Aoki |
| 2005/0137653 | A1 | 6/2005 | Friedman et al. |
| 2005/0143864 | A1 | 6/2005 | Blomquist |
| 2005/0145010 | A1 | 7/2005 | Vanderveen et al. |
| 2005/0171503 | A1 | 8/2005 | Van Den Berghe et al. |
| 2005/0171815 | A1 | 8/2005 | Vanderveen |
| 2005/0177045 | A1 | 8/2005 | Degertekin et al. |
| 2005/0177096 | A1 | 8/2005 | Bollish et al. |
| 2005/0182306 | A1 | 8/2005 | Sloan |

(56)  References Cited

U.S. PATENT DOCUMENTS

| | | |
|---|---|---|
| 2005/0182355 A1 | 8/2005 | Bui |
| 2005/0182366 A1 | 8/2005 | Vogt et al. |
| 2005/0187515 A1 | 8/2005 | Varrichio et al. |
| 2005/0192529 A1 | 9/2005 | Butterfield et al. |
| 2005/0192557 A1 | 9/2005 | Brauker et al. |
| 2005/0197554 A1 | 9/2005 | Polcha |
| 2005/0197621 A1 | 9/2005 | Poulsen et al. |
| 2005/0197649 A1 | 9/2005 | Shelton et al. |
| 2005/0204828 A1 | 9/2005 | Lee et al. |
| 2005/0209563 A1 | 9/2005 | Hopping et al. |
| 2005/0209793 A1 | 9/2005 | Yamada |
| 2005/0224083 A1 | 10/2005 | Crass |
| 2005/0235732 A1 | 10/2005 | Rush |
| 2005/0238506 A1 | 10/2005 | Mescher et al. |
| 2005/0240305 A1 | 10/2005 | Bogash et al. |
| 2005/0273059 A1 | 12/2005 | Mernoe et al. |
| 2005/0277890 A1 | 12/2005 | Stewart et al. |
| 2005/0279419 A1 | 12/2005 | Tribble et al. |
| 2006/0002799 A1 | 1/2006 | Schann et al. |
| 2006/0009727 A1 | 1/2006 | O'Mahony et al. |
| 2006/0009734 A1 | 1/2006 | Martin |
| 2006/0026205 A1 | 2/2006 | Butterfield et al. |
| 2006/0042633 A1 | 3/2006 | Bishop et al. |
| 2006/0047270 A1 | 3/2006 | Shelton |
| 2006/0047538 A1 | 3/2006 | Condurso et al. |
| 2006/0053036 A1 | 3/2006 | Coffman et al. |
| 2006/0064020 A1 | 3/2006 | Burnes et al. |
| 2006/0064053 A1 | 3/2006 | Bollish et al. |
| 2006/0079768 A1 | 4/2006 | Small et al. |
| 2006/0079831 A1 | 4/2006 | Gilbert |
| 2006/0100746 A1 | 5/2006 | Leibner-Druska |
| 2006/0100907 A1 | 5/2006 | Holland et al. |
| 2006/0106649 A1 | 5/2006 | Eggers et al. |
| 2006/0116639 A1 | 6/2006 | Russell |
| 2006/0117856 A1 | 6/2006 | Orr et al. |
| 2006/0117867 A1 | 6/2006 | Froehlich et al. |
| 2006/0122867 A1 | 6/2006 | Eggers et al. |
| 2006/0135939 A1 | 6/2006 | Brown |
| 2006/0135940 A1 | 6/2006 | Joshi |
| 2006/0136095 A1 | 6/2006 | Rob et al. |
| 2006/0136271 A1 | 6/2006 | Eggers et al. |
| 2006/0140798 A1 | 6/2006 | Kutsuzawa |
| 2006/0143051 A1 | 6/2006 | Eggers et al. |
| 2006/0173260 A1 | 8/2006 | Gaoni et al. |
| 2006/0173406 A1 | 8/2006 | Hayes et al. |
| 2006/0181695 A1 | 8/2006 | Sage, Jr. |
| 2006/0187069 A1 | 8/2006 | Duan |
| 2006/0190302 A1 | 8/2006 | Eggers et al. |
| 2006/0195022 A1 | 8/2006 | Trepagnier et al. |
| 2006/0200007 A1 | 9/2006 | Brockway et al. |
| 2006/0200369 A1 | 9/2006 | Batch et al. |
| 2006/0211404 A1 | 9/2006 | Cromp et al. |
| 2006/0224140 A1 | 10/2006 | Junker |
| 2006/0224141 A1 | 10/2006 | Rush et al. |
| 2006/0224181 A1 | 10/2006 | McEwen et al. |
| 2006/0226088 A1 | 10/2006 | Robinson et al. |
| 2006/0226089 A1 | 10/2006 | Robinson et al. |
| 2006/0226090 A1 | 10/2006 | Robinson et al. |
| 2006/0229551 A1 | 10/2006 | Martinez et al. |
| 2006/0229918 A1 | 10/2006 | Fotsch et al. |
| 2006/0235353 A1 | 10/2006 | Gelfand et al. |
| 2006/0255149 A1 | 11/2006 | Retter et al. |
| 2006/0258985 A1 | 11/2006 | Russell |
| 2006/0260416 A1 | 11/2006 | Sage et al. |
| 2006/0264895 A1 | 11/2006 | Flanders |
| 2006/0266128 A1 | 11/2006 | Clark et al. |
| 2006/0270971 A1 | 11/2006 | Gelfand et al. |
| 2006/0271286 A1 | 11/2006 | Rosenberg |
| 2006/0272421 A1 | 12/2006 | Frinak et al. |
| 2006/0275142 A1 | 12/2006 | Bouton et al. |
| 2007/0015972 A1 | 1/2007 | Wang et al. |
| 2007/0036511 A1 | 2/2007 | Lundquist et al. |
| 2007/0060796 A1 | 3/2007 | Kim |
| 2007/0060869 A1 | 3/2007 | Tolle et al. |
| 2007/0060871 A1 | 3/2007 | Istoc |
| 2007/0060872 A1 | 3/2007 | Hall et al. |
| 2007/0060874 A1 | 3/2007 | Nesbitt et al. |
| 2007/0062250 A1 | 3/2007 | Krulevitch et al. |
| 2007/0065363 A1 | 3/2007 | Dalal et al. |
| 2007/0078314 A1 | 4/2007 | Grounsell |
| 2007/0083152 A1 | 4/2007 | Williams, Jr. et al. |
| 2007/0084286 A1 | 4/2007 | Ajay et al. |
| 2007/0084288 A1 | 4/2007 | Thomas et al. |
| 2007/0088271 A1 | 4/2007 | Richards |
| 2007/0088333 A1 | 4/2007 | Levin et al. |
| 2007/0093753 A1 | 4/2007 | Krulevitcvh et al. |
| 2007/0094045 A1 | 4/2007 | Cobbs et al. |
| 2007/0094046 A1 | 4/2007 | Cobbs et al. |
| 2007/0100222 A1 | 5/2007 | Mastrototaro et al. |
| 2007/0100665 A1 | 5/2007 | Brown |
| 2007/0112298 A1 | 5/2007 | Mueller et al. |
| 2007/0118405 A1 | 5/2007 | Campbell et al. |
| 2007/0129618 A1 | 6/2007 | Goldberger et al. |
| 2007/0142822 A1 | 6/2007 | Remde |
| 2007/0156452 A1 | 7/2007 | Batch |
| 2007/0156456 A1 | 7/2007 | McGillin et al. |
| 2007/0179436 A1 | 8/2007 | Braig et al. |
| 2007/0180916 A1 | 8/2007 | Tian et al. |
| 2007/0191770 A1 | 8/2007 | Moberg et al. |
| 2007/0191817 A1 | 8/2007 | Martin |
| 2007/0197963 A1 | 8/2007 | Griffiths et al. |
| 2007/0214003 A1 | 9/2007 | Holland et al. |
| 2007/0215545 A1 | 9/2007 | Bissler et al. |
| 2007/0233035 A1 | 10/2007 | Wehba et al. |
| 2007/0233049 A1 | 10/2007 | Wehba et al. |
| 2007/0240497 A1 | 10/2007 | Robinson et al. |
| 2007/0250339 A1 | 10/2007 | Mallett et al. |
| 2007/0255250 A1 | 11/2007 | Moberg et al. |
| 2007/0257788 A1 | 11/2007 | Carlson |
| 2007/0267945 A1 | 11/2007 | Sudol |
| 2007/0270747 A1 | 11/2007 | Remde |
| 2007/0274843 A1 | 11/2007 | Vanderveen et al. |
| 2007/0289384 A1 | 12/2007 | Sakai et al. |
| 2007/0299389 A1 | 12/2007 | Halbert et al. |
| 2008/0009684 A1 | 1/2008 | Corsetti et al. |
| 2008/0028868 A1 | 2/2008 | Konzelmann et al. |
| 2008/0033361 A1 | 2/2008 | Evans et al. |
| 2008/0039777 A1 | 2/2008 | Katz et al. |
| 2008/0048211 A1 | 2/2008 | Khuri-Yakub et al. |
| 2008/0058773 A1 | 3/2008 | John |
| 2008/0060448 A1 | 3/2008 | Wiest et al. |
| 2008/0065420 A1 | 3/2008 | Tirinato et al. |
| 2008/0071210 A1 | 3/2008 | Moubayed et al. |
| 2008/0071496 A1 | 3/2008 | Glascock |
| 2008/0071580 A1 | 3/2008 | Marcus et al. |
| 2008/0077116 A1 | 3/2008 | Dailey et al. |
| 2008/0086087 A1 | 4/2008 | Spohn et al. |
| 2008/0091466 A1 | 4/2008 | Butler et al. |
| 2008/0097288 A1 | 4/2008 | Levin et al. |
| 2008/0097289 A1 | 4/2008 | Steil et al. |
| 2008/0097317 A1 | 4/2008 | Alholm et al. |
| 2008/0098798 A1 | 5/2008 | Riley et al. |
| 2008/0119822 A1 | 5/2008 | Knauper |
| 2008/0125701 A1 | 5/2008 | Moberg et al. |
| 2008/0139907 A1 | 6/2008 | Rao et al. |
| 2008/0145249 A1 | 6/2008 | Smisson |
| 2008/0169044 A1 | 7/2008 | Osborne et al. |
| 2008/0172030 A1 | 7/2008 | Blomquist et al. |
| 2008/0184784 A1 | 8/2008 | Dam |
| 2008/0188789 A1 | 8/2008 | Galavotti et al. |
| 2008/0188796 A1 | 8/2008 | Steil et al. |
| 2008/0208484 A1 | 8/2008 | Butterfield et al. |
| 2008/0214919 A1 | 9/2008 | Harmon et al. |
| 2008/0221521 A1 | 9/2008 | Getz et al. |
| 2008/0221522 A1 | 9/2008 | Moberg et al. |
| 2008/0262469 A1 | 10/2008 | Bristol et al. |
| 2008/0269663 A1 | 10/2008 | Arnold et al. |
| 2008/0269714 A1 | 10/2008 | Mastrototaro et al. |
| 2008/0269723 A1 | 10/2008 | Mastrototaro et al. |
| 2008/0275384 A1 | 11/2008 | Mastrototaro et al. |
| 2008/0300572 A1 | 12/2008 | Rankers et al. |
| 2009/0001908 A1 | 1/2009 | Shubinsky et al. |
| 2009/0005703 A1 | 1/2009 | Fasciano |
| 2009/0006061 A1 | 1/2009 | Thukral et al. |

(56) References Cited

U.S. PATENT DOCUMENTS

| | | |
|---|---|---|
| 2009/0006129 A1 | 1/2009 | Thukral |
| 2009/0006133 A1 | 1/2009 | Weinert |
| 2009/0015824 A1 | 1/2009 | Shubinsky et al. |
| 2009/0043171 A1 | 2/2009 | Rule |
| 2009/0054743 A1 | 2/2009 | Stewart |
| 2009/0054754 A1 | 2/2009 | McMahon et al. |
| 2009/0062727 A1 | 3/2009 | Woo |
| 2009/0069743 A1 | 3/2009 | Krishnamoorthy et al. |
| 2009/0077248 A1 | 3/2009 | Castellucci et al. |
| 2009/0082676 A1 | 3/2009 | Bennison |
| 2009/0088731 A1 | 4/2009 | Campbell et al. |
| 2009/0097029 A1 | 4/2009 | Tokhtuev et al. |
| 2009/0099866 A1 | 4/2009 | Newman |
| 2009/0105636 A1 | 4/2009 | Hayter et al. |
| 2009/0112155 A1 | 4/2009 | Zhao |
| 2009/0114037 A1 | 5/2009 | Smith |
| 2009/0119330 A1 | 5/2009 | Sampath et al. |
| 2009/0124963 A1 | 5/2009 | Hogard et al. |
| 2009/0124964 A1 | 5/2009 | Leach et al. |
| 2009/0126825 A1 | 5/2009 | Eliuk et al. |
| 2009/0131861 A1 | 5/2009 | Braig et al. |
| 2009/0135196 A1 | 5/2009 | Holland et al. |
| 2009/0143726 A1 | 6/2009 | Bouton et al. |
| 2009/0144025 A1 | 6/2009 | Bouton et al. |
| 2009/0144026 A1 | 6/2009 | Bouton et al. |
| 2009/0149743 A1 | 6/2009 | Barron et al. |
| 2009/0156922 A1 | 6/2009 | Goldberger et al. |
| 2009/0156975 A1 | 6/2009 | Robinson et al. |
| 2009/0177146 A1 | 7/2009 | Nesbitt et al. |
| 2009/0177188 A1 | 7/2009 | Steinkogler |
| 2009/0177248 A1 | 7/2009 | Roberts |
| 2009/0177769 A1 | 7/2009 | Roberts |
| 2009/0178485 A1 | 7/2009 | Thomas et al. |
| 2009/0183147 A1 | 7/2009 | Davis et al. |
| 2009/0192367 A1 | 7/2009 | Braig et al. |
| 2009/0198347 A1 | 8/2009 | Kirzinger |
| 2009/0205426 A1 | 8/2009 | Balschat et al. |
| 2009/0209938 A1 | 8/2009 | Aalto-Setala |
| 2009/0209945 A1 | 8/2009 | Lobl et al. |
| 2009/0212966 A1 | 8/2009 | Panduro |
| 2009/0221890 A1 | 9/2009 | Saffer et al. |
| 2009/0223294 A1 | 9/2009 | Thomas et al. |
| 2009/0227939 A1 | 9/2009 | Memoe et al. |
| 2009/0264720 A1 | 10/2009 | Torjman et al. |
| 2009/0270810 A1 | 10/2009 | DeBelser |
| 2009/0270833 A1 | 10/2009 | DeBelser |
| 2009/0281497 A1 | 11/2009 | Kamen et al. |
| 2009/0299156 A1 | 12/2009 | Simpson et al. |
| 2010/0022988 A1 | 1/2010 | Wochner |
| 2010/0036310 A1 | 2/2010 | Hillman |
| 2010/0056992 A1 | 3/2010 | Hayter |
| 2010/0057042 A1 | 3/2010 | Hayter |
| 2010/0069892 A1 | 3/2010 | Steinbach et al. |
| 2010/0077866 A1 | 4/2010 | Graboi et al. |
| 2010/0079760 A1 | 4/2010 | Bernacki |
| 2010/0094251 A1 | 4/2010 | Estes et al. |
| 2010/0106082 A1 | 4/2010 | Zhou |
| 2010/0114027 A1 | 5/2010 | Jacobson et al. |
| 2010/0121170 A1 | 5/2010 | Rule |
| 2010/0121415 A1 | 5/2010 | Skelton et al. |
| 2010/0130933 A1 | 5/2010 | Holland et al. |
| 2010/0131434 A1 | 5/2010 | Magent et al. |
| 2010/0141460 A1 | 6/2010 | Tokhtuev et al. |
| 2010/0147081 A1 | 6/2010 | Thomas et al. |
| 2010/0152554 A1 | 6/2010 | Steine et al. |
| 2010/0160854 A1 | 6/2010 | Gauthier |
| 2010/0168535 A1 | 7/2010 | Robinson et al. |
| 2010/0177375 A1 | 7/2010 | Seyfried |
| 2010/0185142 A1 | 7/2010 | Kamen et al. |
| 2010/0185182 A1 | 7/2010 | Alme et al. |
| 2010/0198034 A1 | 8/2010 | Thomas et al. |
| 2010/0198182 A1 | 8/2010 | Lanigan et al. |
| 2010/0198183 A1 | 8/2010 | Lanigan et al. |
| 2010/0211002 A1 | 8/2010 | Davis |
| 2010/0212407 A1 | 8/2010 | Stringham et al. |
| 2010/0212675 A1 | 8/2010 | Walling et al. |
| 2010/0217154 A1 | 8/2010 | Deshmukh et al. |
| 2010/0217621 A1 | 8/2010 | Schoenberg |
| 2010/0256562 A1 | 10/2010 | Cartledge et al. |
| 2010/0271218 A1 | 10/2010 | Hoag et al. |
| 2010/0271479 A1 | 10/2010 | Heydlauf |
| 2010/0273738 A1 | 10/2010 | Valcke et al. |
| 2010/0280430 A1 | 11/2010 | Caleffi et al. |
| 2010/0292634 A1 | 11/2010 | Kircher |
| 2010/0295686 A1 | 11/2010 | Sloan et al. |
| 2010/0298765 A1 | 11/2010 | Budiman et al. |
| 2010/0312039 A1 | 12/2010 | Quirico et al. |
| 2010/0317093 A1 | 12/2010 | Turewicz et al. |
| 2010/0317952 A1 | 12/2010 | Budiman et al. |
| 2010/0318025 A1 | 12/2010 | John |
| 2011/0000560 A1 | 1/2011 | Miller et al. |
| 2011/0001605 A1 | 1/2011 | Kiani et al. |
| 2011/0004186 A1 | 1/2011 | Butterfield |
| 2011/0009797 A1 | 1/2011 | Kelly et al. |
| 2011/0028885 A1 | 2/2011 | Eggers et al. |
| 2011/0046558 A1 | 2/2011 | Gravesen et al. |
| 2011/0054311 A1 | 3/2011 | Williams et al. |
| 2011/0062703 A1 | 3/2011 | Lopez et al. |
| 2011/0064612 A1 | 3/2011 | Franzoni et al. |
| 2011/0071464 A1 | 3/2011 | Palerm |
| 2011/0071844 A1 | 3/2011 | Cannon et al. |
| 2011/0072379 A1 | 3/2011 | Gannon |
| 2011/0077480 A1 | 3/2011 | Bloom et al. |
| 2011/0078608 A1 | 3/2011 | Gannon et al. |
| 2011/0099313 A1 | 4/2011 | Bolanowski |
| 2011/0105983 A1 | 5/2011 | Kelly et al. |
| 2011/0106561 A1 | 5/2011 | Eaton, Jr. et al. |
| 2011/0107251 A1 | 5/2011 | Guaitoli et al. |
| 2011/0137241 A1 | 6/2011 | DelCastillo et al. |
| 2011/0144595 A1 | 6/2011 | Cheng |
| 2011/0152770 A1 | 6/2011 | Diperna et al. |
| 2011/0160649 A1 | 6/2011 | Pan |
| 2011/0162647 A1 | 7/2011 | Huby et al. |
| 2011/0172918 A1 | 7/2011 | Tome |
| 2011/0175728 A1 | 7/2011 | Baker, Jr. |
| 2011/0184379 A1 | 7/2011 | Van Antwerp et al. |
| 2011/0190598 A1 | 8/2011 | Shusterman |
| 2011/0190694 A1 | 8/2011 | Lanier et al. |
| 2011/0218514 A1 | 9/2011 | Rebours |
| 2011/0238032 A1 | 9/2011 | McTaggart et al. |
| 2011/0264006 A1 | 10/2011 | Ali et al. |
| 2011/0264043 A1 | 10/2011 | Kotnick et al. |
| 2011/0282321 A1 | 11/2011 | Steil et al. |
| 2011/0313390 A1 | 12/2011 | Roy et al. |
| 2011/0319728 A1 | 12/2011 | Petisce et al. |
| 2011/0320049 A1 | 12/2011 | Chossat et al. |
| 2012/0016215 A1 | 1/2012 | Condurso et al. |
| 2012/0023431 A1 | 1/2012 | Roth |
| 2012/0025995 A1 | 2/2012 | Moberg et al. |
| 2012/0059234 A1 | 3/2012 | Barrett et al. |
| 2012/0068001 A1 | 3/2012 | Pushkarsky et al. |
| 2012/0083760 A1 | 4/2012 | Ledford et al. |
| 2012/0085277 A1 | 4/2012 | Abdel-Rahman |
| 2012/0089411 A1 | 4/2012 | Srnka et al. |
| 2012/0095433 A1 | 4/2012 | Hungerford et al. |
| 2012/0116195 A1 | 5/2012 | Chaum et al. |
| 2012/0123322 A1 | 5/2012 | Scarpaci et al. |
| 2012/0143116 A1 | 6/2012 | Ware et al. |
| 2012/0180790 A1 | 7/2012 | Montgomery |
| 2012/0185267 A1 | 7/2012 | Kamen et al. |
| 2012/0191059 A1 | 7/2012 | Cummings et al. |
| 2012/0194341 A1 | 8/2012 | Peichel et al. |
| 2012/0203177 A1 | 8/2012 | Lanier |
| 2012/0222774 A1 | 9/2012 | Husnu et al. |
| 2012/0226350 A1 | 9/2012 | Rudser et al. |
| 2012/0245525 A1 | 9/2012 | Pope et al. |
| 2012/0259278 A1 | 10/2012 | Hayes et al. |
| 2012/0310204 A1 | 12/2012 | Krogh et al. |
| 2012/0323212 A1 | 12/2012 | Murphy |
| 2013/0006666 A1 | 1/2013 | Schneider |
| 2013/0009551 A1 | 1/2013 | Knapp |
| 2013/0012880 A1 | 1/2013 | Blomquist |
| 2013/0012917 A1 | 1/2013 | Miller et al. |
| 2013/0032634 A1 | 2/2013 | McKirdy |

(56) References Cited

U.S. PATENT DOCUMENTS

| | | |
|---|---|---|
| 2013/0041342 A1 | 2/2013 | Bernini et al. |
| 2013/0044111 A1 | 2/2013 | VanGilder et al. |
| 2013/0110538 A1 | 5/2013 | Butterfield et al. |
| 2013/0116649 A1 | 5/2013 | Breton et al. |
| 2013/0150766 A1 | 6/2013 | Olde et al. |
| 2013/0150821 A1 | 6/2013 | Bollish et al. |
| 2013/0173291 A1 | 7/2013 | Kelly |
| 2013/0177455 A1 | 7/2013 | Kamen et al. |
| 2013/0184676 A1 | 7/2013 | Kamen et al. |
| 2013/0197930 A1 | 8/2013 | Garibaldi et al. |
| 2013/0201482 A1 | 8/2013 | Munro |
| 2013/0218080 A1 | 8/2013 | Peterfreund et al. |
| 2013/0253430 A1 | 9/2013 | Kouyoumjian et al. |
| 2013/0253946 A1 | 9/2013 | Broselow |
| 2013/0274576 A1 | 10/2013 | Amirouche et al. |
| 2013/0281965 A1 | 10/2013 | Kamen et al. |
| 2013/0291116 A1 | 10/2013 | Homer |
| 2013/0296823 A1 | 11/2013 | Melker et al. |
| 2013/0296984 A1 | 11/2013 | Burnett et al. |
| 2013/0318158 A1 | 11/2013 | Teng et al. |
| 2013/0322201 A1 | 12/2013 | Hitchcock et al. |
| 2013/0345658 A1 | 12/2013 | Browne et al. |
| 2013/0345666 A1 | 12/2013 | Panduro et al. |
| 2014/0067425 A1 | 3/2014 | Dudar et al. |
| 2014/0132524 A1 | 5/2014 | Lee |
| 2014/0145915 A1 | 5/2014 | Ribble et al. |
| 2014/0180711 A1 | 6/2014 | Kamen et al. |
| 2014/0224829 A1 | 8/2014 | Capone et al. |
| 2014/0267563 A1 | 9/2014 | Baca et al. |
| 2014/0303591 A1 | 10/2014 | Peterfreund et al. |
| 2014/0303754 A1 | 10/2014 | Nixon et al. |
| 2015/0025453 A1 | 1/2015 | Ledford et al. |
| 2015/0033073 A1 | 1/2015 | Yang et al. |
| 2015/0051458 A1 | 2/2015 | Chen |
| 2015/0057108 A1 | 2/2015 | Regimbal |
| 2015/0065988 A1 | 3/2015 | Holderle et al. |
| 2015/0089439 A1 | 3/2015 | Wada |
| 2015/0114515 A1 | 4/2015 | Phallen |
| 2015/0141921 A1 | 5/2015 | Stewart et al. |
| 2015/0168958 A1 | 6/2015 | Downie et al. |
| 2015/0224252 A1 | 8/2015 | Borges et al. |
| 2015/0265765 A1 | 9/2015 | Yavorsky et al. |
| 2015/0278474 A1 | 10/2015 | Stueckemann |
| 2015/0289823 A1 | 10/2015 | Rack-Gomer et al. |
| 2015/0338340 A1 | 11/2015 | Jiang et al. |
| 2015/0363086 A1 | 12/2015 | Lim |
| 2015/0371004 A1 | 12/2015 | Jones |
| 2016/0000998 A1 | 1/2016 | Estes |
| 2016/0019352 A1 | 1/2016 | Seo |
| 2016/0042264 A1 | 2/2016 | Borges et al. |
| 2016/0051750 A1 | 2/2016 | Tsoukalis |
| 2016/0110088 A1 | 4/2016 | Vik et al. |
| 2016/0144101 A1 | 5/2016 | Pananen |
| 2016/0151560 A1 | 6/2016 | Toro et al. |
| 2016/0151562 A1 | 6/2016 | Magers et al. |
| 2016/0151601 A1 | 6/2016 | Cardelius et al. |
| 2016/0158437 A1 | 6/2016 | Biasi et al. |
| 2016/0193604 A1 | 7/2016 | McFarland et al. |
| 2016/0253460 A1 | 9/2016 | Kanada |
| 2016/0339167 A1 | 11/2016 | Ledford et al. |
| 2017/0010677 A1 | 1/2017 | Roh |
| 2017/0043089 A1 | 2/2017 | Handler |
| 2017/0056604 A1 | 3/2017 | Cowan |
| 2017/0068498 A1 | 3/2017 | Hashem |
| 2017/0132867 A1 | 5/2017 | Berg et al. |
| 2017/0354941 A1 | 12/2017 | Brown et al. |
| 2018/0018440 A1 | 1/2018 | Sugawara |
| 2018/0021514 A1 | 1/2018 | Rosinko et al. |
| 2018/0206798 A1 | 7/2018 | Murai |
| 2018/0296751 A1 | 10/2018 | Lefort et al. |
| 2018/0300994 A1 | 10/2018 | Nelson et al. |
| 2018/0326146 A1 | 11/2018 | Gupta et al. |
| 2019/0072405 A1 | 3/2019 | Luchner |
| 2019/0091401 A1 | 3/2019 | Ruchti et al. |
| 2019/0111209 A1 | 4/2019 | Murphy et al. |
| 2019/0117890 A1 | 4/2019 | Oruklu et al. |
| 2019/0160254 A1 | 5/2019 | Anand |
| 2019/0196770 A1 | 6/2019 | Fryman |
| 2019/0201607 A1 | 7/2019 | Öberg |
| 2019/0262535 A1 | 8/2019 | Shubinsky et al. |
| 2019/0282757 A1 | 9/2019 | Gylland et al. |
| 2019/0351131 A1 | 11/2019 | Butterfield et al. |
| 2020/0054825 A1 | 2/2020 | Kamen et al. |
| 2020/0069864 A1 | 3/2020 | Shubinsky et al. |
| 2020/0113784 A1 | 4/2020 | Lopez et al. |
| 2020/0238007 A1 | 7/2020 | Day |
| 2020/0330689 A1 | 10/2020 | Nemoto et al. |
| 2020/0384191 A1 | 12/2020 | Rosinko et al. |
| 2021/0158481 A1 | 5/2021 | Wang |
| 2021/0158946 A1 | 5/2021 | Starobinets et al. |
| 2021/0162115 A1 | 6/2021 | Surine |
| 2021/0170101 A1 | 6/2021 | Cavendish, Jr. et al. |
| 2021/0260283 A1 | 8/2021 | Oruklu et al. |
| 2021/0295263 A1 | 9/2021 | Hume et al. |
| 2021/0304864 A1 | 9/2021 | Kamen et al. |
| 2021/0397396 A1 | 12/2021 | Fryman |
| 2022/0031943 A1 | 2/2022 | Dumas, III |
| 2022/0088305 A1 | 3/2022 | Cavendish, Jr. |
| 2022/0176037 A1 | 6/2022 | Jacobson et al. |
| 2022/0184302 A1 | 6/2022 | Cavendish, Jr. et al. |
| 2022/0184304 A1 | 6/2022 | Rinehart |
| 2022/0296806 A1 | 9/2022 | Shubinsky et al. |
| 2022/0305200 A1 | 9/2022 | Gylland et al. |
| 2022/0331518 A1 | 10/2022 | Shubinsky et al. |
| 2022/0362463 A1 | 11/2022 | Lindo et al. |
| 2022/0401640 A1 | 12/2022 | Jacobson |
| 2023/0010290 A1 | 1/2023 | Oruklu et al. |
| 2023/0010638 A1 | 1/2023 | Rubalcaba, Jr. et al. |
| 2023/0017117 A1 | 1/2023 | Sileika et al. |
| 2023/0058662 A1 | 2/2023 | Ruchti et al. |
| 2023/0112979 A1 | 4/2023 | Xavier |
| 2023/0115595 A1 | 4/2023 | Cousineau et al. |
| 2023/0181419 A1 | 6/2023 | Fister |
| 2023/0245741 A1 | 8/2023 | Shigyo |
| 2023/0270938 A1 | 8/2023 | Dumas, III et al. |
| 2023/0285669 A1 | 9/2023 | Day |
| 2023/0310735 A1 | 10/2023 | Cousineau |
| 2024/0201922 A1 | 6/2024 | Fryman |
| 2024/0366858 A1 | 11/2024 | Cousineau et al. |

FOREIGN PATENT DOCUMENTS

| | | |
|---|---|---|
| CA | 2 113 473 | 3/1993 |
| CA | 2 551 817 | 7/2005 |
| CA | 2 554 407 | 8/2005 |
| CN | 105682703 | 6/2016 |
| CN | 107106042 | 8/2017 |
| CN | 110573195 | 12/2019 |
| CN | 105848694 | 1/2020 |
| CN | 111954966 | 11/2020 |
| CN | 306893275 | 10/2021 |
| CN | 307412164 | 6/2022 |
| CN | 307979072 | 4/2023 |
| CN | 112105405 | 8/2023 |
| CN | 308499458 | 3/2024 |
| CO | 0020220004676-0001 | 11/2022 |
| CO | 0020220008155-0001 | 11/2022 |
| DE | 31 12 762 | 1/1983 |
| DE | 34 35 647 | 7/1985 |
| DE | 35 30 747 | 3/1987 |
| DE | 37 20 664 | 1/1989 |
| DE | 38 27 444 | 2/1990 |
| DE | 197 34 002 | 9/1998 |
| DE | 199 01 078 | 2/2000 |
| DE | 198 40 965 | 3/2000 |
| DE | 198 44 252 | 3/2000 |
| DE | 199 32 147 | 1/2001 |
| DE | 102 49 238 | 5/2004 |
| DE | 103 52 456 | 7/2005 |
| EM | 008932172-0003 | 4/2022 |
| EM | 008932172-0004 | 4/2022 |
| EP | 0 282 323 | 9/1988 |
| EP | 0 291 727 | 11/1988 |
| EP | 0 319 272 | 6/1989 |

(56) References Cited

FOREIGN PATENT DOCUMENTS

| | | |
|---|---|---|
| EP | 0 319 275 | 6/1989 |
| EP | 0 335 385 | 10/1989 |
| EP | 0 337 092 | 10/1989 |
| EP | 0 341 582 | 11/1989 |
| EP | 0 370 162 | 5/1990 |
| EP | 0 387 724 | 9/1990 |
| EP | 0 429 866 | 6/1991 |
| EP | 0 441 323 | 8/1991 |
| EP | 0 453 211 | 10/1991 |
| EP | 0 462 405 | 12/1991 |
| EP | 0 501 234 | 9/1992 |
| EP | 0 516 130 | 12/1992 |
| EP | 0 519 765 | 12/1992 |
| EP | 0 643 301 | 3/1995 |
| EP | 0 683 465 | 11/1995 |
| EP | 0 431 310 | 1/1996 |
| EP | 0 589 439 | 8/1998 |
| EP | 0 880 936 | 12/1998 |
| EP | 0 954 090 | 11/1999 |
| EP | 0 960 627 | 12/1999 |
| EP | 1 174 817 | 1/2002 |
| EP | 1 177 802 | 2/2002 |
| EP | 1 197 178 | 4/2002 |
| EP | 1 500 025 | 4/2003 |
| EP | 1 813 188 | 8/2007 |
| EP | 1 490 131 | 12/2007 |
| EP | 2 062 527 | 5/2009 |
| EP | 2 228 004 | 9/2010 |
| EP | 2 243 506 | 10/2010 |
| EP | 2 381 260 | 10/2011 |
| ES | 254513 | 10/1981 |
| FR | 2 717 919 | 9/1995 |
| GB | 2 121 971 | 1/1984 |
| GB | 2 303 706 | 2/1997 |
| GB | 2 312 022 | 10/1997 |
| GB | 2 312 046 | 10/1997 |
| GB | 6 201 192 | 4/2022 |
| GB | 6 201 193 | 4/2022 |
| JP | 01-301118 | 12/1989 |
| JP | 01-308568 | 12/1989 |
| JP | 04-231966 | 8/1992 |
| JP | 07-502678 | 3/1995 |
| JP | 07-289638 | 11/1995 |
| JP | 11-128344 | 5/1999 |
| JP | 2000-111374 | 4/2000 |
| JP | 2000-510575 | 8/2000 |
| JP | 2000-515716 | 11/2000 |
| JP | 2001-356034 | 12/2001 |
| JP | 2002-506514 | 2/2002 |
| JP | 2002-131105 | 5/2002 |
| JP | 2003-038642 | 2/2003 |
| JP | 2003-050144 | 2/2003 |
| JP | 2005-021463 | 1/2005 |
| JP | 2005-524081 | 3/2005 |
| JP | 2006-517423 | 7/2006 |
| JP | 2007-071695 | 3/2007 |
| JP | 2007-518471 | 7/2007 |
| JP | 2007-520270 | 7/2007 |
| JP | 2007-275106 | 10/2007 |
| JP | 2008-249400 | 10/2008 |
| JP | 4322661 | 6/2009 |
| JP | 2009-148592 | 7/2009 |
| JP | 2010-063767 | 3/2010 |
| JP | 5716879 | 3/2015 |
| TW | 201841165 | 11/2018 |
| WO | WO 84/000690 | 3/1984 |
| WO | WO 84/000894 | 3/1984 |
| WO | WO 90/007942 | 7/1990 |
| WO | WO 91/000113 | 1/1991 |
| WO | WO 91/016087 | 10/1991 |
| WO | WO 91/016416 | 10/1991 |
| WO | WO 93/004284 | 3/1993 |
| WO | WO 95/016200 | 6/1995 |
| WO | WO 95/031233 | 11/1995 |
| WO | WO 96/008755 | 3/1996 |
| WO | WO 96/025186 | 8/1996 |
| WO | WO 96/028209 | 9/1996 |
| WO | WO 96/041156 | 12/1996 |
| WO | WO 97/010013 | 3/1997 |
| WO | WO 97/030333 | 8/1997 |
| WO | WO 98/004304 | 2/1998 |
| WO | WO 98/012670 | 3/1998 |
| WO | WO 98/014234 | 4/1998 |
| WO | WO 98/019263 | 5/1998 |
| WO | WO 98/044320 | 10/1998 |
| WO | WO 98/056441 | 12/1998 |
| WO | WO 99/010029 | 3/1999 |
| WO | WO 99/015216 | 4/1999 |
| WO | WO 99/051003 | 10/1999 |
| WO | WO 99/052575 | 10/1999 |
| WO | WO 00/013580 | 3/2000 |
| WO | WO 00/013726 | 3/2000 |
| WO | WO 00/041621 | 7/2000 |
| WO | WO 01/014974 | 3/2001 |
| WO | WO 01/033484 | 5/2001 |
| WO | WO 02/005702 | 1/2002 |
| WO | WO 02/009795 | 2/2002 |
| WO | WO 02/027276 | 4/2002 |
| WO | WO 02/066101 | 8/2002 |
| WO | WO 02/087664 | 11/2002 |
| WO | WO 03/006091 | 1/2003 |
| WO | WO 03/053498 | 7/2003 |
| WO | WO 03/093780 | 11/2003 |
| WO | WO 2004/035115 | 4/2004 |
| WO | WO 2004/060455 | 7/2004 |
| WO | WO 2004/061745 | 7/2004 |
| WO | WO 2004/070556 | 8/2004 |
| WO | WO 2004/070994 | 8/2004 |
| WO | WO 2004/112579 | 12/2004 |
| WO | WO 2005/018716 | 3/2005 |
| WO | WO 2005/030489 | 4/2005 |
| WO | WO 2005/036447 | 4/2005 |
| WO | WO 2005/057175 | 6/2005 |
| WO | WO 2005/065146 | 7/2005 |
| WO | WO 2005/065749 | 7/2005 |
| WO | WO 2005/082450 | 9/2005 |
| WO | WO 2005/118015 | 12/2005 |
| WO | WO 2006/016122 | 2/2006 |
| WO | WO 2006/022906 | 3/2006 |
| WO | WO 2006/026270 | 3/2006 |
| WO | WO 2007/000426 | 1/2007 |
| WO | WO 2007/033025 | 3/2007 |
| WO | WO 2007/035567 | 3/2007 |
| WO | WO 2007/087443 | 8/2007 |
| WO | WO 2008/004560 | 1/2008 |
| WO | WO 2008/019016 | 2/2008 |
| WO | WO 2008/053193 | 5/2008 |
| WO | WO 2008/059492 | 5/2008 |
| WO | WO 2008/063429 | 5/2008 |
| WO | WO 2008/067245 | 6/2008 |
| WO | WO 2008/088490 | 7/2008 |
| WO | WO 2008/134146 | 11/2008 |
| WO | WO 2009/016504 | 2/2009 |
| WO | WO 2009/023406 | 2/2009 |
| WO | WO 2009/023407 | 2/2009 |
| WO | WO 2009/023634 | 2/2009 |
| WO | WO 2009/039203 | 3/2009 |
| WO | WO 2009/039214 | 3/2009 |
| WO | WO 2009/049252 | 4/2009 |
| WO | WO 2009/127683 | 10/2009 |
| WO | WO 2009/141504 | 11/2009 |
| WO | WO 2010/017279 | 2/2010 |
| WO | WO 2010/075371 | 7/2010 |
| WO | WO 2010/099313 | 9/2010 |
| WO | WO 2010/114929 | 10/2010 |
| WO | WO 2010/119409 | 10/2010 |
| WO | WO 2010/124127 | 10/2010 |
| WO | WO 2010/135646 | 11/2010 |
| WO | WO 2010/135654 | 11/2010 |
| WO | WO 2010/135670 | 11/2010 |
| WO | WO 2010/135686 | 11/2010 |
| WO | WO 2010/148205 | 12/2010 |
| WO | WO 2011/017778 | 2/2011 |
| WO | WO 2011/080188 | 7/2011 |

(56)                    References Cited

FOREIGN PATENT DOCUMENTS

| | | |
|----|------------------|---------|
| WO | WO 2011/109774 | 9/2011 |
| WO | WO 2012/042763 | 4/2012 |
| WO | WO 2012/082599 | 6/2012 |
| WO | WO 2012/108910 | 8/2012 |
| WO | WO 2012/167090 | 12/2012 |
| WO | WO 2013/036854 | 3/2013 |
| WO | WO 2013/096769 | 6/2013 |
| WO | WO 2015/134478 | 9/2015 |
| WO | WO 2016/160321 | 10/2016 |
| WO | WO 2017/051271 | 3/2017 |
| WO | WO 2017/087157 | 5/2017 |
| WO | WO 2017/144366 | 8/2017 |
| WO | WO 2019/063462 | 4/2019 |
| WO | WO 2019/092680 | 5/2019 |
| WO | WO 2020/214717 | 10/2020 |
| WO | WO 2022/020184 | 1/2022 |
| WO | WO 2022/072159 | 4/2022 |
| WO | WO 2022/125471 | 6/2022 |
| WO | WO 2023/064662 | 4/2023 |
| WO | WO 2023/108030 | 6/2023 |
| WO | WO 2023/192791 | 10/2023 |
| WO | WO 2023/244922 | 12/2023 |

OTHER PUBLICATIONS

Notice of Opposition in European Patent Application No. 16759381.3 (Patent No. EP3285827), dated May 31, 2023 in 48 pages.

Response to Notice of Opposition in European Patent Application No. 16759381.3 (Patent No. EP3285827), dated Oct. 23, 2023 in 63 pages.

Abbott Laboratories, "LifeCare® 5000, Plum®: Concurrent Flow Infusion System with DataPort™", System Operating Manual, Version 1.6, Jul. 1998, p. 76.

Alaedeen et al., "Total Parenteral Nutrition-Associated Hyperglycemia Correlates with Prolonged Mechanical Ventilation and Hospital Stay in Septic Infants", Journal of Pediatric Surgery, Jan. 2006, vol. 41, No. 1, pp. 239-244.

ALARIS® Medical Systems, "Signature Edition® GOLD - Single & Dual Channel Infusion System", San Diego, Ca, USA, date unknown, but believed to be at least as early as Nov. 29, 2008, pp. 2-88 & 2-91.

Allegro, "3955 - Full-Bridge PWM Microstepping Motor Drive", Datasheet, 1997, p. 16.

Aragon, Daleen RN, Ph.D., CORN, "Evaluation of Nursing Work Effort and Perceptions About Blood Glucose Testing in Tight Glycemic Control", American Journal of Critical Care, Jul. 2006, vol. 15, No. 4, pp. 370-377.

Baxter, "Baxter Receives 510(k) Clearance for Next-Generation SIGMA Spectrum Infusion Pump with Master Drug Library" Press Release, May 8, 2014, p. 2. <http://web.archive.org/web/20160403140025/http://www.baxter.com/news-media/newsroom/press- releases/2014/05_08_14_sigma.page>.

Bequette, Ph.D., "A Critical Assessment of Algorithms and Challenges in the Development of a Closed- Loop Artificial Pancreas", Diabetes Technology & Therapeutics, Feb. 28, 2005, vol. 7, No. 1, pp. 28-47.

Bequette, B. Wayne, Ph.D., "Analysis of Algorithms for Intensive Care Unit Blood Glucose Control", Journal of Diabetes Science and Technology, Nov. 2007, vol. 1, No. 6, pp. 813-824.

Binder et al., "Insulin Infusion with Parenteral Nutrition in Extremely Low Birth Weight Infants with Hyperglycemia", Journal of Pediatrics, Feb. 1989, vol. 114, No. 2, pp. 273-280.

Bode et al., "Intravenous Insulin Infusion Therapy: Indications, Methods, and Transition to Subcutaneous Insulin Therapy", Endocrine Practice, March/Apr. 2004, vol. 10, Supplement 2, pp. 71-80.

Buhrdorf et al., "Capacitive Micromachined Ultrasonic Transducers and their Application", Proceedings of the IEEE Ultrasonics Symposium, Feb. 2001, vol. 2, pp. 933-940.

Cannon, MD et al., "Automated Heparin-Delivery System to Control Activated Partial Thromboplastin Time", Circulation, Feb. 16, 1999, vol. 99, pp. 751-756.

"CareAware® Infusion Management", Cerner Store, as printed May 12, 2011, pp. 3, <https://store.cerner.com/items/7>.

Chen et al., "Enabling Location-Based Services on Wireless LANs", The 11th IEEE International Conference on Networks, ICON 2003, Sep. 28-Oct. 1, 2003, pp. 567-572.

Cheung et al., "Hyperglycemia is Associated with Adverse Outcomes in Patients Receiving Total Parenteral Nutrition", Diabetes Care, Oct. 2005, vol. 28, No. 10, pp. 2367-2371.

Coley et al., "Performance of Three Portable Infusion-Pump Devices Set to Deliver 2 mL/hr", American Journal of Health-System Pharmacy, Jun. 1, 1997, vol. 54, No. 11, pp. 1277-1280.

"Continually vs Continuously", <https://web.archive.org/web/20090813092423/http://www.diffen.com/difference/Continually_vs_Continuously>, as accessed Aug. 13, 2009 in 4 pages.

"CritiCore® Monitor: Critical Fluid Output and Core Bladder Temperature Monitor", BARD Urological Catheter Systems, Advertisement, 2005, pp. 2.

Daimiwal et al., "Wireless Transfusion Supervision and Analysis Using Embedded System", IEEE, 2010 International Conference ICBBT, China, Apr. 2010, pp. 56-60.

Davidson et al., "A Computer-Directed Intravenous Insulin System Shown to be Safe, Simple, and Effective in 120,618 h of Operation", Diabetes Care, Oct. 2005, vol. 28, No. 10, pp. 2418-2423.

"Decision of the Administrative Council of Oct. 16, 2013 Amending Rule 135 and 164 of the Implementing Regulations to the European Patent Convention (CA/D 17/13)", Official Journal EPO Nov. 2013, Nov. 2013, pp. 503-506. <http://archive.epo.org/epo/pubs/oj013/11_13/11_5033.pdf>.

"Decision of the Administrative Council of Oct. 27, 2009 Amending the Implementing Regulations to the European Patent Convention (CA/D 20/09)", Official Journal EPO Dec. 2009, Dec. 2009, pp. 582-584. <http://archive.epo.org/epo/pubs/oj009/12_09/12_5829.pdf>.

Diabetes Close Up, Close Concerns AACE Inpatient Management Conference Report, Consensus Development Conference on Inpatient Diabetes and Metabolic Control, Washington, D.C., Dec. 14-16, 2003, pp. 1-32.

"Differential Pressure Transmitter, Series PD-39 X", SensorsOne Ltd., Advertisement, Dec. 2005, pp. 2.

Dunster et al., "Flow Continuity of Infusion Systems at Low Flow Rates", Anaesthesia and Intensive Care, Oct. 1995, vol. 23, No. 5, pp. 5.

Fogt et al., Development and Evaluation of a Glucose Analyzer for a Glucose-Controlled Insulin Infusion System (Biostator®), Clinical Chemistry, 1978, vol. 24, No. 8, pp. 1366-1372.

"Froth", <http://www.merriam-webster.com/dictionary/froth>, as accessed May 13, 2015 in 1 page.

Goldberg et al., "Clinical Results of an Updated Insulin Infusion Protocol in Critically Ill Patients", Diabetes Spectrum, 2005, vol. 18, No. 3, pp. 188-191.

Halpern et al., "Changes in Critical Care Beds and Occupancy in the United States 1985-2000: Differences Attributable to Hospital Size", Critical Care Medical, Aug. 2006, vol. 34, No. 8, pp. 2105-2112.

Hospira, "Plum A+™ Infusion System" as archived Dec. 1, 2012, pp. 2. <www.hospira.com/products_and_services/infusion_pumps/plum/index>.

Hospira, "Plum XL™ Series Infusion System" Technical Service Manual, Feb. 2005, Lake Forest, Illinois, USA, pp. i-vii, 5-14, 8-3.

Ilfeld et al., "Delivery Rate Accuracy of Portable, Bolus-Capable Infusion Pumps Used for Patient-Controlled Continuous Regional Analgesia", Regional Anesthesia and Pain Medicine, Jan.-Feb. 2003, vol. 28, No. 1, pp. 17-23.

Ilfeld et al., "Portable Infusion Pumps Used for Continuous Regional Analgesia: Delivery Rate Accuracy and Consistency", Regional Anesthesia and Pain Medicine, Sept.-Oct. 2003, vol. 28, No. 5, pp. 424-432.

JMS Co., Ltd., "Infusion Pump: OT-701", Tokyo, Japan, 2002, pp. 4.

Kim, M.D., et al., "Hyperglycemia Control of the Nil Per Os Patient in the Intensive Care Unit: Introduction of a Simple Subcutaneous

(56)　　　　　References Cited

OTHER PUBLICATIONS

Insulin Algorithm", Nov. 2012, Journal of Diabetes Science and Technology, vol. 6, No. 6, pp. 1413-1419.

Kutcher et al., "The Effect of Lighting Conditions on Caries Interpretation with a Laptop Computer in a Clinical Setting", Elsevier, Oct. 2006, vol. 102, No. 4, pp. 537-543.

Lamsdale et al., "A Usability Evaluation of an Infusion Pump by Nurses Using a Patient Simulator", Proceedings of the Human Factors and Ergonomics Society 49th Annual Meeting, Sep. 2005, pp. 1024-1028.

Logan et al., "Fabricating Capacitive Micromachined Ultrasonic Transducers with a Novel Silicon-Nitride-Based Wafer Bonding Process", IEEE Transactions on Ultrasonics, Ferroelectrics, and Frequency Control, May 2009, vol. 56, No. 5, pp. 1074-1084.

Magaji et al., "Inpatient Management of Hyperglycemia and Diabetes", Clinical Diabetes, 2011, vol. 29, No. 1, pp. 3-9.

Mauseth et al., "Proposed Clinical Application for Tuning Fuzzy Logic Controller of Artificial Pancreas Utilizing a Personalization Factor", Journal of Diabetes Science and Technology, Jul. 2010, vol. 4, No. 4, pp. 913-922.

Maynard et al., "Subcutaneous Insulin Order Sets and Protocols: Effective Design and Implementation Strategies", Journal of Hospital Medicine, Sep./Oct. 2008, vol. 3, Issue 5, Supplement 5, pp. S29-S41.

Merry et al., "A New, Safety-Oriented, Integrated Drug Administration and Automated Anesthesia Record System", Anesthesia & Analgesia, Aug. 2001, vol. 93, No. 2 pp. 385-390.

Microchip Technology Inc., "MTA11200B; TrueGauge™ Intelligent Battery Management I.C.", <https://www.elektronik.ropla.eu/pdf/stock/mcp/mta11200b.pdf>, 1995, pp. 44.

Moghissi, Etie, MD, FACP, FACE, "Hyperglycemia in Hospitalized Patients", A Supplement to ACP Hospitalist, Jun. 15, 2008, pp. 32.

Nuckols et al., "Programmable Infusion Pumps in ICUs: An Analysis of Corresponding Adverse Drug Events", Journal of General Internal Medicine, 2007, vol. 23, Supp. 1, pp. 41-45.

Pretty et al., "Hypoglycemia Detection in Critical Care Using Continuous Glucose Monitors: An in Silico Proof of Concept Analysis", Journal of Diabetes Science and Technology, Jan. 2010, vol. 4, No. 1, pp. 15-24.

Saager et al., "Computer-Guided Versus Standard Protocol for Insulin Administration in Diabetic Patients Undergoing Cardiac Surgery", Annual Meeting of the American Society of Critical Care Anesthesiologists, Oct. 13, 2006.

Sebald et al., "Numerical Analysis of a Comprehensive in Silico Subcutaneous Insulin Absorption Compartmental Model", 31st Annual International Conference of the IEEE Engineering in Medicine and Biology Society, Sep. 2-6, 2009, pp. 3901-3904.

SGS-Thomson Microelectronics, "L6219—Stepper Motor Drive", Datasheet, Dec. 1996, pp. 10.

SGS-Thomson Microelectronics, "PBL3717A—Stepper Motor Drive", Datasheet, Apr. 1993, pp. 11.

Simonsen, Michael Ph.D., POC Testing, New Monitoring Strategies on Fast Growth Paths in European Healthcare Arenas, Biomedical Business & Technology, Jan. 2007, vol. 30, No. 1, pp. 1-36.

Smith, Joe, "Infusion Pump Informatics", CatalyzeCare: Transforming Healthcare, as printed May 12, 2011, pp. 2.

Tang et al., "Linear Dimensionality Reduction Using Relevance Weighted LDA", Pattern Recognition, 2005, vol. 38, pp. 485-493, <http://staff.ustc.edu.cn/~ketang/papers/TangSuganYaoQin_PR04. pdf>.

Thomas et al., "Implementation of a Tight Glycaemic Control Protocol Using a Web-Based Insulin Dose Calculator", Anaesthesia, 2005, vol. 60, pp. 1093-1100.

Van Den Berghe, M.D., Ph.D., et al., "Intensive Insulin Therapy in Critically Ill Patients", The New England Journal of Medicine, Nov. 8, 2001, vol. 345, No. 19, pp. 1359-1367.

Van Den Berghe, M.D., Ph.D., et al., "Intensive Insulin Therapy in the Medical ICU", The New England Journal of Medicine, Feb. 2, 2006, vol. 354, No. 5, pp. 449-461.

Westbrook et al., "Errors in the Administration of Intravenous Medications in Hospital and the Role of Correct Procedures and Nurse Experience", BMJ Quality & Safety, 2011, vol. 20, pp. 1027-1034.

Zakariah et al., "Combination of Biphasic Transmittance Waveform with Blood Procalcitonin Levels for Diagnosis of Sepsis in Acutely Ill Patients", Critical Care Medicine, 2008, vol. 36, No. 5, pp. 1507-1512.

International Search Report and Written Opinion received in PCT Application No. PCT/US2013/034041, dated Jun. 19, 2013 in 11 pages.

International Preliminary Report on Patentability and Written Opinion received in PCT Application No. PCT/US2013/034041, dated Oct. 9, 2014 in 10 pages.

Amazon, Post-it Message "Sign Here" Flags, 30/Dispenser, 4 Dispensers/Pack, Published Sep. 29, 2016, https://www.amazon. com/Assorted-Color-Colors-Dispenser-MMM684SH/dp/ B00006JNMN/?th=1, 2 pages.

File:Soldado, Raso Fuerza Aerea Boliviana.jpg, Feb. 9, 2021, https://commons.m.wikimedia.org/wiki/File:Soldado_Raso_Fuerza_ A%C3%A9rea_Boliviana.jpg, 1 page.

Fresenius, "Infusion Workstation: Orchestra® Base Intensive", Operator's Guide, Jun. 20, 2006, <https://manualmachine.com/fresenius/ orchestrabaseunit/7455278-user-manual/>, 24 pages.

"ICU Medical Receives FDA Clearance for New Infusion Pump", Medical Design & Development Staff, Aug. 29, 2023, https://www. medicaldesigndevelopment.com/topics/devices/news/22871498/icu-medical-receives-fda-clearance-for-new-infusion-pump, 2 pages.

Jusko: Moving from Basic Toward Systems Pharmacodynamic Models; Department of Pharmaceutical Sciences, School of Pharmacy and Pharmaceutical Sciences, State University of New York at Buffalo, Buffalo, New York 14214; Journal of Pharmaceutical Sciences, vol. 102, No. 9, Sep. 2013; DOI 10.1002/jps; in 11 pages.

Lesson 1: Introduction to Pharmacokinetics and Pharmacodynamics; Concepts in Clinical Pharmacokinetics; in 18 pages.

Meibohm, et al; Basic Concepts of Pharmacokinetic/pharmacodynamic (PK/PD) modelling; Department of Pharmaceutics, College of Pharmacy, University of Florida, Gainesville, FL, USA, International Journal of Clinical Pharmacology and Therapeutics, vol. 35, No. Oct. 1997 (401-413); 13 pages.

Safer Care Victoria: Dobutamine I Safer Care Victoria; https://www. safercare.vic.gov.au/clinical-guidance/critical/dobutamine; in 9 pages.

Safer Care Victoria: Dopamine I Safer Care Victoria; https://www. safercare.vic.gov.au/clinical-guidance/critical/dopamine; in 9 pages.

Safer Care Victoria: Adrenaline (epinephrine) I Safer Care Victoria; https://www.safercare.vic.gov.au/clinical-guidance/critical/adrenaline-epinephrine; in 9 pages.

Safer Care Victoria: Isoprenaline I Safer Care Victoria; https://www. safercare.vic.gov.au/clinical-guidance/critical/isoprenaline; in 8 pages.

Safer Care Victoria: Noradrenaline (norepinephrine) I Safer Care Victoria; https://www.safercare.vic.gov.au/clinical-guidance/critical/ noradrenaline-norepinephrine; in 8 pages.

The heart.org Medscape: nitroglycerin IV (Rx); glyceryl trinitrate IV, IV Nitroglycerin (nitroglycerin IV) dosing, indication, interaction, adverse effects, and more; https://reference.medscape.com/ drug/glyceryl-trinitrate-iv-iv-nitroglycerin-nitroglycerin-iv-342278#10; 1 page.

* cited by examiner

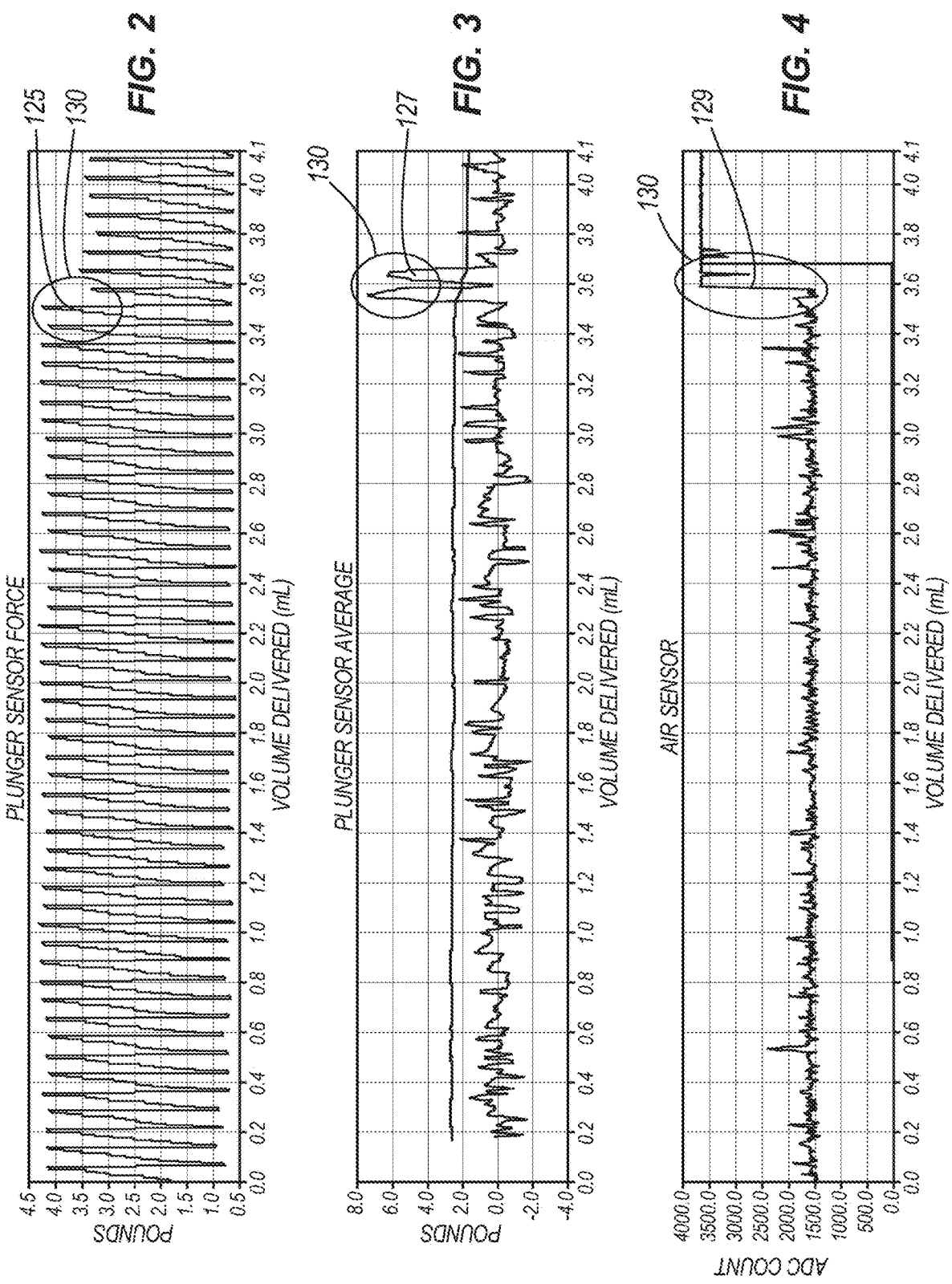

*280*

*282*

MOVING A PLUNGER AGAINST A FLUID CHAMBER

*284*

DETECTING A FORCE ACTING ON THE PLUNGER WITH A SENSOR

*286*

COMMUNICATING THE FORCE FROM THE SENSOR TO A PROCESSOR

*288*

DETERMINING THAT THE CHAMBER CONTAINS AIR WHEN (1), (2), (3) AND (4) OCCUR

*290*

TURNING ON AN ALARM WHEN AIR IS DETERMINED TO BE DISPOSED IN THE CHAMBER

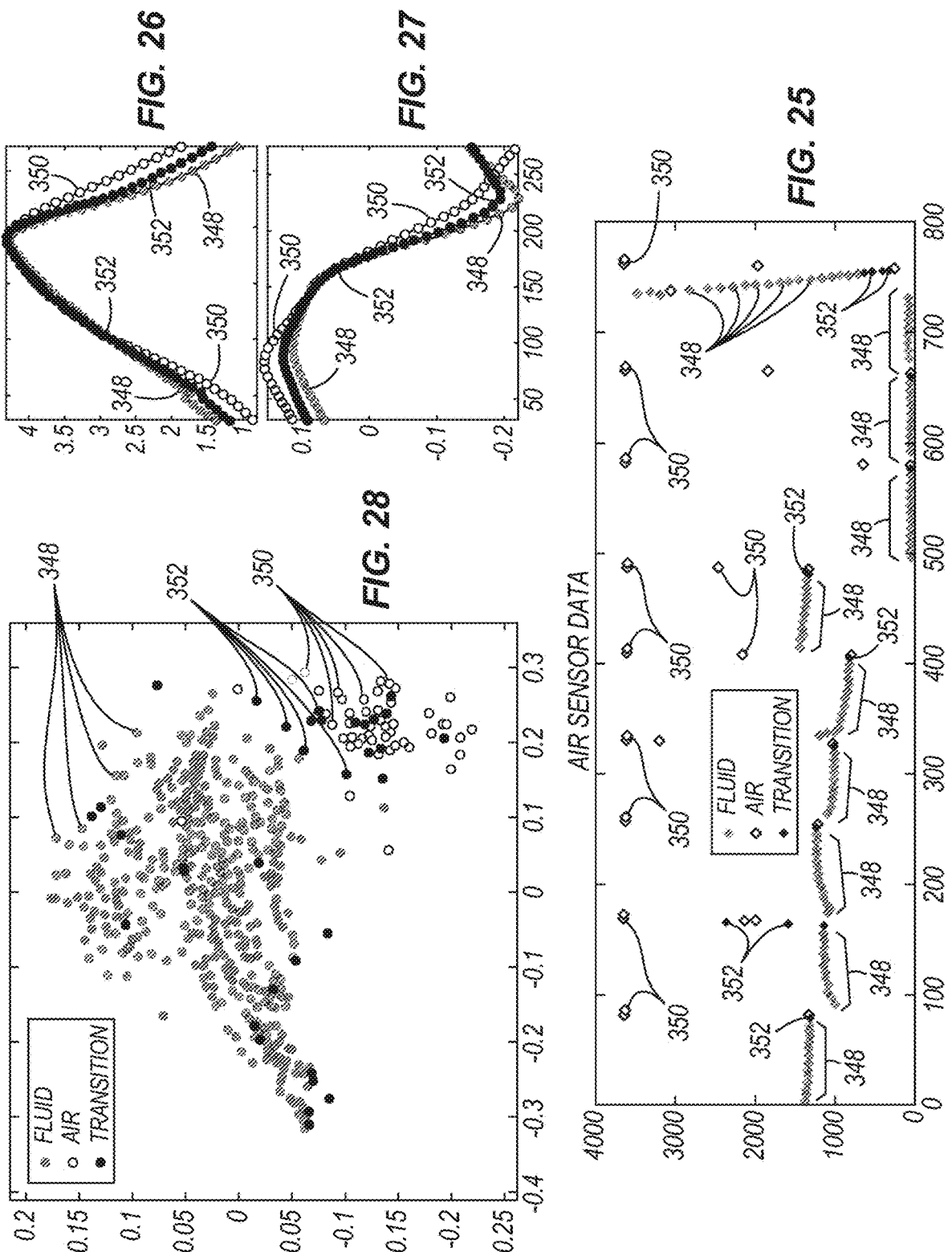

AIR DETECTION SYSTEM AND METHOD FOR DETECTING AIR IN A PUMP OF AN INFUSION SYSTEM

BACKGROUND OF THE INVENTION

Field of the Invention

The disclosure relates to systems and methods for detecting air in an infusion system.

Description of the Related Art

Existing systems and methods for detecting air in the line of an infusion device generally involve the use of ultrasonic sensors that detect the open circuit caused when air fills the volume between two sensor pairs. When the air sensor signal moves beyond a pre-defined air/fluid threshold, an alarm condition occurs and IV infusion is paused. Unfortunately, a variety of situations exist which either mask the presence of air, leading to false negatives, or generate false alarms. Fundamentally, this problem occurs because a single sensor with a univariate signal is applied to a relatively complex problem with multiple dimensions.

A system and method is needed which more accurately detects air in the line of an infusion device.

SUMMARY OF THE INVENTION

In one embodiment of the disclosure, a method for detecting air in a chamber of an infusion system is disclosed. In one step, a plunger is moved against a chamber containing fluid with an actuator device. In another step, a force acting on the plunger, as it moves against the chamber, is detected with a sensor. In an additional step, a measurement of the force acting on the plunger is electronically communicated from the sensor to a processor. In yet another step, a determination is made, with the processor, that the chamber contains air when: (1) a trigger event occurs in which a change in the force exceeds a threshold; and (2) subsequent to the trigger event a differential between a baseline average force acting on the plunger and a current average force acting on the plunger exceeds an expected force differential within a defined delay range.

In another embodiment of the disclosure, a method for detecting air in a chamber of an infusion system is disclosed. In one step, a plunger is moved against a chamber containing fluid with an actuator device. In another step, a force acting on the plunger, as it moves against the chamber, is detected with a sensor. In an additional step, a measurement of the force acting on the plunger is electronically communicated from the sensor to a processor. In yet another step, the processor is used to determine: (1) a baseline force profile; (2) a current force profile representing the current force acting on the plunger against the chamber; (3) a difference between the current force profile and the baseline force profile; and (4) that the chamber contains air when the calculated difference crosses a threshold.

In still another embodiment of the disclosure, a method for detecting air in a chamber of an infusion system is disclosed. In one step, a plunger is moved against a chamber containing fluid using an actuator device. In another step, a force acting on the plunger, as it moves against the chamber, is detected with a sensor. In yet another step, a measurement of the force acting on the plunger is electronically communicated from the sensor to a processor. In another step, the processor is used to: (1) preprocess a force profile detected by the sensor; (2) extract features from the force profile; and (3) classify the force profile as being an air force profile or a liquid force profile based on the extracted features of the force profile.

These and other features, aspects and advantages of the disclosure will become better understood with reference to the following drawings, description and claims.

BRIEF DESCRIPTION OF THE DRAWINGS

FIG. 2 illustrates a graph plotting a plunger sensor force curve per volume of fluid delivered;

FIG. 3 illustrates a corresponding graph to FIG. 2 plotting a plunger sensor force negative derivative curve per volume of fluid delivered;

FIG. 4 illustrates a corresponding graph to FIGS. 2 and 3 plotting an in-line sensor ADC curve per volume of fluid delivered;

3

Figures 17, 18:
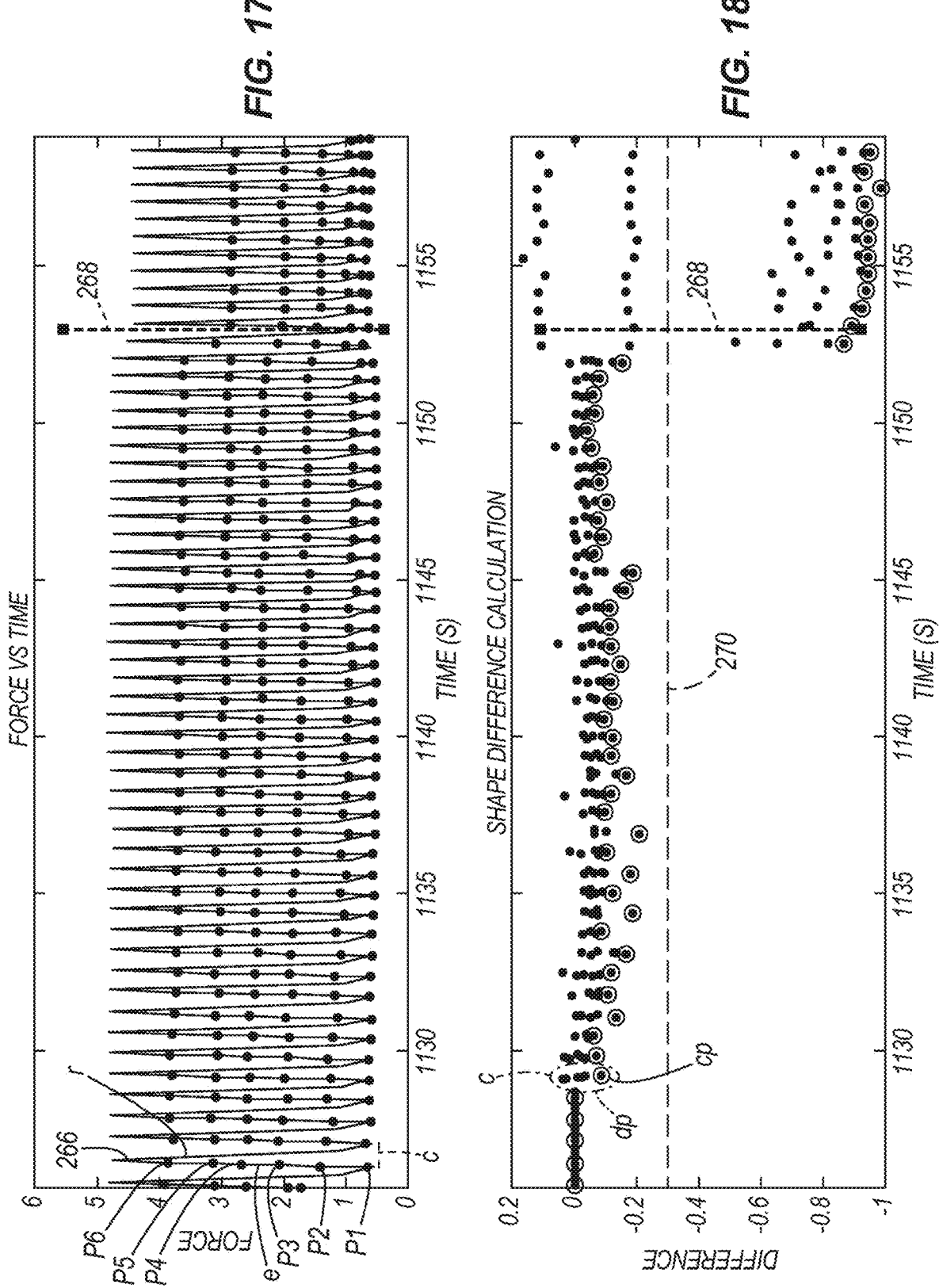
FIG. 17 illustrates a representative graph for one embodiment plotting a force sensor profile.
FIG. 18 illustrates a graph plotting for each cycle of the plunger of FIG. 17 six respective difference points representing the measured differences between a baseline, comprising liquid being in the chamber, and the corresponding points of each respective cycle of the plunger.
Figures 19, 20:
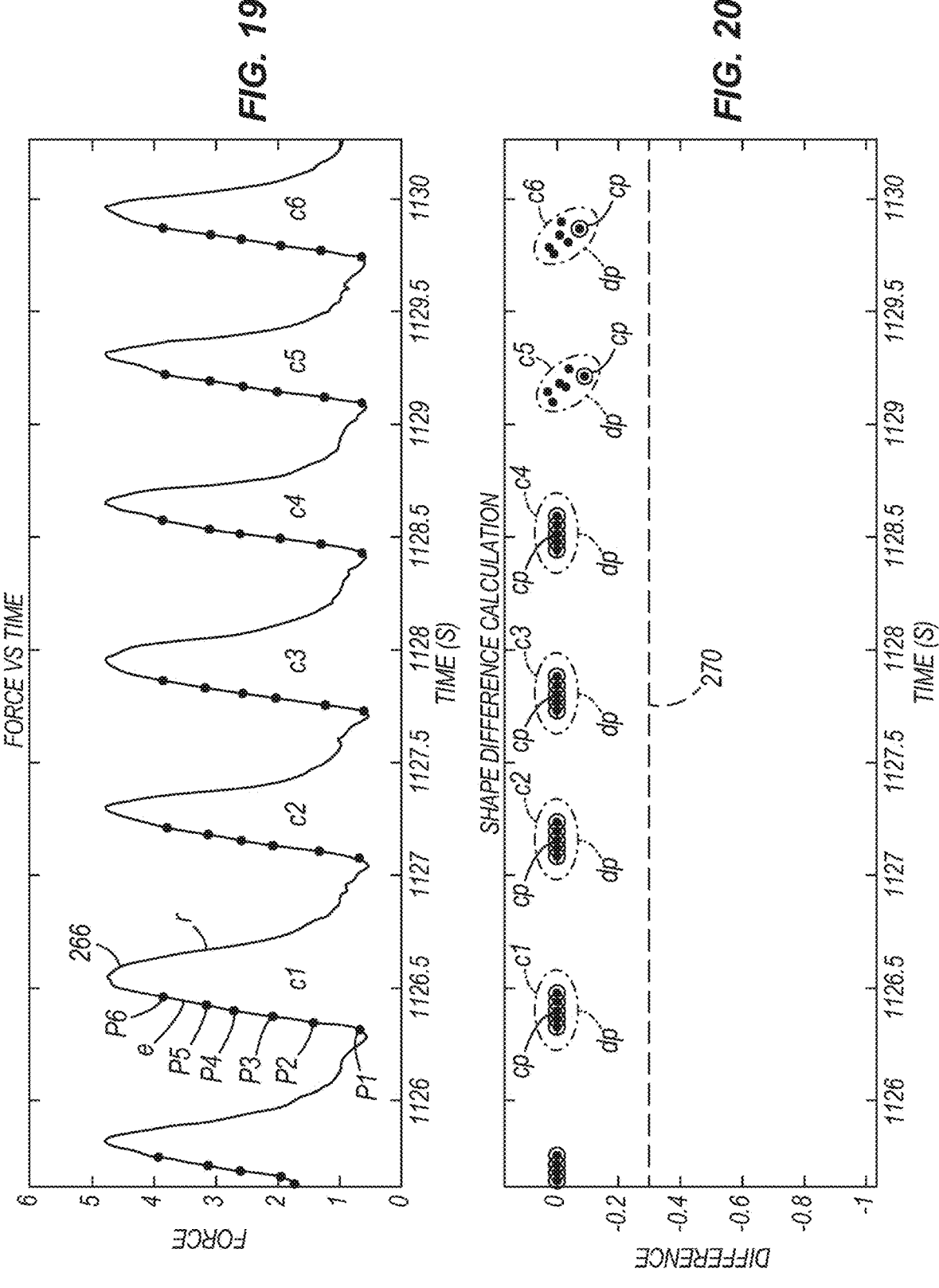
Figures 21, 22:
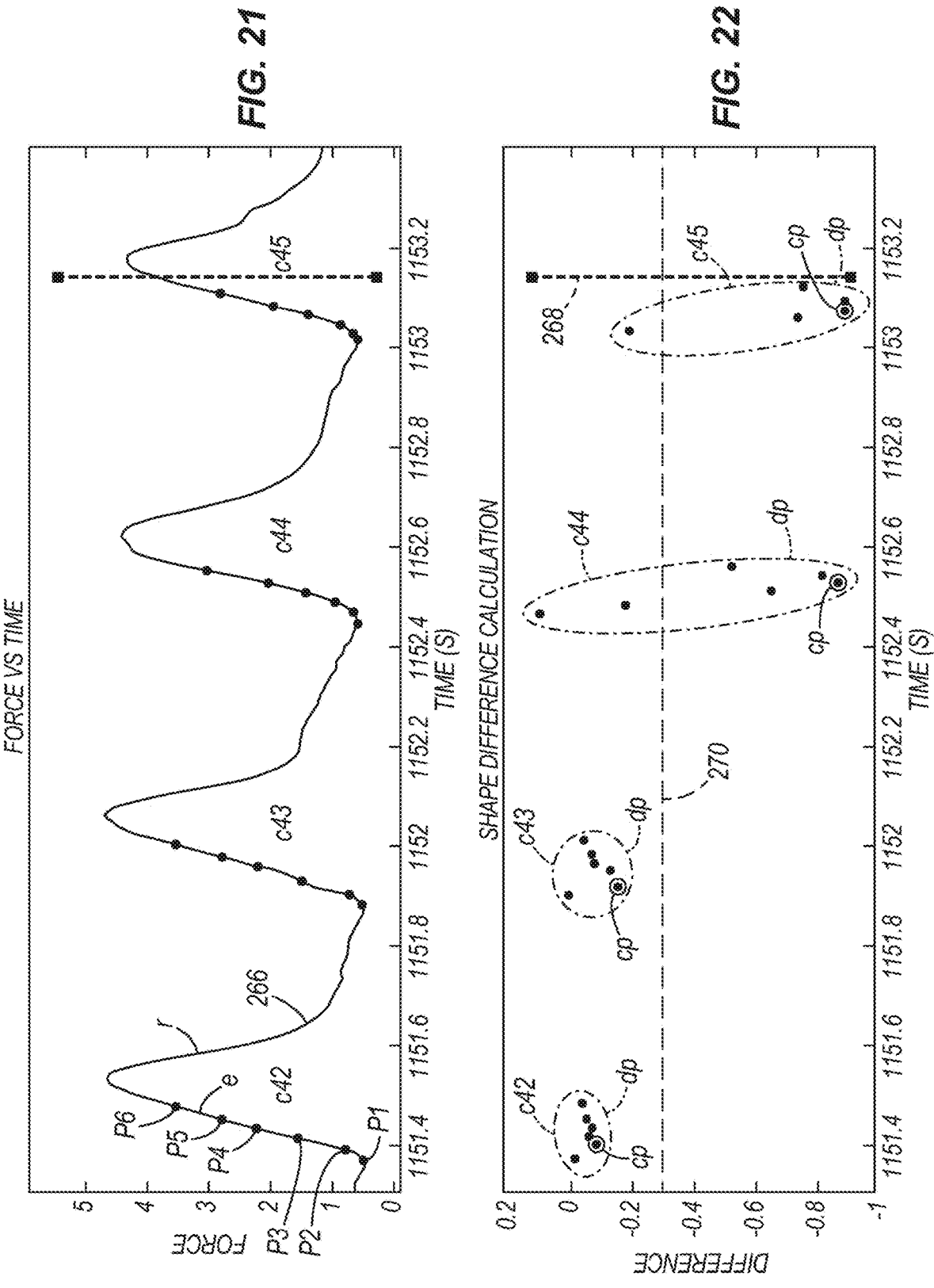
Figure 23:
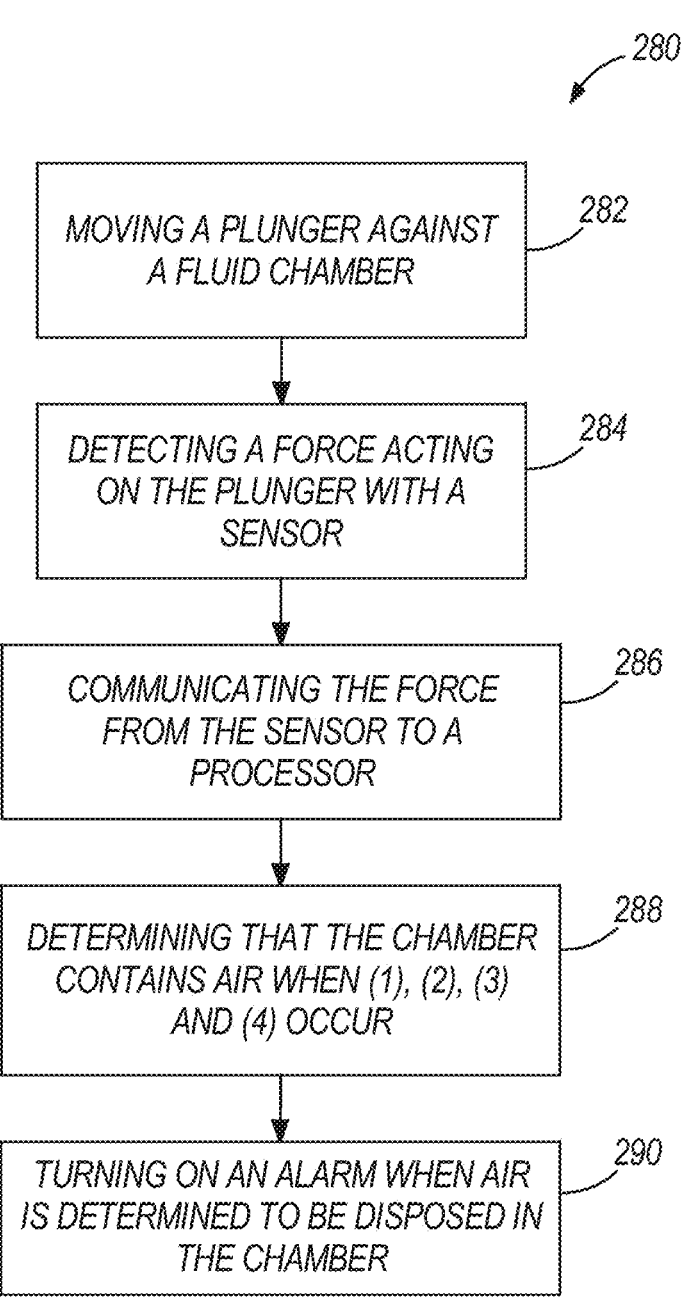
Figure 24:
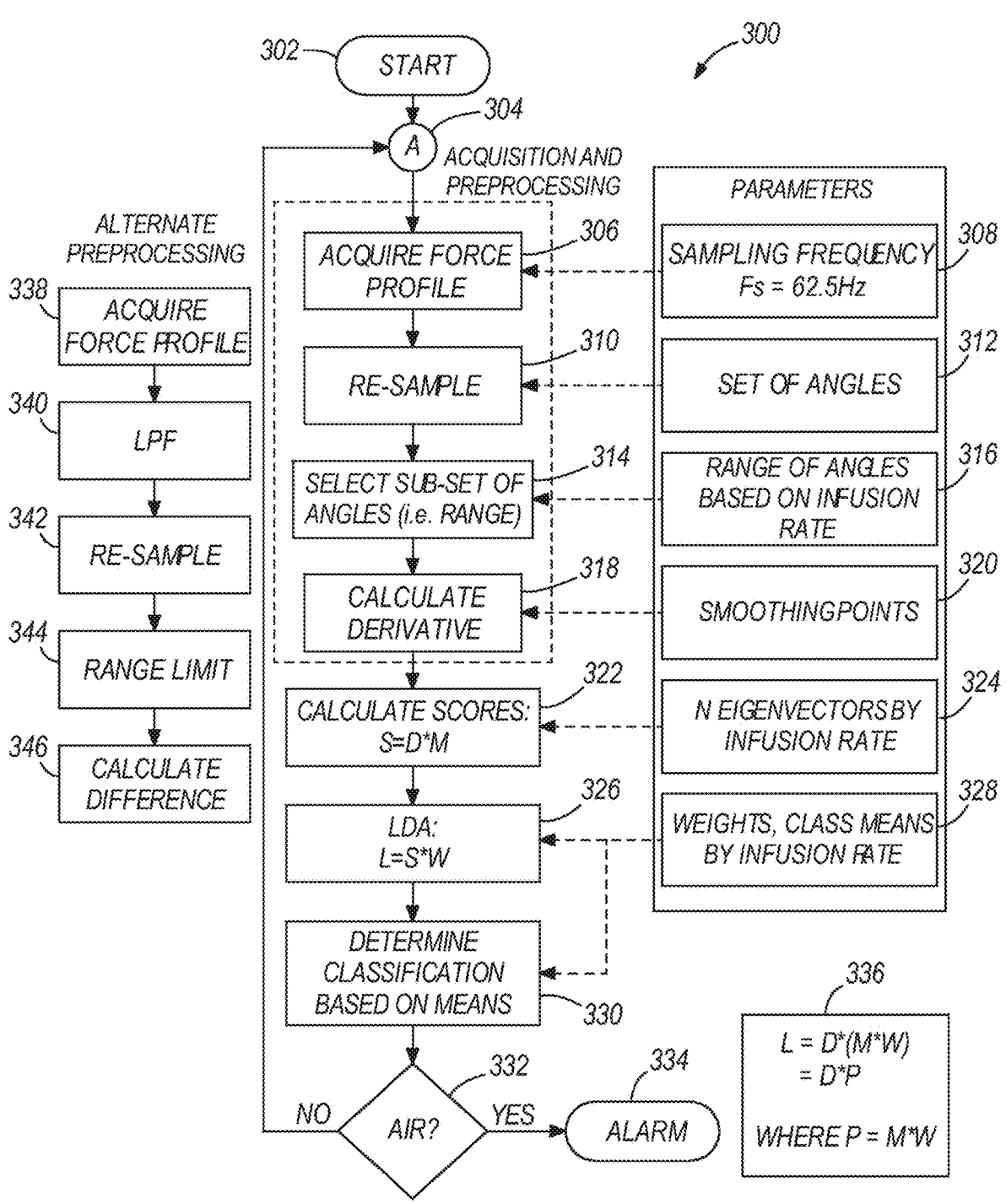
Figures 29, 30, 31, 32:
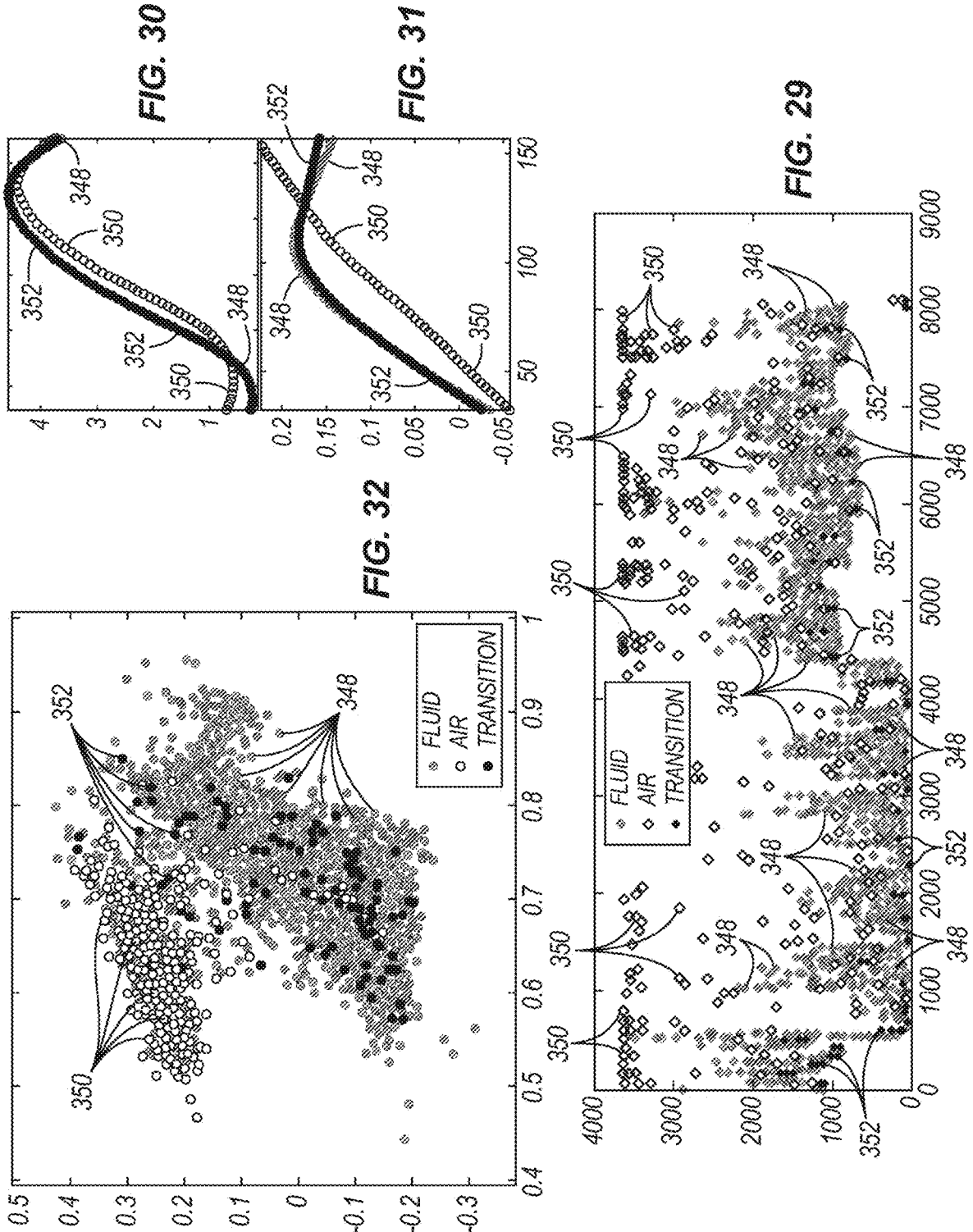
Figure 33:
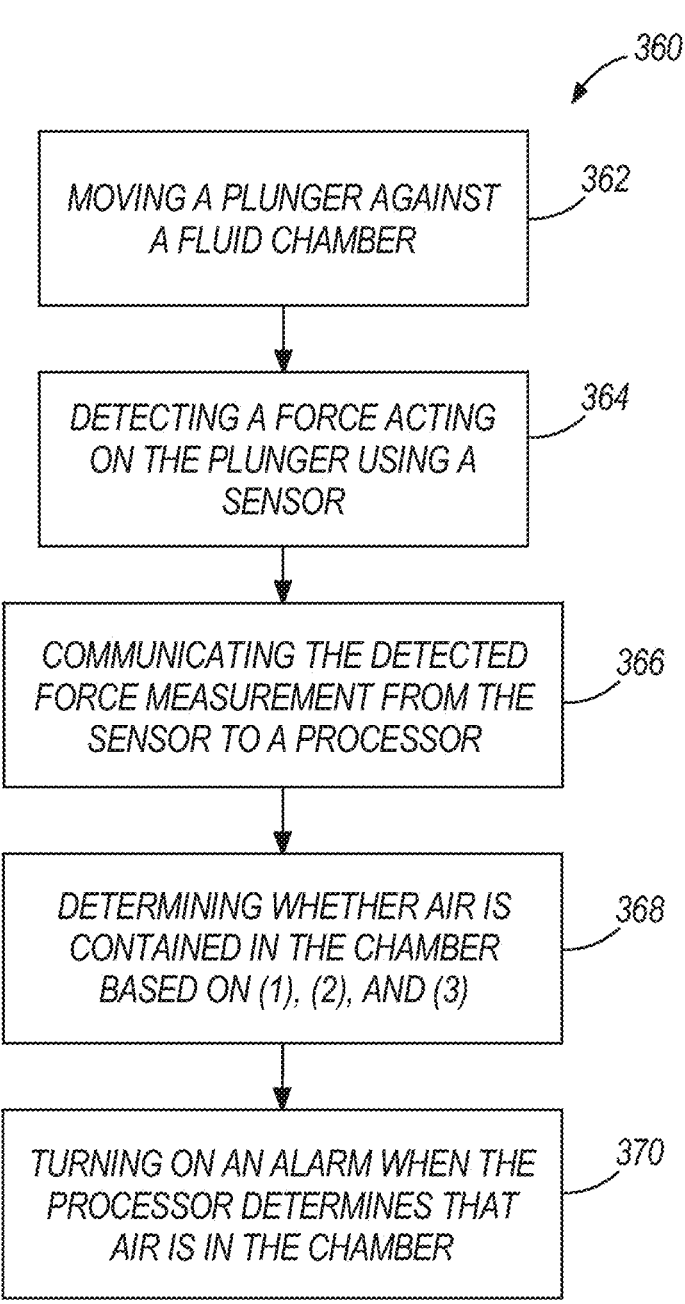
Figure 34:
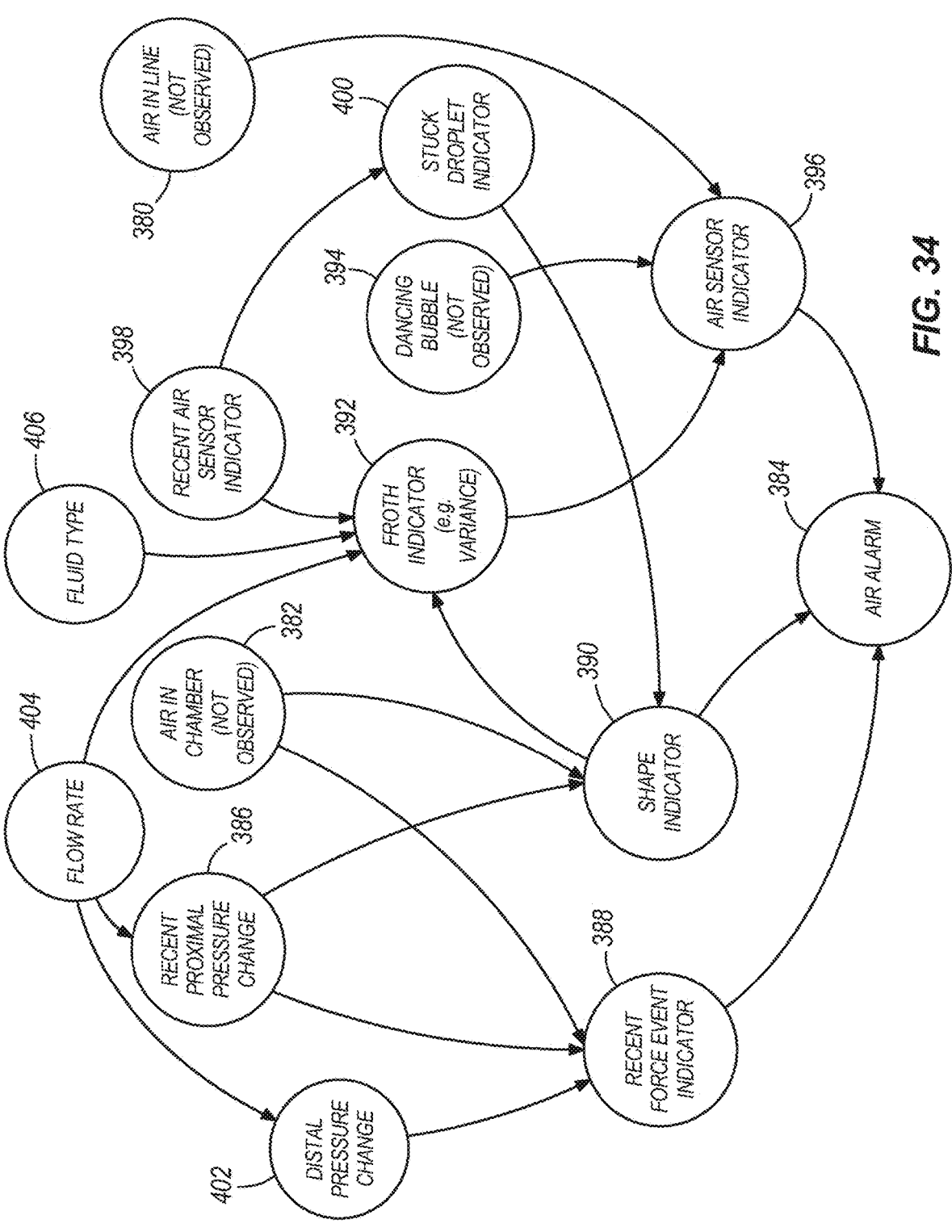

FIG. 19 illustrates a graph plotting the first six full cycles of the force sensor profile of FIG. 17;

FIG. 20 illustrates a graph plotting for each of the first six full cycles of the plunger of FIG. 18 six respective difference points representing the measured differences between a baseline, comprising liquid being in the chamber, and the corresponding points of each respective cycle of the plunger;

FIG. 21 illustrates a graph plotting the forty-second through forty-fifth cycles of the force sensor profile of FIG. 17;

FIG. 22 illustrates a graph plotting for the forty-second through forty fifth cycles of the plunger of FIG. 18 six respective difference points representing the measured differences between a baseline, comprising liquid being in the chamber, and the corresponding points of each respective cycle of the plunger;

FIG. 23 illustrates a flowchart for one embodiment of a method for detecting air in a chamber of an infusion system;

FIG. 24 illustrates one embodiment of a method, comprising a continuous flow chart, for determining whether air is contained in a chamber of a pump based upon a shape of the plunger force profile;

FIG. 25 illustrates a graph plotting air sensor data comprising representative points for each of fluid, air, and a transition;

FIG. 26 illustrates a graph plotting average force profiles on the plunger corresponding to the embodiment of FIG. 28 for each of fluid, air, and a transition;

FIG. 27 illustrates a graph plotting derivatives of the force profiles on the plunger corresponding to the embodiment of FIGS. 26 and 28 for each of fluid, air, and a transition;

FIG. 28 illustrates a graph applying a principal component analysis plotting representative points at an infusion rate of 2 milliliters per hour;

FIG. 29 illustrates a graph plotting air sensor data comprising representative points for each of fluid, air, and a transition;

FIG. 30 illustrates a graph plotting average force profiles on the plunger corresponding to the embodiment of FIG. 32 for each of fluid, air, and a transition;

FIG. 31 illustrates a graph plotting derivatives of the force profiles on the plunger corresponding to the embodiment of FIGS. 30 and 32 for each of fluid, air, and a transition;

FIG. 32 illustrates a graph applying a principal component analysis plotting representative points at an infusion rate of 1,000 milliliters per hour;

FIG. 33 illustrates a flowchart for one embodiment of a method for detecting air in a chamber of an infusion system; and FIG. 34 illustrates a flowchart of a Bayesian network showing a combination of algorithm sensors and a priori information which may be used to produce an indication of air-in-line or air in a chamber.

DETAILED DESCRIPTION OF THE PREFERRED EMBODIMENT

The following detailed description is of the best currently contemplated modes of carrying out the disclosure. The description is not to be taken in a limiting sense, but is made merely for the purpose of illustrating the general principles of the disclosure, since the scope of the disclosure is best defined by the appended claims. It is noted that the Figures are purely for illustrative purposes and are not to scale.

The instant disclosure provides methods and apparatus for determining whether air is present in an infusion system. Several types of pumps, such as Symbiq™, Plum™, and Gemstar™ pumps sold by Hospira, Inc., involve the use of a cassette with a chamber that is compressed by an actuated plunger to pump fluid at a controlled rate from the drug container to the patient. The chamber is surrounded by valves which open and close in a complimentary manner to ensure unidirectional flow. The measured force during a pumping cycle is directly related to the type of fluid in the chamber. Fluids are relatively incompressible and generate a higher and different force profile than air. Similarly, a combination of fluid and air in the chamber results in a hybrid shape profile which is indicative of the mixture percentages of both fluid and air. The instant disclosure discloses algorithms for utilizing the plunger force to detect the presence of air in the chamber to detect an air embolism prior to its infusion into a patient.

In one embodiment of the disclosure, an event detection algorithm is disclosed which determines a change from fluid to air in the pumping chamber on the basis of a change in the average force exerted against the plunger. The algorithm utilizes a derivative spike for event detection and a systematic reduction in the average force to confirm the nature of the change.

In another embodiment of the disclosure, a pattern recognition system/method is provided for recognizing fluid, air, or a mixture thereof in a pumping chamber. The system normalizes the force signal/profile acting on the plunger against the chamber to a baseline. The system then preprocesses the force signal/profile to smooth and re-samples the x-axis to a standard sampling interval with respect to plunger position. The system then extracts features such as the maximum absolute difference between the baseline and each subsequent force profile, or other types of features. The system then classifies the force profile as being air, fluid, or a combination thereof using linear discriminate analysis or another type of analysis system/method.

In still another embodiment of the disclosure, a varied pattern recognition system/method is provided for recognizing fluid, air, or a mixture thereof in a pumping chamber. The system, without normalizing to a baseline, preprocesses the force signal/profile acting on the plunger against the chamber by applying a low pass filter or by applying another type of preprocessing system/method. The system then extracts features from the entire force profile or a subset thereof such as the signal frequency content, the signal phase, the standard deviation or variance, the maximum, the range, the plunger position of critical points, the scores based on a principal component analysis, or extracts other types of features. The system then classifies the force profile as being air, fluid, or a combination thereof using linear discriminate analysis, k-nearest neighbor, support vector machines, or another type of analysis system/method.

One or more systems/methods of the disclosure include components that are optimized/customized according to a delivery rate of the fluid within the pumping chamber. Some of the existing algorithms fail to account for the profound impact of delivery rate on the observed plunger sensor force profile and the detection electronics. One or more systems/methods of the disclosure provide normalization or clustering states that reduce this impact and thereby improve sensitivity.

One or more systems/methods of the disclosure may be combined with any existing systems/methods for detecting air in an infusion system to improve the reliability of air detection systems. For instance, many current systems/methods use acoustic or ultrasonic sensors to detect the presence of air in tubing segments. However, these systems/methods often do not consider the possibility of an acoustic short circuit or a bubble that is stuck or repetitively passes in front of the sensor. Many systems/methods rely on a single air ultrasonic sensor with a fixed threshold which separates the air sensor signal into two regions representing air and fluid. When a voltage is measured that is within the air signal region, the volume of air represented by the signal is accumulated until an alarm condition is met. The disclosure allows for the combination of the output of a force sensor signal with one or more air sensors to improve the reliability of existing air detection systems/methods. In doing so, the disclosed system/method does not require additional hardware modifications but instead leverages the acquired force signal. Additionally, the disclosure does not necessarily require the replacement of existing software modules for air detection but adds an additional safety and/or reliability layer to improve the robustness of existing air detection systems and methods.

Figure 1:
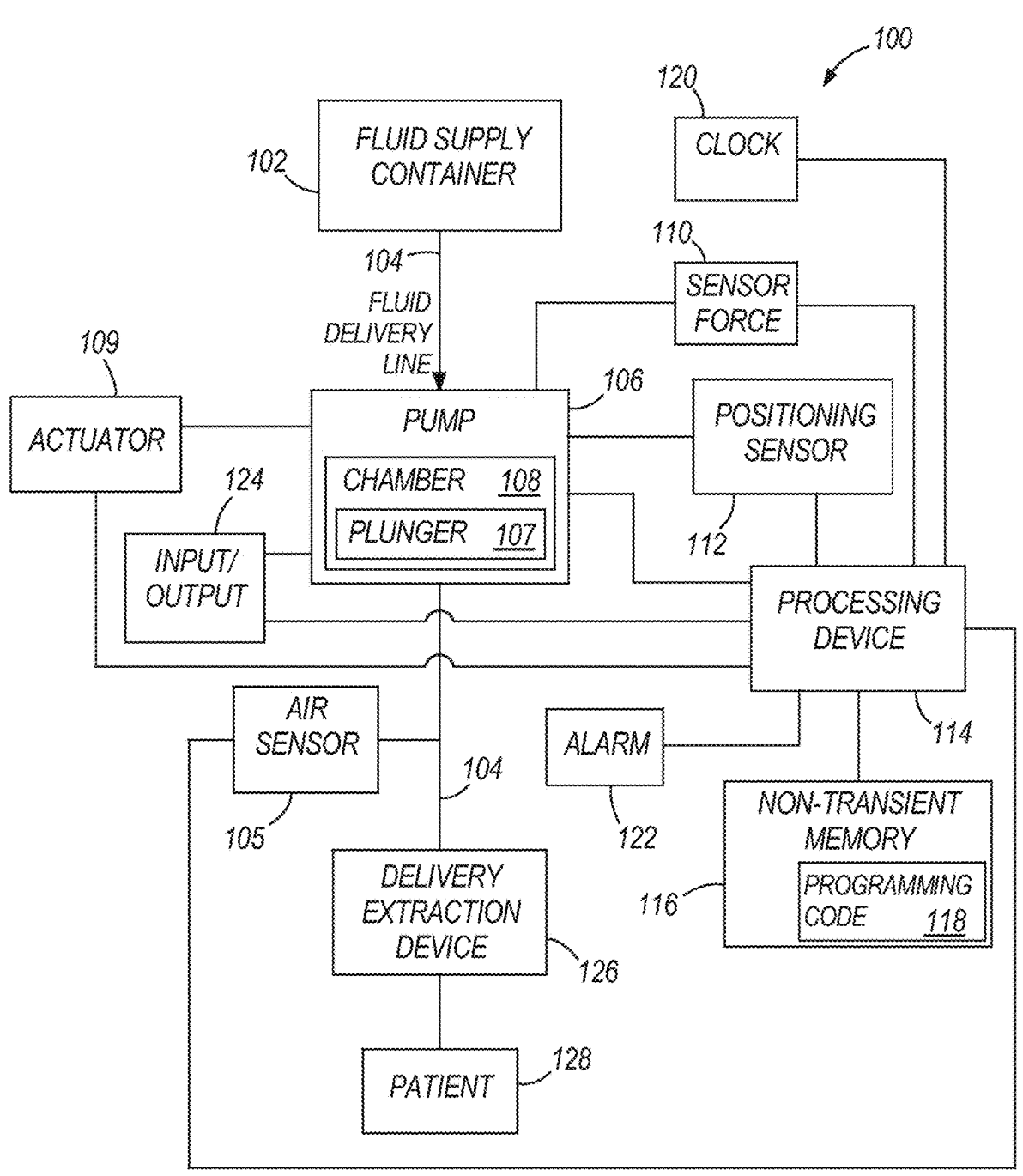
FIG. 1 illustrates a block diagram of a drug delivery infusion system under one embodiment of the disclosure.

FIG. 1 illustrates a block diagram of a drug delivery infusion system 100 under one embodiment of the disclosure. The drug delivery infusion system 100 comprises: a fluid supply container 102; a fluid delivery line 104; an air sensor 105 connected to the fluid delivery line 104; a pump 106 comprising a plunger 107 moveably disposed against a chamber 108; an actuator device 109; a sensor 110; a positional sensor 112; a processing device 114; a nontransient memory 116 storing programming code 118; a clock 120; an alarm 122; an input/output device 124; and a delivery/extraction device 126. The drug delivery infusion system 100 may comprise a drug delivery infusion system such as the Plum A+™, Gemstar™, Symbiq™, or other type of drug delivery infusion system. The fluid supply container 102 comprises a container for delivering fluid such as IV fluid or a drug to the patient 128 through the chamber 108 due to movement of the plunger 107 against the chamber 108. The fluid delivery line 104 comprises one or more tubes, connected between the fluid supply container 102, the pump 106, and the delivery/extraction device 126, for transporting fluid from the fluid supply container 102, through the pump 106, through the delivery/extraction device 126 to the patient 128. The fluid delivery line 104 may also be used to transport blood, extracted from the patient 128 using the delivery/extraction device 126, as a result of a pumping action of the pump 106. The pump 106 comprises a pump for pumping fluid from the supply container 102 or for pumping blood from the patient 128.

The pump 106 may comprise a plunger based pump, a peristaltic pump, or another type of pump. The chamber 108 comprises an inner cavity of the pump 106 into which fluid from the fluid supply container 102 is pumped into and through due to the moveably disposed plunger 107 moving against the chamber 108 as a result of the actuator device 109. The actuator device 109 may comprise a motor or another type of actuating device for moving the plunger 107 against the chamber 108. The sensor 110 is contained within the chamber 108 and detects the force acting on the plunger 107 as it moves against the chamber 108. The sensor 110 may comprise a force sensor signal comprising a pressure sensor, an elastic column, a strain gauge, or a piezoelectric crystal force transducer. The positional sensor 112 is used to determine a position of the plunger 107 against the chamber 108. The positional sensor 112 may comprise an encoder or may utilize the expected position based upon the commands sent to the actuator.

The processing device 114 is in electronic communication with the pump 106, the actuator device 109, the sensor 110, the positional sensor 112, the non-transient memory 116 storing the programming code 118, the clock 120, the alarm 122, and the input/output device 124. The processing device 114 comprises a processor for processing information received from the pump 106, the sensor 110, the positional sensor 112, and the clock 120, and for executing a software algorithm, contained in the programming code 118 stored in the nontransient memory 116, to determine if air, liquid (fluid), or a combination thereof is located in the chamber 108 of the pump 106. The non-transient memory 116 may be located within or outside of the processing device 114.

The clock 120 keeps time of activities of the drug delivery infusion system 100 including the plunger 107, the sensor 110, the positional sensor 112, and its other components. The alarm 122, when triggered by the processing device 114, is configured to notify the clinician as to the presence of air in the chamber 108, and to stop the pump 106 prior to an air embolism being delivered through the fluid delivery line 104 and the delivery/extraction device 126 to the patient 128. The input/output device 124 comprises a device which allows a clinician to input information, such as a user-inputted medication infusion program, to the processing device 114, and which also outputs information to the clinician. The delivery/extraction device 126 comprises a patient vascular access point device for delivering fluid from the fluid supply container 102 to the patient 128, or for extracting blood from the patient 128. The delivery/extraction device 126 may comprise a needle, a catheter, or another type of delivery/extraction device.

In one embodiment of the disclosure, the drug delivery infusion system 100 of FIG. 1 may determine when air is present in the chamber 108 by analyzing the force on the plunger 107 and the derivative of the force acting on the plunger 107 per delivered volume of the fluid or air exiting the chamber 108. This is because it has been discovered that when air reaches the chamber 108, the derivative force acting on the plunger 107 per the delivered volume of the fluid exiting the chamber 108 spikes in the downward direction and then returns to a baseline value, and that the average force on the plunger 107 then proceeds to drop slightly as the chamber 108 fills with air. To process this information, six data points per cycle of the plunger 107 may be gathered. In other embodiments, a varying number of data points per cycle of the plunger 107 may be gathered.

Corresponding FIGS. 2-4 illustrate typical data for one embodiment of a single iteration and end-of-bag event in which air is discovered in the chamber of FIG. 1. FIG. 2 illustrates a graph plotting a plunger sensor force curve 125 per volume of fluid delivered. The Y-axis represents pounds of force on the plunger detected by a plunger force sensor and the X-axis represents volume in milliliters of the fluid delivered from the chamber. FIG. 3 illustrates a corresponding graph to FIG. 2 plotting a plunger sensor force negative derivative curve 127 per volume of fluid delivered. The Y-axis represents a derivative of the average force on the plunger of FIG. 2 in pounds per unit volume and the X-axis represents volume in milliliters of the fluid delivered from the chamber. FIG. 4 illustrates a corresponding graph to FIGS. 2 and 3 plotting an in-line air sensor ADC curve 129 per volume of fluid delivered. The Y-axis represents an ADC count (also referred to as Analog-to-Digital-Count) of the fluid in-line as detected by an air sensor and the X-axis represents volume in milliliters of the fluid delivered from the chamber. As illustrated by FIG. 3, the transition from fluid to air occurs at the point in volume where the derivative of the force on the plunger spikes at location 130. As illustrated by FIG. 2, the force on the plunger drops at this same location 130. As illustrated by FIG. 4, the ADC count dramatically increases at this same location 130.

Figure 5:
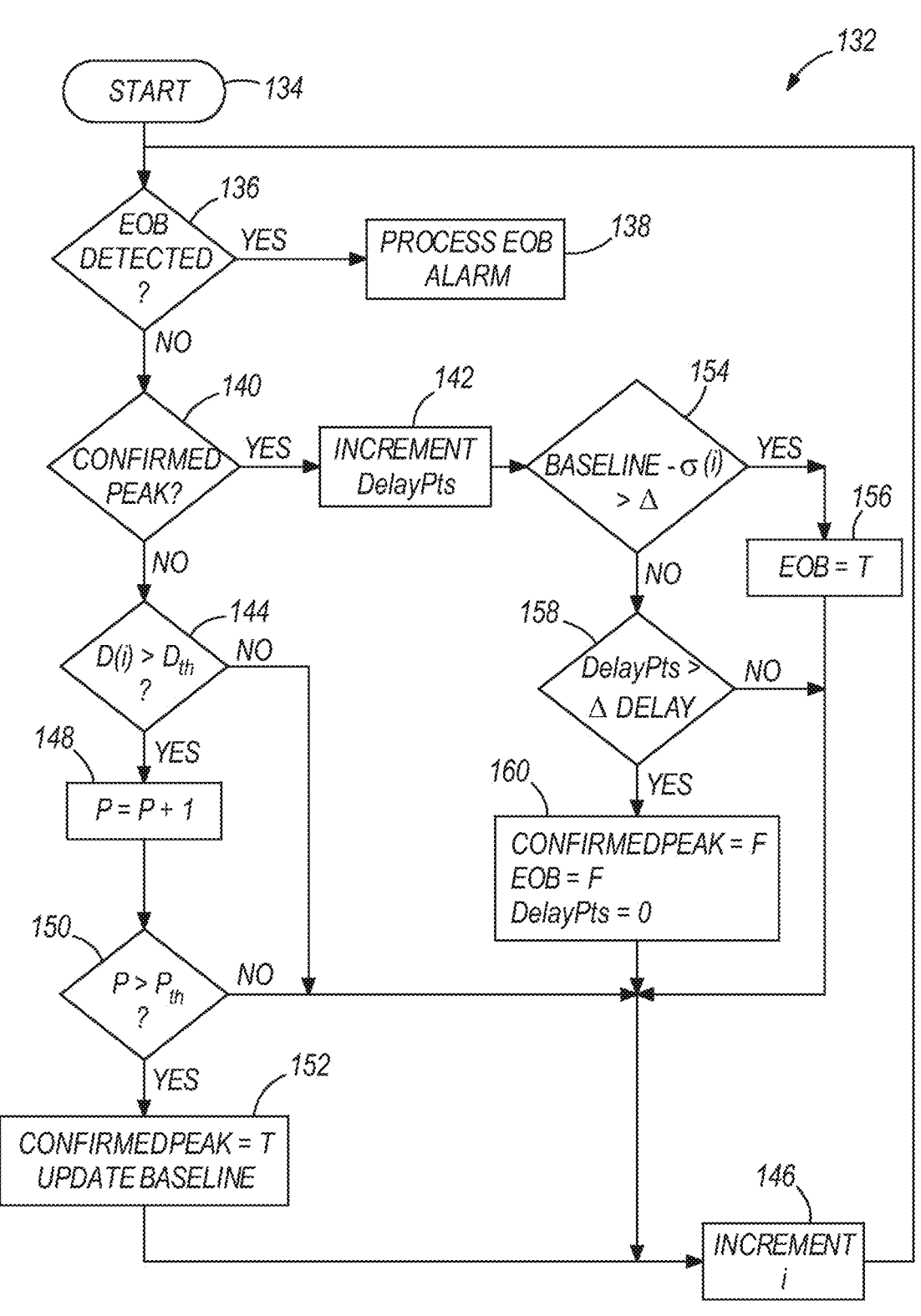
FIG. 5 illustrates one embodiment of a method, comprising a continuous flow chart, under the disclosure for determining whether air is contained in a chamber of a pump.

FIG. 5 illustrates one embodiment of a method 132, comprising a continuous flow chart, under the disclosure for determining whether air is contained in a chamber of a pump. The method 132 may be implemented using the drug delivery infusion system 100 of FIG. 1 with the plunger being moved with the actuator device against the chamber containing fluid, the sensor detecting a force acting on the plunger as it moves against the chamber, the processor processing the force measurements taken by the sensor and implementing programming code stored in a non-transient memory in order to determine whether air is contained in the chamber using the algorithm set forth in method 132, and the alarm being turned on if the processor determines that air is contained in the chamber which may trigger the pump being shut down. Moreover, the method 132 may utilize the clock of the drug delivery infusion system 100 of FIG. 1 to keep time of activities of the plunger or the sensor, and may use the positional sensor to determine a position of the plunger. In other embodiments, the method 132 may utilize varying components to implement the method.

In step 134, the method starts. After step 134, in step 136 a determination is made as to whether the end-of-bag (EOB), or equivalent situation in which the chamber contains air, has been detected. If the answer to the determination in step 136 is 'yes' and the end of the bag has been detected, the method proceeds to step 138 and an end-of-bag alarm is turned on to indicate that air is in the chamber. This end-of-bag (EOB) event may pause the pump infusion or be used by another algorithm to qualify an air-in-line alarm. If the answer to the determination in step 136 is 'no' and the end of the bag has not been detected, the method proceeds to step 140 in which a determination is made as to whether there is a previously confirmed peak. If the answer to the determination in step 140 is 'yes' and there is a confirmed peak, the method proceeds to step 142 which is discussed more thoroughly below. If the answer to the determination in step 140 is 'no' and there is not a previously confirmed peak, the method proceeds to step 144 in which a determination is made as to whether a trigger event has occurred in which the current negative derivative (of the average force) $D(i)$ of the force of the plunger per delivered volume of the fluid exiting the chamber exceeds a derivative threshold Dth which indicates the beginning of a possible end-of-bag (EOB) event signifying that air may have entered the chamber. It should be noted that variable i is initially set to 1. The derivative threshold Dth is flow dependent. The derivative threshold Dth may be set to 1.5 for a flow rate of the fluid below 200 milliliters per hour and to 3.0 for a flow rate of the fluid above 200 milliliters per hour. In other embodiments, the derivative threshold Dth may be varied as a direct function of flow rate.

If the answer to the determination in step 144 is 'no,' the method proceeds to step 146, increments variable i using the equation $i=i+1$, and then proceeds back to and repeats step 136. If the answer to the determination in step 144 is 'yes,' the method proceeds to step 148 and increments variable P applying using the equation $P=P+1$. It should be noted that variable P is initially set to 0. After step 148, the method proceeds to step 150 in which a determination is made as to whether variable P is greater than the consecutive point threshold Pth. In one embodiment, the consecutive point threshold Pih is set to 1. In other embodiments, the consecutive point threshold Pih may be varied. The consecutive point threshold Pih represents one less than the number of consecutive points P that the current negative derivative (average) $D(i)$ of the force of the plunger versus volume of the fluid delivered must exceed a derivative threshold D1h in order to indicate a possible end-of-bag (EOB) event signifying that air may be in the chamber. If the answer to the determination in step 150 is 'no,' the method proceeds to step 146, increments i applying the equation $i=i+1$, and then proceeds back to and repeats step 136. If the answer to the determination in step 150 is 'yes,' the method proceeds to step 152 in which the peak is confirmed, and a baseline B is taken.

The baseline B represents the average force during infusion when the chamber is filled with fluid. In one embodiment, the baseline B comprises the average force acting on the plunger over a defined baseline range occurring up to the trigger event. In one embodiment, the defined baseline range comprises the immediately previous 100 micro liters of average force data on the plunger taken immediately previous and up to the trigger event. In one embodiment, the baseline range may comprise multiple cycles of average force data. In other embodiments, the baseline range may vary. The trigger event comprises the point at which the negative derivative force D (i) acting on the plunger per the delivered volume of the fluid exiting the chamber first exceeds the derivative threshold Dth so long as subsequently the number of consecutive measured points P of the cycle of the plunger from the trigger event, in which the negative derivative force D (i) acting on the plunger per the delivered volume of the fluid exiting the chamber continues to exceed the derivative threshold Dth, exceeds the consecutive point threshold Pth. In other embodiments, the trigger event may vary. After step 152, the method proceeds to step 146, increments variable i using the equation $i=i+1$, and then proceeds back to and repeats step 136.

As referred to earlier, if the answer to the determination in step 140 is 'yes' and there is a confirmed peak, the method proceeds to step 142 and increments the delay points DP using the equation delay points=delay points+1. The delay points are initially set to zero. The delay points represent the number of data points taken of the cycle of the plunger since the confirmed peak. After step 142, the method proceeds to step 154 and makes a determination as to whether the differential between the baseline B and the current average force $\sigma(i)$ is greater than the expected force differential $\Delta$ The current average force $\sigma(i)$ comprises the current average force on the plunger taken over a certain number of points of the cycle up to the current point of the plunger. In one embodiment, the current average force on the plunger may be calculated based on two cycles of the plunger immediately preceding and up to the current point of the plunger. In other embodiments, the current average force on the plunger may be taken over a varied range. In one embodiment, the expected force differential $\Delta$ comprises. 15 pounds of force. In other embodiments, the expected force differential $\Delta$ may vary.

If the answer to the determination in step 154 is 'yes,' the method proceeds to step 156, confirms that an end-of-bag (EOB) or equivalent event has occurred, and proceeds through steps 146, 136, and 138 to turn on the end-of-bag alarm to indicate that air is in the chamber. This end-of-bag (EOB) event may turn off the pump. If the answer to the determination in step 154 is 'no,' the method proceeds to step 158 and makes a determination as to whether the delay points DP are greater than $\Delta$ delay point threshold. The $\Delta$ delay point threshold comprises a defined delay range, starting from the point of the trigger event, over which the differential between the baseline B and the current average force $\sigma(i)$ must exceed the expected force differential $\Delta$ in order to determine that an end-of-bag (EOB) event has occurred. In one embodiment, the $\Delta$ delay point threshold comprises 200 micro liters of delivered fluid. In other embodiments, the Δ delay point threshold may vary.

If the answer to the determination in step 158 is 'no,' the method proceeds to step 146, increments variable i using the equation i=i+1, and then proceeds back to and repeats step 136. If the answer to the determination in step 158 is 'yes,' the method proceeds to step 160, determines that there is no confirmed peak, determines that there is no end-of-bag (EOB) event, resets the delay points DP to zero, proceeds to step 146, increments variable i using the equation i=i+1, and then proceeds back to and repeats step 136. In other embodiments, one or more steps of the method 132 may be modified, not followed, or one or more additional steps may be added. Moreover, any of the variables of method 132 may be either user set, using an input device, or preset into the processor.

Figure 6:
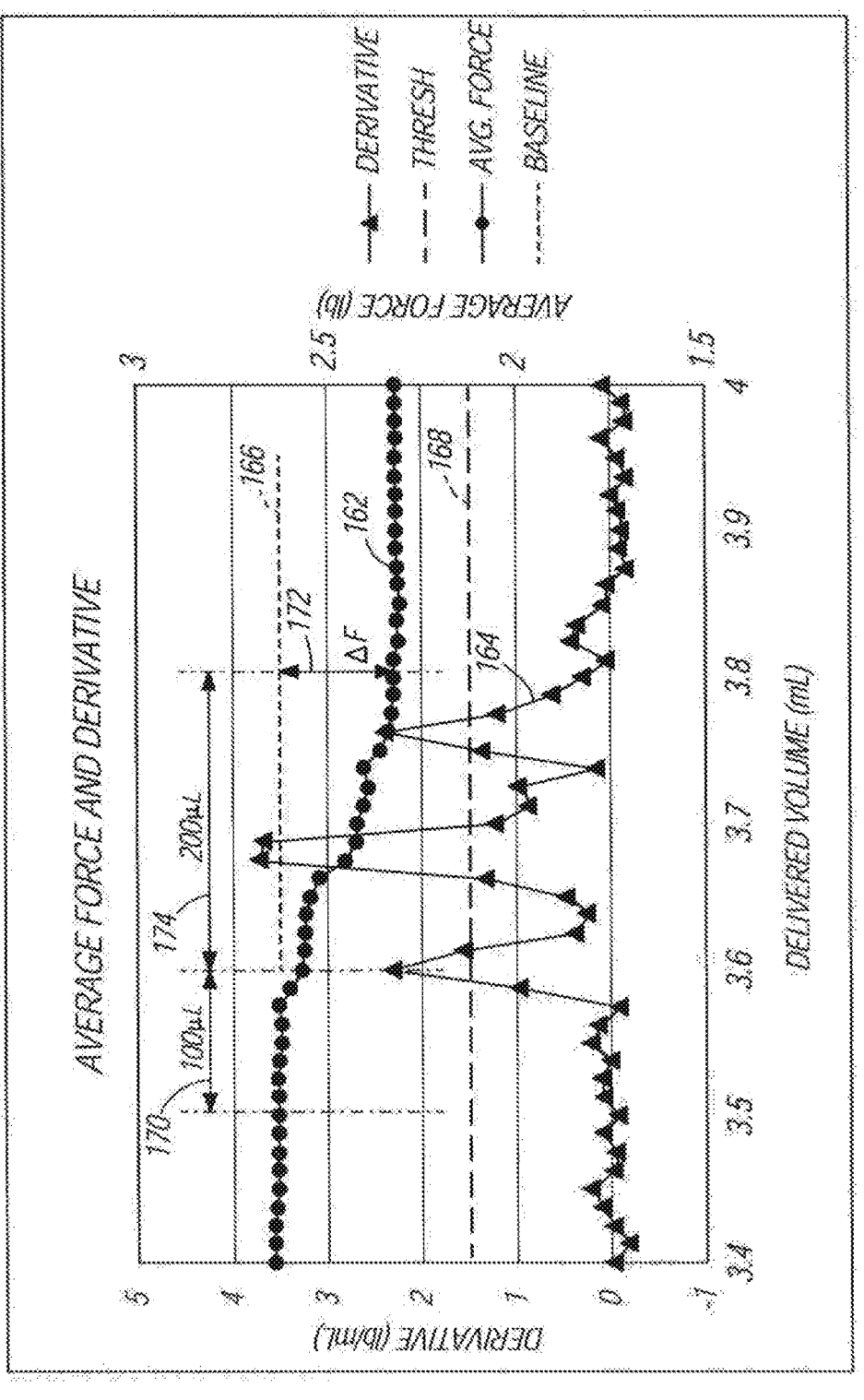
FIG. 6 illustrates a graph plotting, for a representative example, an average plunger sensor force curve, a plunger sensor force derivative curve, a baseline, a derivative threshold, a defined baseline range, an expected force differential Li, and a /:::,. delay point threshold.

FIG. 6 illustrates a graph plotting, for a representative example, an average plunger sensor force curve 162, a plunger sensor force (negative) derivative curve 164, a baseline 166, a derivative threshold 168, a defined baseline range 170, an expected force differential Δ 172, and a Δ delay point threshold 174. The right-most Y-axis represents average pounds of force on the plunger detected by a plunger force sensor, the left-most Y-axis represents a derivative (average) of the force on the plunger of FIG. 2 in pounds per milliliter, and the X-axis represents volume in milliliters of the fluid delivered from the chamber. The average plunger sensor force curve 162 comprises the average force delivered with each circle representing a measured point of the cycle of the plunger with measured data point 1 being the first circle shown in the graph. The plunger sensor force derivative curve 164 comprises the derivative force per volume delivered with each triangle representing a measured point of the cycle of the plunger with measured derivative data point 1 being the first derivative triangle shown in the graph. The baseline 166 comprises a horizontal line 166. The derivative threshold 168 comprises a horizontal line. The defined baseline range 170 comprises a horizontal distance which in this example is 100 micro liters. The expected force differential Δ 172 comprises a vertical distance. The Δ delay point threshold 174 comprises a horizontal distance which in this example is 200 micro liters.

The method of FIG. 5 may be applied to the example of FIG. 6 as follows to determine if air is contained in the chamber. In step 134, the method starts. The method then proceeds to step 136 and a determination is made that the end-of-bag (EOB) has not been detected for measured point i=1. The method then proceeds to step 140 and a determination is made that there is not a confirmed peak for measured point i=1. The method then proceeds to step 144 and a determination is made that the derivative for measured point i=1 has not exceeded the derivative threshold. The method then proceeds to step 146, increments variable i, and the method then repeats step 136. The method continues to loop in the same manner until a determination is made in step 144 that the derivative for measured point i=17 exceeds the derivative threshold. The method then proceeds to step 148 and increments variable P from O to 1. The method then proceeds to step 150 and determines that variable P which currently equals 1 is not greater than the consecutive point threshold Pih of 1. The method then proceeds to step 146, increments i to 18, and repeats steps 136, 140, and 144. In step 144, a determination in is made that the derivative of measured point i=18 exceeds the derivative threshold. The method then proceeds to step 148 and increments variable P from 1 to 2. The method then proceeds to step 150 and determines that variable P which currently equals 2 is greater than the consecutive point threshold Pth of 1. The method then proceeds to step 152, confirms a peak, and takes a baseline B for the baseline range of 100 micro liters of average force data immediately prior to and up to measured point i=17 which is the trigger event. The method then proceeds to step 146, increments variable i to 19 and proceeds back to and repeats step 136.

In step 136, a determination is made that the end-of-bag (EOB) has not been detected for measured point 19. The method then proceeds to step 140 and determines that there is a confirmed peak for measured point i=19. The method then proceeds to step 142 and increments the delay points DP to 1. The method then proceeds to step 154 and determines that the differential between the baseline B and the current average force σ(i) for measured point i=19 is not greater than the expected force differential Δ The method then proceeds to step 158 and determines that the delay points DP of 1 is not greater than the Δ delay point threshold comprising the number of measured points in the cycle of the plunger, starting from the trigger event, within 200 micro liters of fluid delivered from the chamber. The method then proceeds to step 146, increments i and proceeds back to and repeats step 136. The method continues to loop through steps 136, 140, 142, and 154 until it is determined in step 154 that the differential between the baseline B and the current average force σ(i) for measured point i=23 is greater than the expected force differential Δ The method then proceeds to step 156, confirms that an end-of-bag (EOB) event has occurred, and proceeds through steps 146, 136, and 138 to turn on the end-of-bag alarm to indicate that air is in the chamber. The end-of-bag alarm being turned on may further comprise pausing the infusion.

The method of FIG. 5 was implemented to analyze 472 data sets for a variety of flow rates. The testing resulted in no false positive determinations of air being in the chamber and only one occurrence of a false negative which only equated to 0.2% of the sets resulting in an incorrect result.

Figure 7:
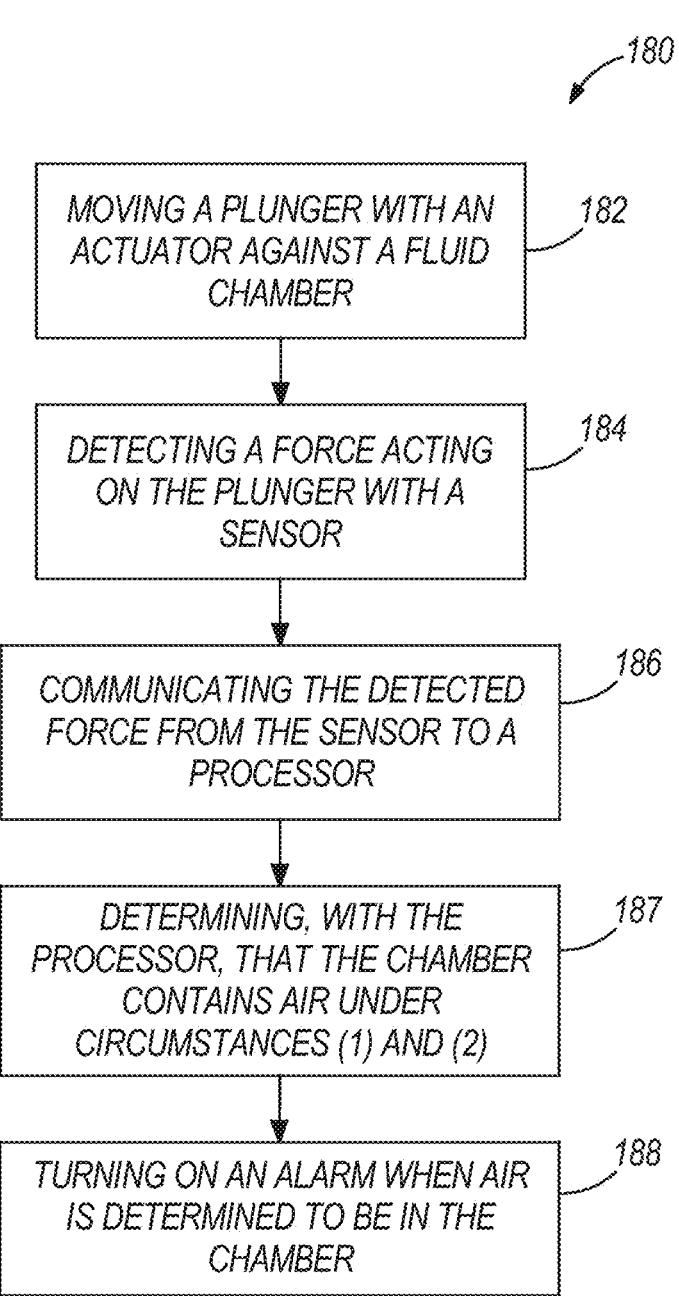
FIG. 7 illustrates a flowchart for one embodiment of a method for detecting air in a chamber of an infusion system.

FIG. 7 illustrates a flowchart for one embodiment of a method 180 for detecting air in a chamber of an infusion system. The method 180 may be implemented using the drug delivery infusion system 100 of FIG. 1 with the plunger being moved with the actuator device against the chamber containing fluid, the sensor detecting a force acting on the plunger as it moves against the chamber, the processor processing the force measurements taken by the sensor and implementing programming code stored in a non-transient memory in order to determine whether air is contained in the chamber using the algorithm set forth in method 180, and the alarm being turned on if the processor determines that air is contained in the chamber which may trigger the pump being shut down. Moreover, the method 180 may utilize the clock of the drug delivery infusion system 100 of FIG. 1 to keep time of activities of the plunger or the sensor, and may use the positional sensor to determine a position of the plunger, with each being in electronic communication with the processor. In other embodiments, the method 180 may utilize varying components to implement the method.

In step 182 a plunger is moved with an actuator device against a chamber containing fluid. In step 184 a force acting on the plunger is detected with a sensor as the plunger moves against the chamber. In step 186 a measurement of the force is electronically communicated from the sensor to a processor. In step 187 a determination is made, with the processor, that the chamber contains air when: (1) a trigger event occurs in which a change in force acting on the plunger per delivered volume of the fluid exiting the chamber exceeds a threshold; and (2) subsequent to the trigger event a differential between a baseline average force acting on the plunger and a current average force acting on the plunger exceeds an expected force differential within a defined delay range. In step 188 the processor turns on an alarm when the processor determines that the chamber contains the air. Step 188 may further comprise shutting down the pump when the alarm is turned on.

In one embodiment of step 187 step (1), which must occur for the processor to determine that the chamber contains air, may further comprise for a consecutive number of measured points of a cycle of the plunger from the trigger event the derivative force acting on the plunger per the delivered volume of the fluid exiting the chamber continuing to exceed the derivative threshold for more than a threshold number of the measured points of the cycle of the plunger against the chamber. In one embodiment of step 187 the baseline average force of step (2) may comprise the average force acting on the plunger over a defined baseline range occurring up to the trigger event. The baseline average force may further represent the chamber being filled with the fluid. In other embodiments, any of the steps of method 180 may be altered, not followed, or additional steps may be added.

In another embodiment of the disclosure, the drug delivery infusion system 100 of FIG. 1 may determine when air is present in the chamber 108 by analyzing a shape of the force profile on the plunger 107 and determining that air is contained in the chamber 108 when the shape of the force profile on the plunger 107 changes significantly from a baseline shape of a force profile representing liquid being in the chamber 108. This is because it has been discovered that when air reaches the chamber 108, the shape of the force profile on the plunger 107 during a stroke or cycle of the plunger 107 changes in a consistent manner when and after the transition is made from fluid being in the chamber 108 to air being in the chamber 108. The shape of the force profile on the plunger 107 can be used as for detecting air-in-line by discriminating the force profile shapes associated with air and fluid. The characteristics of the shape of the force profile depend on the delivery rate of the fluid being delivered from the chamber 108 with some variability related to mechanism, set, fluid type, and distal and proximal pressure.

Figures 8, 9:
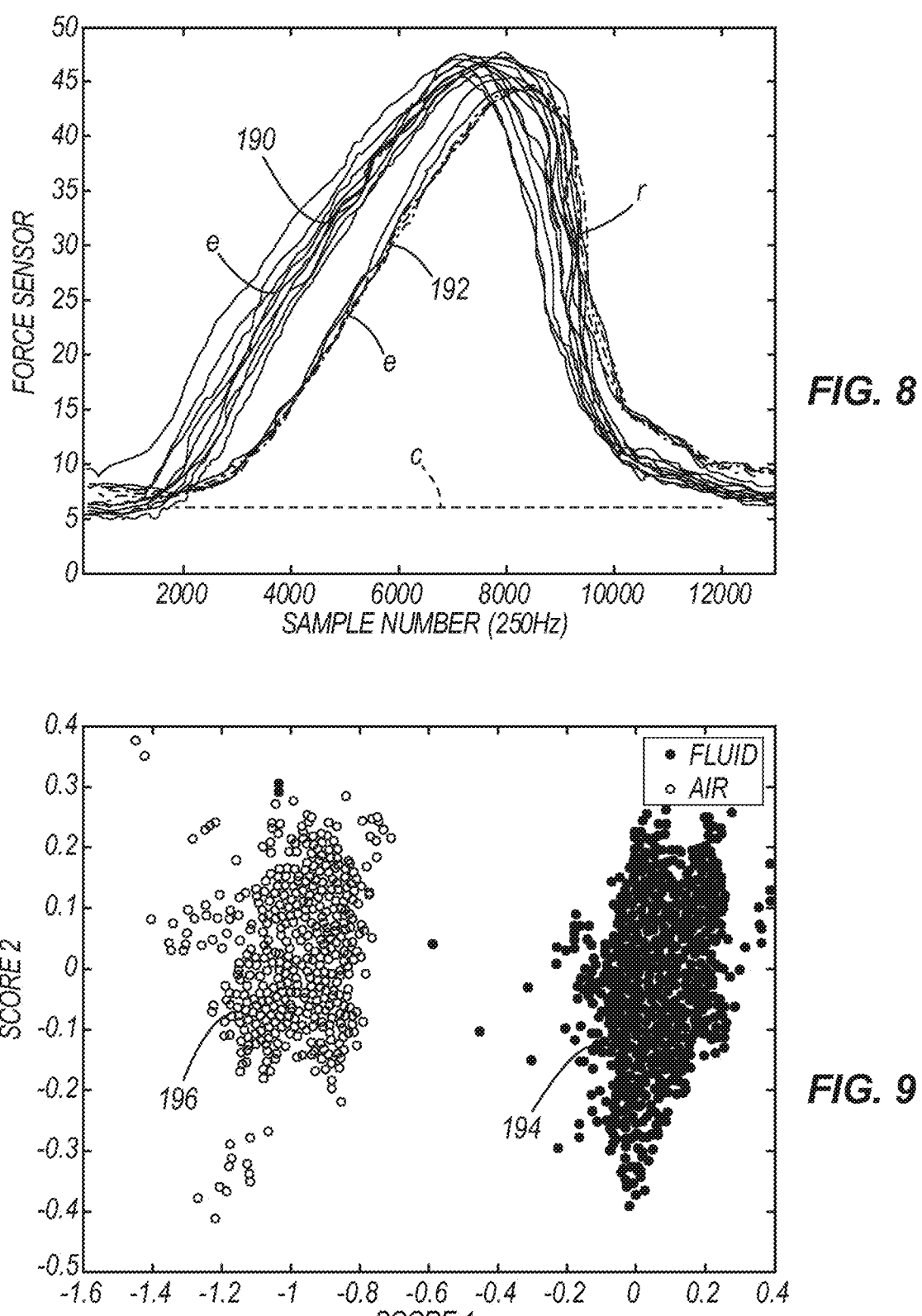
FIG. 8 illustrates a representative graph for one embodiment plotting a force sensor profile for a liquid curve and an air curve.
FIG. 9 illustrates a representative graph for one embodiment of a principal component analysis (PCA) which was done on a plunger force profile.

FIG. 8 illustrates a representative graph for one embodiment plotting a force sensor profile for a liquid curve 190 and an air curve 192. The Y-axis represents pounds of force on the plunger detected by a plunger force sensor and the X-axis represents a sample number collected at a rate of 250 Hz. Liquid curve 190 represents liquid being disposed in the chamber. Air curve 192 represents air being disposed in the chamber. As shown, the liquid curve 190 has substantially higher forces on the plunger than the air curve 192 during the expansion portion e of each cycle c of the plunger, while the difference between the curves 190 and 192 during the retraction phase r is significantly less.

FIG. 9 illustrates a representative graph for one embodiment of a principal component analysis (PCA) which was done on a plunger force profile with points 194 representing liquid being disposed in the chamber and points 196 representing air being disposed in the chamber. The X-axis represents a first score and the Y-axis represents a second score. As shown, the points 194 representing liquid being disposed in the chamber have a higher first score than the points 196 representing air being disposed in the chamber.

Figures 10, 11:
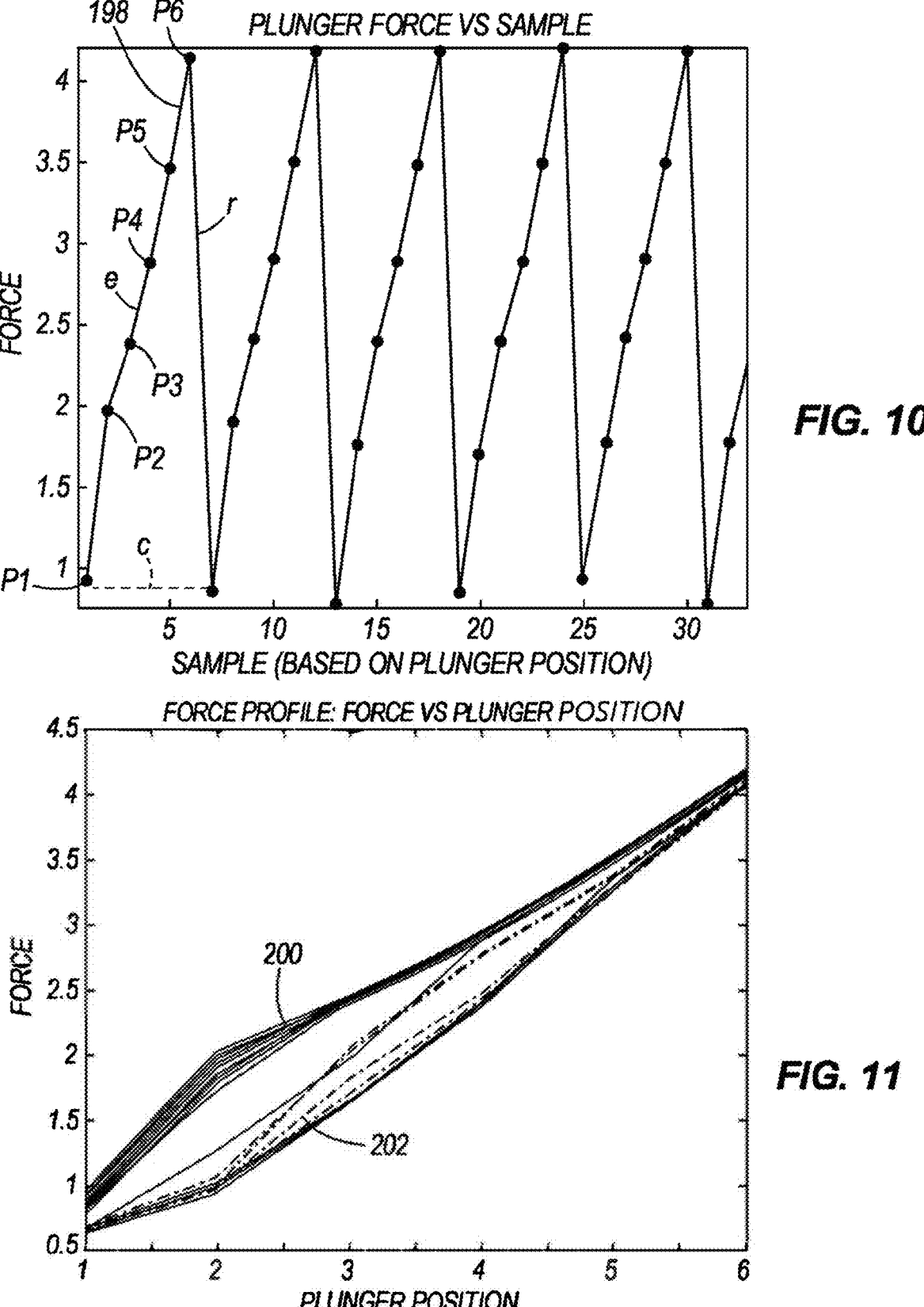
FIG. 10 illustrates a representative graph for one embodiment plotting a plunger force profile.
FIG. 11 illustrates a representative graph for one embodiment plotting a liquid plunger force curve and an air plunger force curve.

FIG. 10 illustrates a representative graph for one embodiment plotting a plunger force profile 198. The Y-axis represents pounds of force on the plunger detected by a plunger force sensor and the X-axis represents sample number for each cycle c of the plunger. As shown, six points p1-p6, comprising a 6 point vector pattern, are sampled at specific plunger positions during the expansion portion e of each cycle (or stroke) c of the plunger. No points are sampled during the retraction portion r of each cycle c of the plunger. This force sampling of each cycle may be used to determine whether air or liquid is contained in the chamber based on the shape of the measured force profile. The determination may be made using principle component analysis (PCA) to determine the correlation between the pattern variance of fluid versus air being in the chamber. Pre-processing may be applied to normalize the patterns across sets/needle heights and varying mechanisms. Separate analysis is performed for each separate fluid infusion rate or ranges of infusion rates. In other embodiments, a varying number of points per cycle of the plunger may be utilized, and the determination may be made using varying types of analysis.

FIG. 11 illustrates a representative graph for one embodiment plotting a liquid plunger force curve 200 and an air plunger force curve 202. The Y-axis represents pounds of force on the plunger detected by a plunger force sensor and the X-axis represents a sample number of a cycle of the plunger. Liquid plunger force curve 200 represents liquid being disposed in the chamber. Air plunger force curve 202 represents air being disposed in the chamber. As shown, the liquid plunger force curve 200 has substantially higher forces on the plunger than the air plunger force curve 202.

Figures 12, 13, 14:
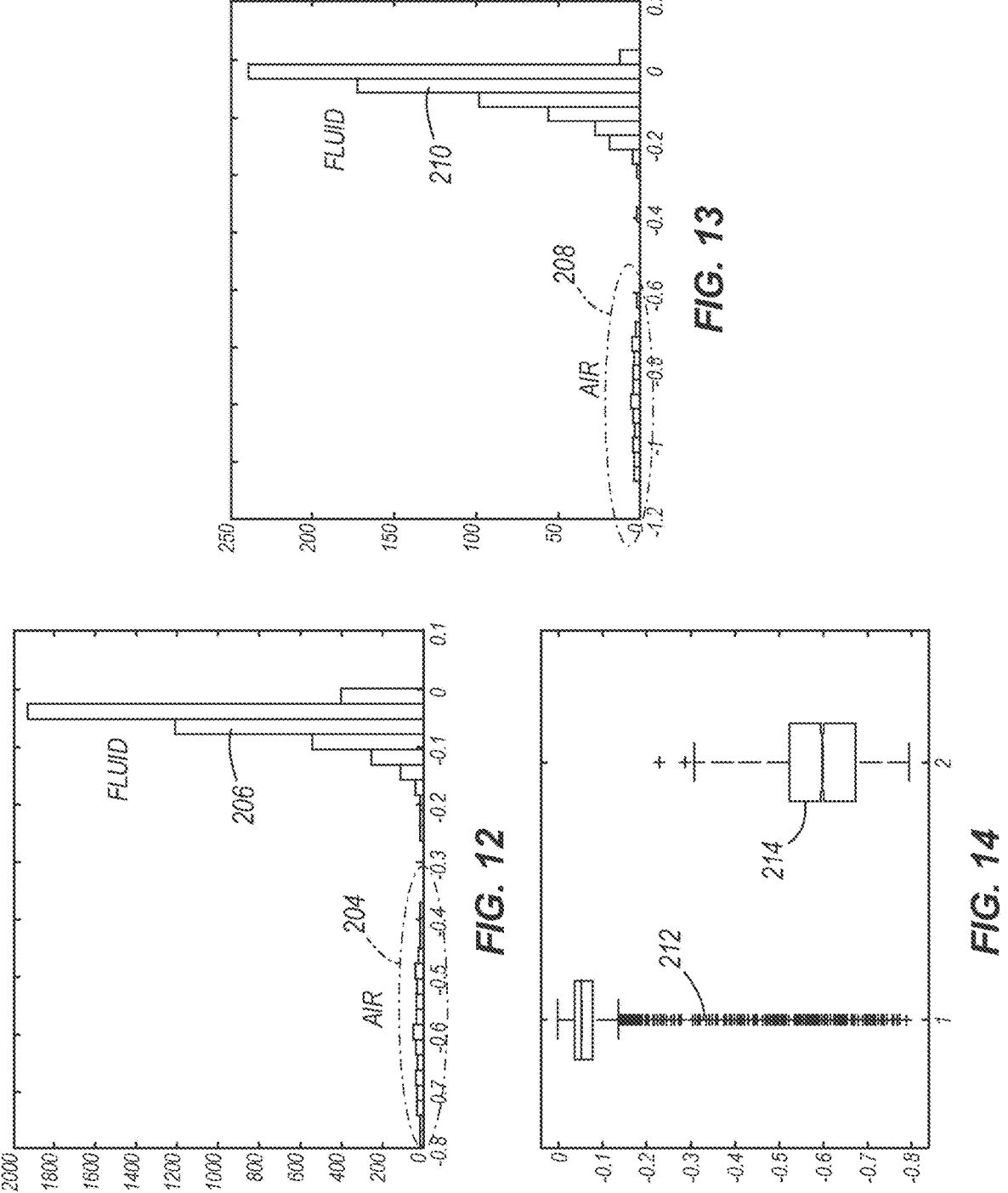
FIG. 12 illustrates a representative graph for one embodiment plotting, at an infusion rate of 20 ml/hour, the distribution of the maximum absolute difference between a reference plunger force profile and subsequent profiles comprising an air curve and a liquid curve.
FIG. 13 illustrates a representative graph for one embodiment plotting, at an infusion rate of 550 ml/hour the distribution of the maximum absolute difference between a reference plunger force profile and subsequent profiles comprising an air curve and a liquid curve.
FIG. 14 illustrates a representative graph for one embodiment plotting, at an infusion rate of 20 ml/hr, an air plot and a liquid plot.

FIG. 12 illustrates a representative graph for one embodiment plotting, at an infusion rate of 20 ml/hr, the distribution of the maximum absolute difference between a reference plunger force profile and subsequent profiles comprising an air curve 204 and a liquid curve 206. The Y-axis represents the number of profiles and the X-axis represents the difference associated with the point of the maximum absolute difference between the measured force profile and the baseline profile. Air curve 204 represents air being disposed in the chamber and liquid curve 206 represents liquid being disposed in the chamber. As shown, the liquid curve 206 has a substantially lower difference from the (liquid) baseline than the air curve 204. FIG. 13 illustrates a representative graph for one embodiment plotting, at an infusion rate of 550 ml/hr, the distribution of the maximum absolute difference between a reference plunger force profile and subsequent profiles comprising an air curve 208 and a liquid curve 210. The Y-axis represents the number of profiles and the X-axis represents the difference associated with the point of the maximum absolute difference between the measured force profile and the baseline profile. Air curve 208 represents air being disposed in the chamber and liquid curve 210 represents liquid being disposed in the chamber. As shown, the liquid curve 210 has a substantially lower difference from the (liquid) than the air curve 208. FIGS. 12 and 13 demonstrate a significant difference between air and fluid across varying infusion rates after the maximum difference calculation is applied for feature extraction.

FIG. 14 illustrates a representative graph for one embodiment plotting, at an infusion rate of 20 ml/hr air depiction 214 and liquid depiction 212. The Y axis represents the difference between the observed force and the baseline profile, and the X axis represents two groups: (1) the group of differences associated with liquid in the plunger chamber; and (2) the difference with air in the plunger chamber. Air depiction 214 represents air being disposed in the chamber and liquid depiction 212 represents liquid being disposed in the chamber. As shown, the air depiction 214 has a substantially lower (more negative) difference from the liquid baseline while the fluid 212 has a difference that is close to zero from the liquid baseline. The separation between the two groups provides the basis for a method for discriminating force measurements associated with air from those associated with fluid.

An algorithm has been discovered that normalizes a force shape profile of a plunger by determining a baseline force profile specific to each infusion program, and by using one generic feature, independent of the infusion program/rate, to assess whether air is contained in the chamber. To implement the algorithm, each force shape profile of the plunger is compared to a baseline force profile, a point-by-point difference between the force shape profile and the baseline force profile is determined, and when the minimum (most negative) difference between the force shape profile and the baseline force profile drops below a threshold a determination is made that the chamber contains air. The baseline force profile may represent liquid being in the chamber. In other embodiments, varying algorithms may be implemented to determine when air is contained in the chamber based on the force shape profile of the plunger.

Figure 15:
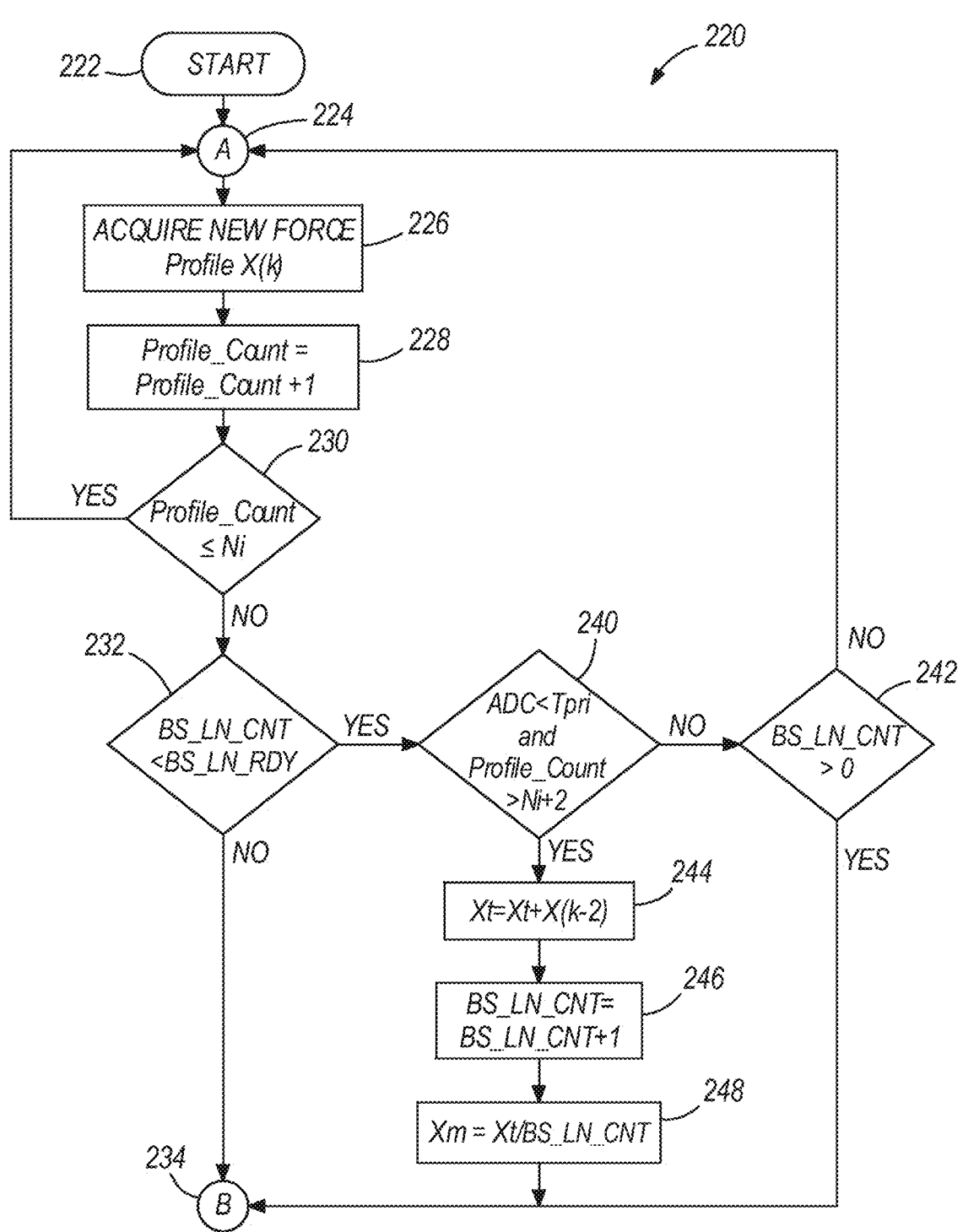
FIG. 15 illustrates one embodiment of a method, comprising a continuous flow chart, under the disclosure for determining whether air is contained in a chamber of a pump.
Figure 16:
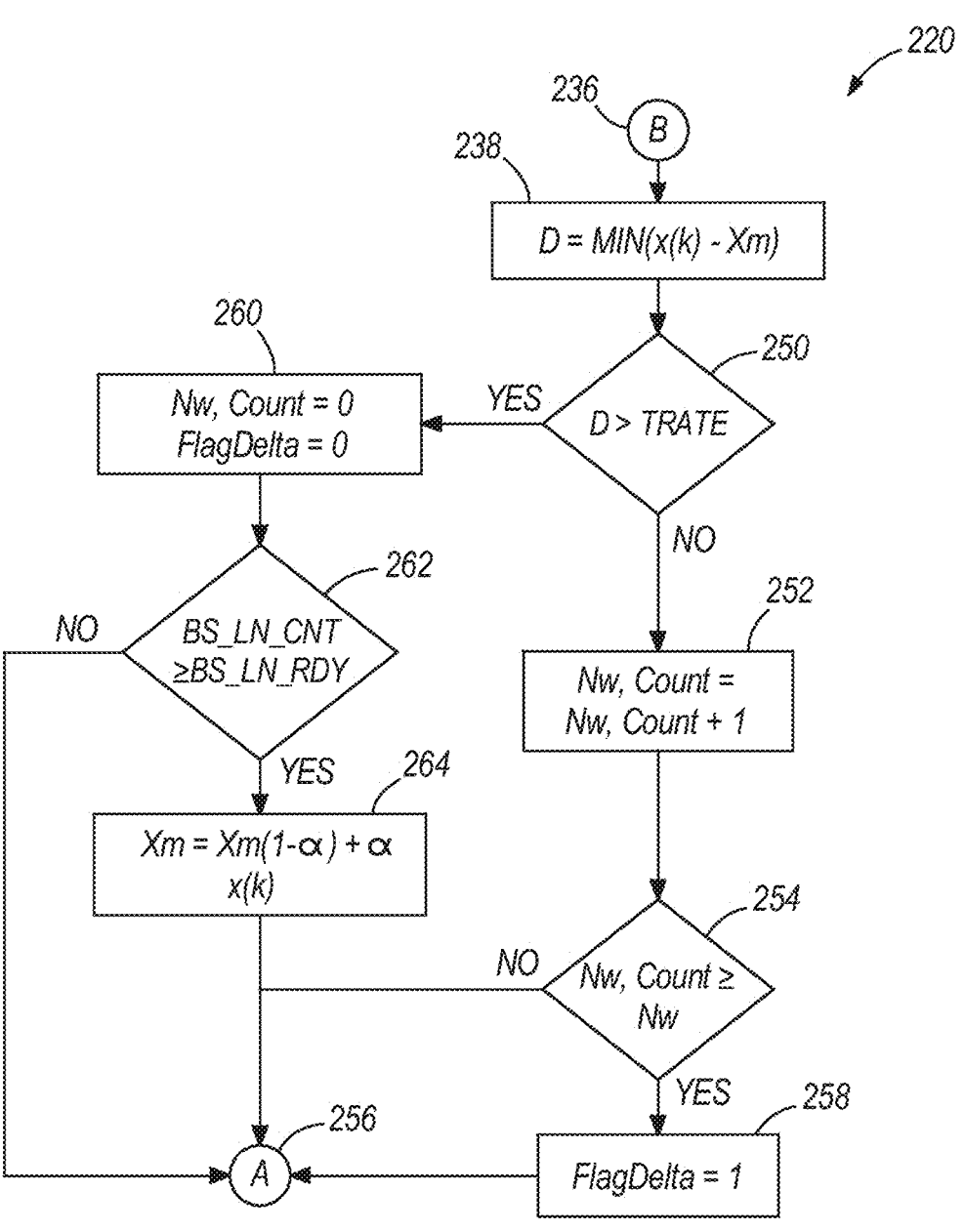
FIG. 16 illustrates a continuation of the flow chart of FIG. 15.

FIGS. 15 and 16 illustrate one embodiment of a method 220, comprising a continuous flow chart, under the disclosure for determining whether air is contained in a chamber of a pump. The method 220 may be implemented using the drug delivery infusion system 100 of FIG. 1 with the plunger being moved with the actuator device against the chamber containing fluid, the sensor detecting a force acting on the plunger as it moves against the chamber, the processor processing the force measurements taken by the sensor and implementing programming code stored in a non-transient memory in order to determine whether air is contained in the chamber using the algorithm set forth in method 220, and the alarm being turned on if the processor determines that air is contained in the chamber which may further shut down the pump. Moreover, the method 220 may utilize the clock of the drug delivery infusion system 100 of FIG. 1 to keep time of activities of the plunger or the sensor, and may use the positional sensor to determine a position of the plunger. In other embodiments, the method 220 may utilize varying components to implement the method.

In step 222, the method starts. After step 222, the method proceeds through location step 224 to step 226. In step 226, a force profile X(k) of the plunger is acquired for the first cycle of the plunger with k=1 representing the first cycle of the plunger. The force profile X(k) comprises a vector comprising the six forces on the plunger at each of the six positions/points of the plunger during the k cycle of the plunger. In other embodiments, the force profile may be acquired with a varying number of positions of the plunger. The method then proceeds to step 228 and increments the profile count PC using the equation PC=PC+1 with PC initially being 0 the first time through so that PC will be incremented to 1. The method then proceeds to step 230 and determines whether the profile count PC is less than or equal to the number of initial cycles of the plunger to ignore Ni which is set to Ni=2. In other embodiments, Ni may be set to other values.

If step 230 determines that the profile count PC is less than or equal to the number of initial cycles of the plunger to ignore Ni then the method proceeds back to and repeats steps 224, 226, 228, and 230 until the profile count PC is not less than or equal to the number of initial cycles of the plunger to ignore Ni at which point the method proceeds to step 232. In step 232 a determination is made as to whether the baseline count BS_LN_CNT is less than the baseline ready variable BS_LN_RDY. The baseline count BS_LN_CNT is initially set to BS_LN_CNT=0. The baseline ready variable BS_LN_RDY is set to BS_LN_RDY=5. In other embodiments, BS_LN_CNT and BS_LN_RDY may be set to other values. If step 232 determines that BS_LN_CNT is not less than BS_LN_RDY than the method proceeds through step 234 of FIG. 15, through step 236 of FIG. 16, to step 238 of FIG. 16 which is discussed later on.

If in step 232 a determination is made that the baseline count BS_LN_CNT is less than BS_LN_RDY_than the method proceeds to step 240. In step 240 a determination is made as to whether the Analog-To-Digital-Count (ADC) at that instant is less than the primary threshold for fluid TPRI, and as to whether the profile count PC is greater than the number of initial cycles of the plunger to ignore plus 2 represented by PC being greater than Ni+2. The primary threshold for fluid TPRI is set to 3,000. In other embodiments, the primary threshold for fluid TPRI may be set to other values. If the determination in step 240 is made that either the Analog-To-Digital-Count (ADC) read by an air sensor downstream of the chamber is not less than the primary threshold for fluid TPRI (which means that air is in the chamber), or that the profile count PC is not greater than the number of initial cycles of the plunger to ignore plus 2 (there is a lag of 2 cycles due to the air sensor being located downstream of the chamber) represented by PC being greater than Ni+2, than the method proceeds to step 242, and determines whether the baseline count BS_LN_CNT is greater than 0. In other embodiments, the lag number of cycles used may vary. If step 242 determines that the baseline count BS_LN_CNT is not greater than 0 then the method proceeds back to location step 224 to step 226 and continues the loop. If step 242 determines that the baseline count BS_LN_CNT is greater than 0 then the method proceeds through location step 234 of FIG. 15, through location step 236 of FIG. 16, to step 238 of FIG. 16 which is discussed later on.

If in step 240 the determination is made that the Analog-To-DigitalCount (ADC) read by an air sensor downstream of the chamber is less than the primary threshold for fluid TPRI (which means that liquid is in the chamber), and that the profile count PC is greater than the number of initial cycles of the plunger to ignore plus 2 (indicating that the lag of 2 cycles, due to the air sensor being located downstream of the chamber, has been completed) represented by PC being greater than Ni+2, then the method proceeds to step 244. In step 244, the accumulated baseline profile Xt is determined using the equation Xt=Xt+X(k−2) (wherein X(k−2) represents the force profile, expressed as a six point vector, for 2 cycles ago due to the air sensor being located downstream of the chamber) wherein Xt is initially set to 0 and k represents the number of the current cycle of the plunger. In other embodiments, the equation for Xt may be varied. After step 244, the method proceeds to step 246 and increments the baseline count BS_LN_CNT using the equation BS_LN_CNT=BS_LN_CNT+1. After step 246, the method proceeds to step 248 and determines the baseline force profile Xm, expressed as a 6 point vector, using the equation Xm=Xt I BS_LN_CNT which averages the force measurements on the plunger taken at times when liquid is in the chamber over the number of baseline count BS_LN_CNT cycles of the plunger. The baseline force profile Xm represents the baseline force vector for a situation in which liquid (fluid) is contained in the chamber 2 cycles prior to the current cycle due to the air sensor being located downstream of the chamber. In other embodiments, the baseline force profile Xm may be calculated using varying equations. After step 248, the method proceeds through location step 234 of FIG. 15, through location step 236 of FIG. 16, to step 238 of FIG. 16.

In step 238 of FIG. 16, the minimum distance D between the current vector force profile of the plunger and the baseline force vector is determined using the equation D=min(X(k)−Xm) where k represents the current cycle of the plunger and Xm represents the baseline force vector with D being the single minimum distance between the corresponding 6 points of the two vectors. After step 238, the method proceeds to step 250 and determines whether D is greater than a threshold for a given infusion rate Trate which is set to −0.3. In other embodiments, Trate may be set to a varying number depending on the infusion rate or other factors, such as the signal variance. Additionally, more than one value for Trate may be used to provide regions of high probability versus low probability. If a determination is made in step 250 that the minimum distance D between the current vector force profile of the plunger and the baseline force vector is not greater than the threshold for a given infusion rate Trate, which indicates that air is in the chamber, then the method proceeds to step 252.

In step 252, Nw count is incremented using the equation Nw count=Nw count+1 with Nw count initially set to 0. Nw count represents the current number of observed air cycles. After step 252, the method proceeds to step 254 and determines whether Nw count is greater than or equal to Nw with Nw representing the threshold number of consecutive observed air cycles of the plunger after which an air alarm will be turned on indicating that air is contained in the chamber. If a determination is made in step 254 that Nw count is not greater than or equal to Nw than the method proceeds through location step 256 back to location step 224 of FIG. 15 to step 226 of FIG. 15 and repeats the loop. If a determination is made in step 254 that Nw count is greater than or equal to Nw than the method proceeds to step 258, sets FlagDelta to 1 indicating that air is present in the chamber, turns on an alarm to indicate that air is present in the chamber, and proceeds through location step 256 back to location step 224 of FIG. 15 to step 226 of FIG. 15 and repeats the loop. Step 258 may further comprise shutting down the pump.

If a determination is made in step 250 that the minimum distance D between the current vector force profile of the plunger and the baseline force vector is greater than the threshold for a given infusion rate Trate, indicating that liquid is contained in the chamber, then the method proceeds to step 260. In step 260, Nw, count is reset to 0 with Nw, count representing the current number of observed air cycles, and FlagDelta is also reset to 0 with FlagDelta representing that air is present in the chamber. After step 260, the method proceeds to step 262 and determines whether the baseline count BS_LN_CNT is greater than or equal to the baseline ready variable BS_LN_RDY which is set to BS_LN_ROY=5. In other embodiments, the baseline ready variable BS_LN_RDY may be set to other values.

If a determination is made in step 262 that the baseline count BS_LN_CNT is not greater than or equal to the baseline ready variable BS_LN_RDY then the method proceeds through location step 256 back to location step 224 of FIG. 15 to step 226 of FIG. 15 and repeats the loop. If a determination is made in step 262 that the baseline count BS_LN_CNT is greater than or equal to the baseline ready variable BS_LN_RDY then the method proceeds to step 264. In step 264 the baseline force profile Xm, expressed as a 6 point vector, is calculated using an adaptive baseline force profile equation Xm=Xm*(1−α)+α*X(k) wherein a comprises a forgetting rate which determines what percentage of the calculated baseline force profile Xm comprises the preceding calculated baseline force profile Xm and what percentage of the baseline force profile Xm comprises the current force profile X(k) where X(k) is the current force profile of the plunger for the k cycle of the plunger. In one embodiment the forgetting rate a may be set to 0.1. In other embodiments, the forgetting rate a may be set to varying values. The adaptive baseline may be determined in alternate manners such as a moving average or Kalman filter.

Step 264 comprises an adaptive baseline step which allows the user to assert control over the baseline force profile Xm by controlling the forgetting rate α. In other embodiments, the forgetting rate a may be pre-programmed. In still other embodiments, varying ways may be used to calculate the baseline force profile Xm. After step 264 the method proceeds through location step 256 back to location step 224 of FIG. 15 to step 226 of FIG. 15 and repeats the loop. In other embodiments, one or more steps of the method 220 may be modified, not followed, or one or more additional steps may be added. Moreover, any of the variables of the method 220 may be either user set, using an input device, or pre-set into the processor.

FIG. 17 illustrates a representative graph for one embodiment plotting a force sensor profile 266. The Y-axis represents pounds of force on the plunger detected by a plunger force sensor and the X-axis represents time in seconds. Six points p1-p6 are calculated during the expansion portion e of each cycle c of the plunger. No points are sampled during the retraction portion r of each cycle c of the plunger. Line 268 represents the point, during the forty-fifth cycle of the plunger, at which an air alarm is turned on due to air being in the chamber when the method 220 of FIGS. 15 and 16 is applied which is discussed more thoroughly below.

FIG. 18 illustrates a graph plotting for each cycle c of the plunger of FIG. 17 six respective difference points dp representing the measured differences between a baseline, comprising liquid being in the chamber, and the corresponding points of each respective cycle of the plunger. The Y-axis represents the differences and the X-axis represents time. The circled points cp represent the minimum difference for each cycle of the plunger between the six respective difference points dp of each cycle of the plunger and the baseline. Line 270 represents the threshold for a given infusion rate Trate which is set to −0.3. As discussed more thoroughly below, when the method 220 of FIGS. 15 and 16 is applied, the method determines that liquid is contained in the chamber during the first forty-three cycles of the plunger, determines that air is in the chamber during the forty-fourth cycle of the plunger, and after line 268, as it does in FIG. 17, turns on an air alarm during the forty-fifth cycle of the plunger representing that air is in the chamber.

FIG. 19 illustrates a graph plotting the first six full cycles C1-C6 of the force sensor profile 266 of FIG. 17. The Y-axis represents pounds of force on the plunger detected by a plunger force sensor and the X-axis represents time in seconds. Six points p1-p6 are calculated during the expansion portion e of each cycle c of the plunger. No points are sampled during the retraction portion r of each cycle c of the plunger.

FIG. 20 illustrates a graph plotting for each of the first six full cycles C1-C6 of the plunger of FIG. 18 six respective difference points dp representing the measured differences between a baseline, comprising liquid being in the chamber, and the corresponding points of each respective cycle of the plunger. The Y-axis represents the differences and the X-axis represents time. The circled points cp represent the minimum difference for each cycle of the plunger between the six respective difference points dp of each cycle of the plunger and the baseline. Line 270, as it does in FIG. 18, represents the threshold for a given infusion rate Trate which is set to −0.3. As discussed more thoroughly below, when the method of FIGS. 15 and 16 is applied the method determines that liquid is contained in the chamber during each of the first six full cycles C1-C6 of the plunger.

FIG. 21 illustrates a graph plotting the forty-second through forty-fifth cycles C42-C45 of the force sensor profile 266 of FIG. 17. The Y-axis represents pounds of force on the plunger detected by a plunger force sensor and the X-axis represents time in seconds. Six points p1-p6 are calculated during the expansion portion e of each cycle c of the plunger. No points are sampled during the retraction portion r of each cycle c of the plunger.

FIG. 22 illustrates a graph plotting for the forty-second through forty fifth cycles C42-C45 of the plunger of FIG. 18 six respective difference points dp representing the measured differences between a baseline, comprising liquid being in the chamber, and the corresponding points of each respective cycle of the plunger. The Y-axis represents the differences and the X-axis represents time. The circled points cp represent the minimum difference for each cycle of the plunger between the six respective difference points dp of each cycle of the plunger and the baseline. Line 270, as it does in FIGS. 18 and 20, represents the threshold for a given infusion rate Trate which is set to −0.3. As discussed more thoroughly below, when the method 220 of FIGS. 15 and 16 is applied, the method determines that liquid is contained in the chamber during the first forty-three cycles of the plunger, determines that air is in the chamber during the forty-fourth cycle of the plunger, and after line 268, as it does in FIG. 17, turns on an air alarm during the forty-fifth cycle of the plunger representing that air is in the chamber.

The method 220 of FIGS. 15 and 16 will now be applied to the example of FIGS. 17-22 to demonstrate how the method works. In the interest of efficiency, only some of the steps of the method 220 are described below. When the method 220 of FIGS. 15 and 16 is applied to the example of FIGS. 17-22, the first two cycles C1 and C2 are skipped because the profile count PC of 1 and 2 respectively is less than or equal to Ni=2. The force profiles X(k) for the third and fourth cycles C3 and C4 are acquired but not used because the profile count PC of 3 and 4 respectively is not greater than the number of initial cycles of the plunger to ignore (Ni=2) plus 2 represented by PC being greater than 4 (Ni+2=2+2=4). When the profile count PC reaches 5 at the fifth cycle C5, the accumulated baseline profile Xt is determined because the measured ADC of 1,673 is less than the primary threshold for fluid TPRI of 3,000, and the profile count PC=5 is greater than 4 (Ni+2=2+2=4). At this point in time, the baseline force profile Xm, expressed as a six point vector, is calculated using the equation Xm=Xt I BS_LN_CNT wherein Xt=Xt [which is initially set to 0]+X (k−2)=0+X(5−2)=0+X(3)=X(3) [representing the force profile for the third cycle] and BS_LN_CNT=BS_LN_CNT [which is initially set to 0]+1=0+1=1. Applying this equation results in the baseline force profile, expressed as a six point force vector, being Xm=(0.574252, 1.192627, 1.990768, 2.551261, 3.144921, 3.823651). The method 220 then determines the minimum distance D between the current vector force profile X(k), where k=5, of the plunger and the baseline force vector using the equation D=min(X(k)−Xm) =min(X(5)−Xm)=min((0.601876, 1.226866, 1.968040, 2.542253, 3.058266, 3.787412)−(0.574252, 1.192627, 1.990768, 2.551261, 3.144921, 3.823651))=min ((0.601876−0.574252), (1.226866−1.192627), (1.968040−1.990768), (2.542253−2.551261), (3.058266−3.144921), (3.787412−3.823651))=min(0.027624, 0.034239, −0.022728, −0.009008, −0.086655, −0.036239)=−0.086655. Because D=−0.086655 is greater than Trate=−0.3, the method determines that the current cycle/profile is for liquid being in the chamber, and the adaptive baseline, using the forgetting rate a, is not applied because the baseline count BS_LN_CNT=1 is not greater than or equal to the baseline ready variable BS_LN_RDY=5.

For the sixth cycle C6 the profile count PC increases to 6 and the accumulated baseline profile Xt is determined because the measured ADC of 1,740 is less than the primary threshold for fluid TPRI of 3,000, and the profile count PC=6 is greater than 4 (Ni+2=2+2=4). At this point in time, the baseline force profile Xm, expressed as a six point vector, is calculated using the equation Xm=Xt I BS_LN_CNT wherein Xt=Xt+X(k−2) and BS_LN_CNT=2. Applying this equation results in the baseline force profile, expressed as a six point force vector, being Xm=(0.584984, 1.234167, 1.947920, 2.556566, 3.103720, 3.818871). The method 220 then determines the minimum distance D between the current vector force profile X(k), where k=6, of the plunger and the baseline force vector using the equation D=min(X(k)− Xm)=min(X(6)−Xm)=min((0.600387, 1.266444, 1.916179, 2.547273, 3.031686, 3.805076)−(0.584984, 1.234167, 1.947920, 2.556566, 3.103720, 3.818871−))=min ((0.600387−0.584984), (1.266444−1.234167), (1.916179− 1.947920), (2.547273−2.556566), (3.031686−3.103720), (3.805076−3.818871))−min (0.015403, 0.03227, −0.031741, −0.009293, −0.072034, −0.013795)=−0.072035. Because D=−0.072035 is greater than Trate=−0.3, the method determines that the current cycle/profile is for liquid being in the chamber, and the adaptive baseline, using the forgetting rate α, is not applied because the baseline count BS_LN_CNT=2 is not greater than or equal to the baseline ready variable BS_LN_RDY=5.

When the method reaches the forty-third cycle C43 (the intermediate cycle calculations are not described here in the interest of efficiency) the profile count PC increases to 43 and the accumulated baseline profile Xt is determined because the measured ADC is less than the primary threshold for fluid TPRI of 3,000, and the profile count PC=43 is greater than 4 (Ni+2=2+2=4). At this point in time, the baseline force profile Xm, expressed as a six point vector, is calculated using the equation Xm=Xt I BS_LN_CNT wherein Xt=Xt+X(k−2) and BS_LN_CNT=39. Applying this equation results in the baseline force profile, expressed as a six point force vector, being Xm=(0.507904, 0.882215, 1.642329, 2.326609, 2.893227, 3.623199). The method 220 then determines the minimum distance D between the current vector force profile X(k), where k=43, of the plunger and the baseline force vector using the equation D=min(X (k)−Xm)=min(X(43)−Xm)=min((0.521021, 0.729376, 1.515777, 2.249448, 2.828867, 3.582641)−(0.507904, 0.882215, 1.642329, 2.326609, 2.893227, 3.623199))=min ((0.521021−0.507904), (0.729376−0.882215), (1.515777− 1.642329), (2.249448−2.326609), (2.828867−2.893227), (3.582641−3.623199))=min(0.013117, −0.152839, −0.126552, −0.077161, −0.064360, −0.040558)=−0.152839. Because D=−0.152839 is greater than Trate=−0.3, the method determines that the current cycle/profile is for liquid being in the chamber, and the adaptive baseline, using the forgetting rate α, is determined because the baseline count BS_LN_CNT=39 is greater than or equal to the baseline ready variable BS_LN_RDY=5. Applying the forgetting rate α=0.100000 to calculate the adaptive baseline results in the adaptive baseline Xm=Xm*(1−α)+α*X(k)=(0.509216, 0.866931, 1.629673, 2.318893, 2.886791, 3.619144).

When the method reaches the forty-fourth cycle C44 the profile count PC increases to 44 and the accumulated baseline profile Xt is determined because the measured ADC is less than the primary threshold for fluid TPRI of 3,000, and the profile count PC=44 is greater than 4 (Ni+2=2+2=4). At this point in time, the baseline force profile Xm, expressed as a six point vector, is calculated using the equation Xm=Xt I BS_LN_CNT wherein Xt=Xt+X(k−2) and BS_LN_CNT=40. Applying this equation results in the baseline force profile, expressed as a six point force vector, being Xm=(0.509216, 0.866931, 1.629673, 2.318893, 2.886791, 3.619144). The method 220 then determines the minimum distance D between the current vector force profile X(k), where k=44, of the plunger and the baseline force vector using the equation D=min(X(k)−Xm)=min(X (44)−Xm)=min((0.616675, 0.690732, 0.974907, 1.446447, 2.064309, 3.097704)−(0.509216, 0.866931, 1.629673, 2.318893, 2.886791, 3.619144))=min((0.616675− 0.509216), (0.690732−0.866931), (0.974907−1.629673), (1.446447−2.318893), (2.064309−2.886791), (3.097704− 3.619144))=min(0.107459, −0.176199, −0.654767, −0.872446, −0.822482, −0.5214390.521440)=−0.872446. Because D=−0.872446 is not greater than Trate=−0.3, the method determines that the current cycle/profile is for air being in the chamber and increments Nw, count to Nw, count+1=0+1=1.

When the method reaches the forty-fifth cycle C45 the profile count PC increases to 45 and the accumulated baseline profile Xt is determined because the measured ADC is less than the primary threshold for fluid TPRI of 3,000, and the profile count PC=45 is greater than 4 (Ni+2=2+2=4). At this point in time, the baseline force profile Xm, expressed as a six point vector, is calculated using the equation Xm=Xt I BS_LN_CNT wherein Xt=Xt+X(k−2) and BS_LN_CNT=41. Applying this equation results in the baseline force profile, expressed as a six point force vector, being Xm=(0.509216, 0.866931, 1.629673, 2.318893, 2.886791, 3.619144). The method 220 then determines the minimum distance D between the current vector force profile X(k), where k=45, of the plunger and the baseline force vector using the equation D=min(X(k)−Xm)=min(X (44)−Xm)=min((0.613084, 0.674059, 0.891756, 1.421075, 1.990083, 2.859728)−(0.509216, 0.866931, 1.629673, 2.318893, 2.886791, 3.619144))=min((0.613084− 0.509216), (0.674059 0.866931) (0.674059−0.866931), (0.891756−1.629673), (1.421075−2.318893), (1.990083− 2.886791), (2.859728−3.619144))=min(0.103868, −0.192872, −0.737917, −0.897818, −0.896708, −0.7594150.759416)=−0.897818. Because D=−0.897818 is not greater than Trate=−0.3, the method determines that the current cycle/profile is for air being in the chamber, increments Nw, count to Nw, count+1=1+1=2, sets FlagDelta=1, and signals an air alarm indicating that air is in the chamber.

The method of FIGS. 15 and 16 was implemented to analyze a large number of data sets for a variety of flow rates. The testing resulted in no false negative occurrences.

FIG. 23 illustrates a flowchart for one embodiment of a method 280 for detecting air in a chamber of an infusion system. The method 280 may be implemented using the drug delivery infusion system 100 of FIG. 1 with the plunger being moved with the actuator device against the chamber containing fluid, the sensor detecting a force acting on the plunger as it moves against the chamber, the processor processing the force measurements taken by the sensor and implementing programming code stored in a non-transient memory in order to determine whether air is contained in the chamber using the algorithm set forth in method 280, and the alarm being turned on if the processor determines that air is contained in the chamber which may trigger the pump being shut down. Moreover, the method 280 may utilize the clock of the drug delivery infusion system 100 of FIG. 1 to keep time of activities of the plunger or the sensor, and may use the positional sensor to determine a position of the plunger, with each being in electronic communication with the processor. In other embodiments, the method 280 may utilize varying components to implement the method.

In step 282 a plunger is moved, with an actuator device, acting against a chamber containing fluid. In step 284, a sensor is used to detect a force acting on the plunger as it moves against the chamber. In step 286 a measurement of the force is electronically communicated from the sensor to a processor. In step 288 the processor determines: (1) a baseline force profile; (2) a current force profile representing the current force acting on the plunger against the chamber; (3) a difference between the current force profile and the baseline force profile; and (4) that the chamber contains air when the calculated difference crosses a threshold. In step 290 the processor turns on an alarm when the processor determines that the chamber contains the air. Step 290 may further comprise shutting down the pump when the alarm is turned on.

In one embodiment, the baseline force profile represents the chamber being filled with the fluid. In another embodiment, the processor determines the baseline force profile by taking force measurements at a plurality of plunger positions over a cycle of the plunger against the chamber. In an additional embodiment, the processor determines the baseline force profile by averaging force measurements taken over a plurality of cycles of the plunger against the chamber. In yet another embodiment, the processor determines the baseline force by additionally taking into account the current force profile acting on the plunger during a current cycle of the plunger against the chamber.

In still another embodiment, the processor further applies a forgetting rate, moving average or Kalman filter which controls what portion of the updated baseline force profile is made up of the average or estimated baseline force measurements and what portion of the updated baseline force profile is made up of the current force profile. In an additional embodiment, the processor determines the current force profile by taking force measurements at a plurality of plunger positions over a current cycle of the plunger against the chamber. In another embodiment, the processor calculates the difference between the current force profile and the baseline force profile by calculating respective differences between a plurality of points of the current force profile relative to a respective plurality of points of the baseline force profile, and determining a minimum difference of the respective differences or an absolute maximum difference of the respective differences. In an additional embodiment, the processor determines that the chamber contains the air when the minimum difference is less than the threshold. In still another embodiment, the processor determines that the chamber contains the air when the calculated difference is below the threshold. In other embodiments, any of the steps of the method 280 may be altered, not followed, or additional steps may be added.

FIG. 24 illustrates one embodiment of a method 300, comprising a continuous flow chart, under the disclosure for determining whether air is contained in a chamber of a pump based upon a shape of the plunger force profile. The method 300 may be implemented using the drug delivery infusion system 100 of FIG. 1 with the plunger being moved with the actuator device against the chamber containing fluid, the sensor detecting a force acting on the plunger as it moves against the chamber, the processor processing the force measurements taken by the sensor and implementing programming code stored in a non-transient memory in order to determine whether air is contained in the chamber using the algorithm set forth in method 300, and the alarm being turned on if the processor determines that air is contained in the chamber which may trigger the pump being shut down. Moreover, the method 300 may utilize the clock of the drug delivery infusion system 100 of FIG. 1 to keep time of activities of the plunger or the sensor, and may use the positional sensor to determine a position of the plunger. In other embodiments, the method 300 may utilize varying components to implement the method.

In step 302, the method 300 starts. After step 302, the method proceeds through location step 304 to step 306. In step 306 a force profile over one cycle of a plunger of the chamber is acquired using the sensor. In one embodiment, as shown in box 308, the sampling frequency may be 62.5 Hz. In other embodiments, varying parameters may be used. After step 306, the method proceeds to step 310 and re-samples the force profile for the cycle of the plunger at uniform increments with respect to position or at specific positions. In one embodiment, as shown in box 312, the re-sampling may take place over a set of angles and may be performed using linear, quadratic or cubic interpolation. In other embodiments, varying parameters may be used. After step 310, the method proceeds to step 314 and selects a sub-set of angles (i.e. one or more ranges). In one embodiment, as shown in box 316, the sub-set of angles may comprise a range of angles based on the infusion rate. In other embodiments, varying parameters may be used. After step 314, the method proceeds to step 318 and calculates a derivative. In one embodiment, as shown in box 320, this step may comprise simultaneously applying a smoothing operation. In other embodiments, this step may comprise applying varying parameters. Steps 306 through 318 comprise acquisition and preprocessing steps.

After step 318, the method proceeds to step 322 and calculates scores using the equation S=D*M where D comprises the derivative and M comprises a set of N eigenvectors by infusion rate, as shown in box 324, calculated using principal component analysis. In one embodiment, N=8. In other embodiments, the scores may be calculated using varying parameters. After step 322, the method proceeds to step 326 and applies a linear determinate analysis to calculate L=S*W where L represents the linear determinate result, S represents the scores, and W, as shown in box 328, represents weights of the linear discriminate analysis. In one embodiment, as shown in box 328, this step may also consider class means by infusion rate. In other embodiments, varying parameters may be used. After step 326, the method proceeds to step 330 and determines a classification based on the result of the linear discriminate analysis. This step may also consider class means by infusion rate as shown in box 328. After step 330, the method proceeds to step 332 and determines whether air is in the chamber based on the classification. If step 332 determines that air is contained in the chamber then the method proceeds to step 334 and sounds an air alarm during which the pump may be shut down. If step 332 determines that air is not in the chamber based on the classification then the method proceeds back to location step 304.

In an alternative embodiment, instead of steps 322 and steps 326 a linear determinate analysis may be conducted, as shown in box 336, using the equation L=D*(M*W)–D*P wherein P=M*W and the variables are identical to those described above. In another alternative embodiment, instead of steps 306 through steps 318, preprocessing steps 338, 340, 342, 344, and 346 may be followed. In step 338, a force profile of the plunger over one cycle of a plunger of the chamber is acquired using the sensor. In one embodiment, as shown in box 308, the sampling frequency may be 62.5 Hz. In other embodiments, varying parameters may be used. In step 340, a low pass filter is applied. In step 342, a re-sampling is done. In one embodiment, as shown in box 312, the re-sampling may take place over a set of angles. In other embodiments, varying parameters may be used. In step 344, a range limit is applied. In one embodiment, as shown in box 316, a sub-set of angles comprising a range of angles based on the infusion rate. In other embodiments, varying parameters may be used. In step 346, a difference is calculated. In one embodiment, this difference may comprise determining differences in points of the force profile. In other embodiments, this difference may use varying parameters.

FIG. 25 illustrates a graph plotting air sensor data comprising representative points for each of fluid 348, air 350, and transition 352. The Y axis represents an ADC count of the fluid of the chamber measured by a sensor and the X-axis represents sample number. The graph provides the observed air sensor ADC readings versus sample number over 10 aggregated runs. Each run ends with a transition from fluid to air. The fluid readings (hashed symbols) 348, are clearly differentiated from those associated with air (open symbols) 350. Points that are close to or on a transition region from air to fluid are marked by solid symbols 352.

FIG. 26 illustrates a graph plotting force average profiles on the plunger corresponding to the embodiment of FIG. 25 for each of fluid 348, air 350, and transition 352. The graph demonstrates systematic differences in the average force associated with the three states (fluid 348, air 350, and transition 352) of FIG. 25. The Y-axis represents force and the X-axis represents an angular position of the motor powering the plunger.

FIG. 27 illustrates a graph plotting derivatives of the force profiles on the plunger corresponding to the embodiment of FIGS. 26 and 28 for each of fluid 348, air 350, and transition 352. The Y-axis represents a derivative of the force and the X-axis represents an angular position of the motor powering the plunger. The graph demonstrates that the systematic differences between the three states of FIG. 28 can be enhanced and differentiated from mechanism specific variation through the application of the first derivative.

FIG. 28 illustrates a graph applying a principal component analysis to plot representative points at an infusion rate of 2 milliliters per hour, with hashed symbols representing fluid points 348, open symbols representing points associated with air 350, and solid points representing transitional (indeterminant) points 352. The Y-axis represents score 4 and the X-axis represents score 2. The two dimensional view provided in the plot demonstrates a good separation across multiple actuators, fluids, and sets.

FIG. 29 illustrates a graph plotting air sensor data comprising representative points for each of fluid 348, air 350, and transition 352. The Y axis represents an ADC count of the fluid of the chamber measured by a sensor and the X-axis represents sample number. The graph provides the observed air sensor ADC readings versus sample number over 10 aggregated runs. Each run ends with a transition from fluid to air. The fluid readings (hashed symbols) 348, are clearly differentiated from those associated with air (open symbols)

350. Points that are close to or on a transition region from air to fluid are marked by solid symbols 352.

FIG. 30 illustrates a graph plotting force average profiles on the plunger corresponding to the embodiment of FIG. 32 for each of fluid 348, air 350, and transition 352. The graph demonstrates systematic differences in the average force associated with the three states (fluid 348, air 350, and transition 352) of FIG. 29. The Y-axis represents force and the X-axis represents an angular position of the motor powering the plunger.

FIG. 31 illustrates a graph plotting derivatives of the force profiles on the plunger corresponding to the embodiment of FIGS. 30 and 32 for each of fluid 348, air 350, and transition 352. The Y-axis represents a derivative of the force and the X-axis represents an angular position of the motor powering the plunger. The graph demonstrates that the systematic differences between the three states of FIG. 32 can be enhanced and differentiated from mechanism specific variation through the application of the first derivative.

FIG. 32 illustrates a graph applying a principal component analysis to plot representative points at an infusion rate of 1,000 milliliters per hour, with hashed symbols representing fluid points 348, open symbols representing points associated with air 350, and solid points representing transitional (indeterminant) points 352. The Y-axis represents score 4 and the X-axis represents score 2. The two dimensional view provided in the plot demonstrates a good separation across multiple actuators, fluids, and sets.

FIG. 33 illustrates a flowchart for one embodiment of a method 360 for detecting air in a chamber of an infusion system. The method 360 may be implemented using the drug delivery infusion system 100 of FIG. 1 with the plunger being moved with the actuator device against the chamber containing fluid, the sensor detecting a force acting on the plunger as it moves against the chamber, the processor processing the force measurements taken by the sensor and implementing programming code stored in a non-transient memory in order to determine whether air is contained in the chamber using the algorithm set forth in method 360, and the alarm being turned on if the processor determines that air is contained in the chamber which may trigger the pump being shut down. Moreover, the method 360 may utilize the clock of the drug delivery infusion system 100 of FIG. 1 to keep time of activities of the plunger or the sensor, and may use the positional sensor to determine a position of the plunger, with each being in electronic communication with the processor. In other embodiments, the method 360 may utilize varying components to implement the method.

In step 362 a plunger is moved, with an actuator device, against a chamber containing fluid. In step 364 a sensor is used to detect a force acting on the plunger as it moves against the chamber. In step 366 a measurement of the force is electronically communicated from the sensor to a processor. In step 368 the processor: (1) preprocesses a force profile detected by the sensor; (2) extracts features from the force profile; and (3) classifies the force profile as being an air force profile or a liquid force profile based on the extracted features of the force profile. In step 370 the processor turns on an alarm when the processor determines that the chamber contains the air. Step 370 may further comprise shutting down the pump when the alarm is turned on.

In one embodiment, the processor classifies the force profile as being the air force profile or the liquid force profile without applying signal normalization to normalize to a baseline force profile. In another embodiment, the processor further applies a signal normalization to normalize the force profile relative to a baseline force profile. In an additional embodiment, the processor preprocesses the force profile detected by the sensor by: acquiring the force profile; re-sampling the force profile for a set of angles; selecting a sub-set of angles for the force profile; and calculating a derivative of the force profile based on the force profile at the sub-set of angles. In still another embodiment, the processor preprocesses the force profile detected by the sensor by: acquiring the force profile; applying a low pass filter to the force profile; re-sampling the force profile for a set of angles; applying a range limit to the force profile; and calculating a difference of the force profile.

In another embodiment, the processor extracts the features from the force profile by at least one of calculating scores of the force profile or applying a linear discriminate analysis to the force profile. In yet another embodiment, the processor calculates the scores of the force profile by multiplying a derivative of the force profile by a set of eigenvectors, and applies the linear discriminate analysis by multiplying the scores by weights. In an additional embodiment, the processor extracts the features from the force profile using an equation $L=D*(M*W)-D*M*W$, wherein $L$=a linear discriminate analysis, $D$=a derivative, $M$=a set of eigenvectors, and $W$=weights. In another embodiment, the processor classifies the force profile as being the air force profile or the liquid force profile based on means of a linear discriminate analysis applied to the force profile. In other embodiments, any of the steps of the method 360 may be altered, not followed, or additional steps may be added.

In another embodiment, features of the force profile are determined preferably on the basis of force changes versus displacement or position but may also be calculated on the basis of time. The features are a characteristic of the profile that is related to the presence of air or other condition that is desired to be known. For example, features may include: the scores from an abstract factor analysis, such as principal components analysis (PCA); the peak magnitude of the force profile; the phase shift with respect to time or position of the force profile; the maximum or minimum value of the first derivative with respect to position; the correlation coefficient of the force profile with exemplary profiles representing air and fluid; the distance (e.g., Euclidean or Mahalanobis distance) between the observed profile and a set of template profiles; ratios and/or differences between one or more points or averaged regions in the force profile; the correlation between the force profile and additional sensor readings (e.g., proximal and distal pressure); variance of the force profile from the mean; and a difference of the force profile from the mean.

Additionally, the features may be viewed as a set of residuals which represent the difference between the force profile or the derivative of the force profile and the expected value. The expected value may be determined using adaptive filtering, such as Kalman filtering, or as a moving or exponentially weighted moving average. In this scheme, a set of channels are defined which represent the observed force profile at a particular position through time. One or more channels are subjected to analysis through time to detect changes in their expected level on the basis of a model, an averaged profile, and/or a problematic network. When either the residual level exceeds a pre-determined threshold or the probability of an air/fluid transition increases beyond a set level, air is indicated in the pumping chamber.

In the case of the derivative based algorithm, an alternate embodiment involves a series of channels as describe above. Each channel is separately filtered through time using a moving average, spike rejection filter and/or a lowpass filter. This provides a multiplicity of signals that vary through time. The set of signals is then subject to the derivative based algorithm in which change detection occurs using an event detection and change confirmation method, as described previously. Since each channel provides an indication of the fluid chamber status, a method is employed to combine the indicators and provide one final indicator. The preferred method is to always utilize the channel that provides the reading that is most associated with air. For example, this may comprise the channel that experienced the high derivative and greatest change through time. Alternately, aggregation of the signals can occur using a voting algorithm, fuzzy logic, decision trees, support vector machines or Bayesian networks.

In another embodiment, the multiple channels described above may be subjected to an N-th order Kalman filter and used to generate a residual from an expected value. A change is detected when the residual exceeds a pre-set threshold. In other embodiments, other methods may be utilized.

FIG. 34 illustrates a flowchart of a Bayesian network showing a combination of algorithm sensors and a priori information which may be used to produce an indication of air-in-line or air in a chamber. For instance, any of the following air devices, tests, or algorithms may be utilized individually or collectively in different numbers or weights to identify air-in-line 380 or air in the chamber 382 to sound an air alarm 384: a recent proximal pressure change 386; a recent force event indicator 388; a shape indicator 390; a froth indicator (e.g. variance) 392; a dancing bubble indicator 394; an air sensor indicator 396; a recent air sensor indicator 398; a stuck droplet indicator 400; a distal pressure change 402; a flow rate 404; or a fluid type 406. In conjunction with these different tests, the following patents and patent applications are hereby incorporated by reference in full: U.S. Pat. No. 7,981,082; U.S. Ser. No. 61/460,766; and U.S. Ser. No. 61/525,587. The systems, methods, and algorithms/tests of any of the listed incorporated by reference patents may be utilized in conjunction with the systems, methods, and algorithms/tests of the instant disclosure. For example, the air indicator or air alarm as described herein may be used to qualify alarms from other sensors and thereby reduce the probability of nuisance alarms.

One or more systems/methods of the disclosure more accurately detects air in the line of an infusion device than many current systems and methods. The systems/methods of the disclosure may be combined with existing systems/methods for detecting air in an infusion system to improve the reliability of air detection systems. The disclosure allows for the combination of the output of a force sensor signal with one or more air sensors to improve the reliability of existing air detection systems/methods. In doing so, the disclosed system/method does not require additional hardware modifications but instead leverages the acquired force signal. Additionally, the disclosure does not necessarily require the replacement of existing software modules for air detection but adds an additional safety layer to improve the robustness of existing air detection systems and methods.

It should be understood, of course, that the foregoing relates to exemplary embodiments of the disclosure and that modifications may be made without departing from the scope of the disclosure as set forth in the following claims.

What is claimed is:

1. A method for detecting air in a chamber of an infusion system comprising:

preprocessing a force profile based on a measurement of force acting on a plunger as the plunger moves against the chamber containing fluid;

extracting features from the force profile; and classifying the force profile as being an air force profile or a liquid force profile based on the extracted features, wherein the extracted features comprise a shape of the force profile.

2. The method of claim 1, wherein the classifying of the force profile as being the air force profile or the liquid force profile is done without applying signal normalization to normalize to a baseline force profile.

3. The method of claim 1, wherein the preprocessing comprises: acquiring the force profile; re-sampling the force profile for a set of angles; selecting a sub-set of angles for the force profile; and calculating a derivative of the force profile based on the force profile at the sub-set of angles.

4. The method of claim 1, wherein the preprocessing comprises: acquiring the force profile; applying a low pass filter to the force profile; re-sampling the force profile for a set of angles; applying a range limit to the force profile; and calculating a difference of the force profile with respect to a baseline force profile.

5. The method of claim 1, wherein the extracting of the features comprises calculating scores of the force profile or applying a linear discriminate analysis to the force profile.

6. The method of claim 1, further comprising shutting down an infusion pump based on the classifying of the force profile indicating being the air force profile.

7. The method of claim 1, wherein the classifying comprises k-nearest neighbor analysis.

8. The method of claim 1, wherein the classifying comprises support vector machines analysis.

9. The method of claim 1, wherein the classifying comprises a combination of a linear discriminated analysis, a k-nearest neighbor analysis, and a support vector machines analysis.

10. The method of claim 1, wherein the classifying comprises use of Bayesian networks.

11. The method of claim 1, wherein the classifying comprises use of a fuzzy logic algorithm.

12. A system for detecting air in a chamber of an infusion system, the system comprising one or more hardware processors configured to:

preprocess a force profile based on a detected force acting on a plunger as the plunger moves against the chamber containing fluid;

extract features from the force profile; and classify the force profile as being an air force profile or a liquid force profile based on the extracted features, wherein the extracted features comprise a shape of the force profile.

13. The system of claim 12, wherein the classifying of the force profile as being the air force profile or the liquid force profile is done without applying signal normalization to normalize to a baseline force profile.

14. The system of claim 12, wherein the preprocessing comprises: acquiring the force profile; re-sampling the force profile for a set of angles; selecting a sub-set of angles for the force profile; and calculating a derivative of the force profile based on the force profile at the sub-set of angles.

15. The system of claim 12, wherein the preprocessing comprises: acquiring the force profile; applying a low pass filter to the force profile; re-sampling the force profile for a set of angles; applying a range limit to the force profile; and calculating a difference of the force profile with respect to a baseline profile.

16. The system of claim 12, wherein the extracting of the features comprises calculating scores of the force profile or applying a linear discriminate analysis to the force profile.

17. The system of claim 12, wherein the classifying comprises k-nearest neighbor analysis.

18. The system of claim 12, wherein the classifying comprises support vector machines analysis.

19. The system of claim 12, wherein the classifying comprises a combination of a linear discriminated analysis, a k-nearest neighbor analysis, and a support vector machines analysis.

20. The system of claim 12, wherein the classifying comprises use of Bayesian networks.

21. The system of claim 12, wherein the classifying comprises use of a fuzzy logic algorithm.

22. The system of claim 12, wherein the one or more hardware processors are further configured to shut down an infusion pump based on the classifying of the force profile indicating being the air force profile.

* * * * *